United States Patent
Ukanis et al.

(10) Patent No.: US 10,731,152 B2
(45) Date of Patent: *Aug. 4, 2020

(54) METHOD FOR CONTROLLED DNA FRAGMENTATION

(71) Applicant: THERMO FISHER SCIENTIFIC BALTICS UAB, Vilnius (LT)

(72) Inventors: Mindaugas Ukanis, Vilnius (LT); Arvydas Lubys, Vilnius (LT); Romas Tamoševicius, Vilnius (LT); Ervinas Gaidamauskas, Vilnius (LT)

(73) Assignee: THERMO FISHER SCIENTIFIC BALTICS UAB, Vilnius (LT)

( * ) Notice: Subject to any disclaimer, the term of this patent is extended or adjusted under 35 U.S.C. 154(b) by 227 days.

This patent is subject to a terminal disclaimer.

(21) Appl. No.: 14/943,443

(22) Filed: Nov. 17, 2015

(65) Prior Publication Data

US 2016/0177359 A1 Jun. 23, 2016

Related U.S. Application Data

(63) Continuation-in-part of application No. PCT/EP2014/079473, filed on Dec. 30, 2014.

(60) Provisional application No. 61/934,879, filed on Feb. 3, 2014.

(51) Int. Cl.
| | |
|---|---|
| *C12P 19/34* | (2006.01) |
| *C12N 15/10* | (2006.01) |
| *C12Q 1/6806* | (2018.01) |
| *C12Q 1/6874* | (2018.01) |
| *C12Q 1/6855* | (2018.01) |
| *C40B 40/06* | (2006.01) |
| *C40B 50/04* | (2006.01) |
| *C40B 70/00* | (2006.01) |
| *C40B 80/00* | (2006.01) |

(52) U.S. Cl.
CPC ..... *C12N 15/1082* (2013.01); *C12N 15/1093* (2013.01); *C12P 19/34* (2013.01); *C12Q 1/6806* (2013.01); *C12Q 1/6855* (2013.01); *C12Q 1/6874* (2013.01); *C12Q 2521/507* (2013.01); *C12Q 2535/122* (2013.01); *C40B 40/06* (2013.01); *C40B 50/04* (2013.01); *C40B 70/00* (2013.01); *C40B 80/00* (2013.01)

(58) Field of Classification Search
CPC ............ C12Q 1/6806; C12Q 2535/122; C12Q 2521/507; C12Q 1/6874; C12N 15/1082; C12N 15/1093; C12P 19/34
USPC .......................................................... 435/91.2
See application file for complete search history.

(56) References Cited

U.S. PATENT DOCUMENTS

| | | | |
|---|---|---|---|
| 6,593,113 | B1 | 7/2003 | Tenkanen et al. |
| 7,172,882 | B2 | 2/2007 | Savilahti et al. |
| 9,145,623 | B2 | 9/2015 | Kavanagh et al. |
| 9,834,811 | B2 | 12/2017 | Kavanagh et al. |
| 9,885,074 | B2 | 2/2018 | Kavanagh et al. |
| 10,287,622 | B2 | 5/2019 | Belyaev |
| 10,308,978 | B2 | 6/2019 | Kavanagh et al. |
| 2005/0208616 | A1 | 9/2005 | Savilahti et al. |
| 2008/0318801 | A1 | 12/2008 | Leung |
| 2009/0022759 | A1 | 1/2009 | Burgert et al. |
| 2010/0120098 | A1* | 5/2010 | Grunenwald .......... C12N 15/10 435/91.2 |
| 2011/0287435 | A1 | 11/2011 | Grunenwald et al. |
| 2013/0017978 | A1* | 1/2013 | Kavanagh .......... C12N 15/1093 506/26 |
| 2013/0023423 | A1 | 1/2013 | Kavanagh et al. |
| 2013/0261027 | A1* | 10/2013 | Li ...................... C12Q 1/6806 506/26 |
| 2014/0194324 | A1 | 7/2014 | Gormley et al. |
| 2014/0202883 | A1 | 7/2014 | Nobile et al. |
| 2015/0045257 | A1 | 2/2015 | Kavanagh et al. |
| 2015/0197799 | A1 | 7/2015 | Rigatti et al. |
| 2015/0353926 | A1 | 12/2015 | Rigatti et al. |
| 2016/0046980 | A1 | 2/2016 | Kavanagh et al. |
| 2016/0046985 | A1* | 2/2016 | Drmanac ............ C12Q 1/6806 506/4 |
| 2016/0362748 | A1 | 12/2016 | Mongan et al. |
| 2017/0009288 | A1 | 1/2017 | Ukanis et al. |
| 2018/0037935 | A1 | 2/2018 | Kavanagh et al. |
| 2018/0201976 | A1 | 7/2018 | Kavanagh et al. |

(Continued)

FOREIGN PATENT DOCUMENTS

| | | |
|---|---|---|
| EP | 3102691 A1 | 12/2016 |
| EP | 3377625 A1 | 9/2018 |
| EP | 3102691 B1 | 9/2019 |

(Continued)

OTHER PUBLICATIONS

PCT/US2016/062334, International Search Report and Written Opinion dated Feb. 15, 2017, 1-13 pages.

(Continued)

*Primary Examiner* — Cynthia B Wilder

(57) ABSTRACT

A composition and method for controlled in vitro fragmentation of nucleic acids. A transposase forms catalytically active complexes with a modified transposon end that contains within its end sequence degenerate, apurinic/apyrimidinic sites, nicks, or nucleotide gaps, to fragment or shear a target nucleic acid sample in a controlled process. This method yields desired average nucleic acid fragment sizes. The inventive composition and method may be applied for generation of DNA fragments containing shortened transposon end sequences to facilitate subsequent reactions, for production of asymmetrically tailed DNA fragments, etc.

20 Claims, 39 Drawing Sheets

Specification includes a Sequence Listing.

(56) References Cited

U.S. PATENT DOCUMENTS

| | | |
|---|---|---|
| 2019/0078083 A1 | 3/2019 | Ukanis et al. |
| 2019/0300937 A1 | 10/2019 | Kavanagh et al. |

FOREIGN PATENT DOCUMENTS

| | | |
|---|---|---|
| WO | WO-9523875 A1 | 9/1995 |
| WO | WO-2010/048605 | 4/2010 |
| WO | WO-2012106546 A2 | 8/2012 |
| WO | 2015/113725 A1 | 8/2015 |
| WO | 2015/189636 A1 | 12/2015 |
| WO | 2016/201142 A1 | 12/2016 |
| WO | WO-2017087555 A1 | 5/2017 |

OTHER PUBLICATIONS

Goldhaber-Gordon, Ilana et al., "Sequence and Positional Requirements for DNA Sites in a Mu Transpososome", *The Journal of Biological Chemistry*, vol. 277, No. 10, 2001, 7703-7712.

PCT/EP2014/079473, International Search Report and Written Opinion dated Jun. 17, 2015, 13 pages.

Saariaho, Anna-Helena et al., "Characteristics of MuA transposase-catalyzed processing of model transposon end DNA hairpin substrates", *Nucleic Acids Research*, vol. 34, No. 10, 2006, 3139-3149.

Alzbutas et al., "MuA Transposase Enzyme Enables Fast and Easy DNA Library Preparation for Next Generation Sequencing", Poster presented in connection with a qPCR-NGS-2013.net Symposium at Technical University of Munich, Freising-Weihenstephan Germany Mar. 18-22, 2013, https://www.gene-quantification.de/qper-ngs-2013/posters/, p. 1.

Montano S.P., et al., "The Mu Transpososome Structure Sheds Light on DDE Recombinase Evolution," Nature, Nov. 15, 2012, vol. 491, pp. 413-417.

International Preliminary Report on Patentability for PCT/EP2014/079473, 9 pages, dated Aug. 9, 2016.

International Preliminary Report on Patentability for PCT/US2016/062334, 6 pages, dated May 22, 2018.

Boeke, J.D. Transposable elements in Saccharomyces cerevisiae in Mobile DNA, 1989, pp. 335-374.

Butterfield et al. An efficient strategy for large-scale high-throughput transposon-mediated sequencing of cDNA clones. Nucleic Acids Research vol. 30, No. 11, (2002) 2460-2468.

Craig, N. L. Transposon Tn7, Current Topics in Microbiology and Immunology, 1996, 204:27-48.

Devine S. E., et al. Efficient integration of artificial transposons into plasmid targets in vitro: a useful tool for DNA mapping, sequencing and genetic analysis, Nucleic Acids Research, 1994, 22:18, pp. 3765-3772.

Haapa S. et al. An efficient and accurate integration of mini-Mu transposons in vitro: a general methodology for functional genetic analysis and molecular biology applications, Nucleic Acids Research, 1999, 27:13, pp. 2777-2784.

Happa et al. An Efficient DNA Sequencing Strategy Based on the Bacteriophage Mu in Vitro DNA Transposition Reaction. Genome Research 9 (1999) 308-315.

Ichikawa H. et al. In Vitro Transposition of Transposon Tn3. The Journal of Biological Chemistry 1990, 265:31, pp. 18829-18832.

Kaufman P. D. et al. P. Element transposition in vitro proceeds by a cut-and-paste mechanism and uses GTP as a cofactor, Cell, 1992, 69, pp. 27-39.

Kleckner N. et al., Tn10 and IS10 transposition and chromosome rearrangements: mechanism and regulation in vivo and in vitro, Current Topics in Microbiology and Immunology, 1996, 204:, pp. 49-82.

Lampe, D. J. et al., A purified mariner transposase is sufficient to mediate transposition in vitro, The EMBO Journal, 1996, 15:19, pp. 5470-5479.

Laurent et al. Functional Characterization of the Human Immunodeficiency Virus Type 1 Genome by Genetic Footprinting, J. Virology, vol. 74, No. 6 (2000), pp. 2760-2769.

Liu et al. H-NS. mediates the dissociation of a refractory protein-DNA complex during TN10/IS10 transposition. Nucleic Acids Research, May 11, 2011, vol. 39, No. 15, pp. 6660-6668.

Munoz-Lopez. DNA Transposons: Nature and Applications in Genomics. Current Genomics 11 (2010) 115-128.

Ohtsubo, E. et al., Bacterial insertion sequences, Current Topics in Microbiology and Immunology, 1996, 204, pp. 1-26.

Park, B. T. et al. In Vitro transposition of Tn5, J. Korean Soc. Microbial., 1992, 27:4, pp. 381-389.

Reznikoff, Tn5 as a model for understanding DNA transposition. Molecular Microbiology 47(5), (2003) 1199-1206.

Savilahti, H. et al., Mu transpositional recombination: donor DNA cleavage and strand transfer in trans by the Mu transposase, Cell, 1996, 85, pp. 271-280.

Savilahti H. et al. The phage Mu transpososome core: DNA requirements for assembly and function, EMBO Journal, 1995, 14:19, pp. 4893-4903.

Varmus H. et al., Retroviruses, in Mobile DNA, Berg D.E. And Howe M. eds. American Society for Microbiology, 1989, pp. 53-108.

Vos J. C. et al. Transposase is the only nematode protein required for in vitro transposition of Tc 1, Genes & Development, 1996, 10(6), pp. 755-761.

\* cited by examiner

| 579 M AQ17 Total Bases | | | |
|---|---|---|---|
| Alignment Summary | | | |
|  | AQ17 | AQ20 | Perfect |
| Total Number of Bases [bp] | 579 M | 543 M | 444 M |
| Mean Length [bp] | 178 | 171 | 146 |
| Longest Alignment [bp] | 324 | 316 | 310 |
| Mean Coverage depth | 123.7 | 115.9 | 94.9 |

FIG. 6F

METHOD FOR CONTROLLED DNA FRAGMENTATION

This application is a continuation-in-part application of International Application No. PCT/EP2014/079473, with an International filing date of Dec. 30, 2014, which claims priority to U.S. Provisional Application No. 61/934,879, filed on Feb. 3, 2014.

REFERENCE TO SEQUENCE LISTING SUBMITTED VIA EFS-WEB

This application includes an electronically submitted sequence listing in .txt format. The .txt file contains a sequence listing entitled "2016-02-12 TF18770US1-PCT_ST25.txt" created on Feb. 12, 2016 and is 9,441 bytes in size. The sequence listing contained in this .txt file is part of the specification and is hereby incorporated by reference herein in its entirety.

Throughout this application various publications, patents, and/or patent applications are referenced. The disclosures of these publications, patents, and/or patent applications in their entireties are hereby incorporated by reference into this application in order to more fully describe the state of the art to which this invention pertains.

FIELD OF INVENTION

The invention relates to the field of controlled fragmentation of nucleic acids.

SUMMARY

In some embodiments, the disclosure relates generally to compositions, as well as related methods, systems, kits and apparatuses, comprising one or more transpososome complexes.

In some embodiments, a plurality of transpososome complexes comprises a plurality of individual transpososome complexes, where individual transpososome complexes comprise: (i) a plurality of transposases, (ii) a polynucleotide containing a first transposon end sequence, and (iii) a polynucleotide containing a second transposon end sequence.

In some embodiments, the first transposon end sequence is capable of binding to the plurality of transposases.

In some embodiments, the second transposon end sequence is capable of binding to the plurality of transposases.

In some embodiments, the first transposon end sequence contains at least one modification, including a lesion such as a nick, gap, apurinic site or apyrimidinic site.

In some embodiments, the second transposon end sequence contains at least one modification, including a lesion such as a nick, gap, apurinic site or apyrimidinic site.

In some embodiments, the first and the second transposon end sequences contain at least one modification, including a lesion such as a nick, gap, apurinic site or apyrimidinic site.

In some embodiments, the first or the second transposon end sequence lacks a modification, including a lesion such as a nick, gap, apurinic site or apyrimidinic site.

In some embodiments, the first and the second transposon end sequences within an individual transpososome complex have identical or different sequences.

Optionally, the plurality of transpososome complexes contains individual transpososome complexes which include (i) one or more transposases and (ii) a pair of transposon end sequences (e.g. first and second transposon end sequences) having the same sequence, where the first and second transposon end sequences of any given transpososome complex has the same sequence of the first and second transposon end sequences of substantially all other transpososome complexes in the plurality of transpososome complexes (homo-transpososome complexes).

Optionally, the plurality of transpososome complexes includes a mixture of different sets of transpososome complexes, where the transpososome complexes in the different sets include (i) one or more transposases and (ii) a pair of transposon end sequences (e.g. first and second transposon end sequences) having the same sequence, and where the sequence of the first and second transposon end sequences from one set differs compared to the sequence of the first and second transposon end sequences from any other set (hetero-transpososome complexes). Optionally, the mixture of different sets of transpososome complexes contains 2-100 or more different sets of transpososome complexes.

In some embodiments, the plurality of transpososome complexes comprise a plurality of individual transpososome complexes, where individual transpososome complexes comprise: (i) a plurality of transposases, (ii) a polynucleotide containing a first transposon end sequence, wherein the first transposon end sequence contains at least one modification, including a lesion such as a nick, gap, apurinic site or apyrimidinic site, and (iii) a polynucleotide containing a second transposon end sequence, wherein the second transposon end sequence contains at least one modification, including a lesion such as a nick, gap, apurinic site or apyrimidinic site. In some embodiments, the first transposon end sequence is capable of binding to the plurality of transposases. In some embodiments, the second transposon end sequence is capable of binding to the plurality of transposases. Optionally, the transpososome complex comprises two, three, four or more transposases. Optionally, the first and the second transposon end sequences within an individual transpososome complex have identical or different sequences. Optionally, the plurality of transpososome complexes comprises a plurality of homo-transpososome complexes or a mixture of hetero-transpososome complexes.

In some embodiments, the transpososome complex is contained in a single reaction mixture. For example, the single reaction mixture can be contained in a single reaction vessel or in a single well.

In some embodiments, the transpososome complex can be produced by conducting any method for preparing the transposon complex, or any method for fragmenting DNA in vitro, described herein.

In some embodiments, the disclosure relates generally to compositions, as well as related methods, systems, kits and apparatuses, comprising a plurality of transpososome complexes, where individual transposome complexes include (i) a plurality of transposases, (ii) a first transposon end sequence, and (iii) a second transposon end sequence, wherein the first transposon end sequence contains at least one modification, including a lesion such as at least one nick, gap, apurinic site or apyrimidinic site, wherein the second transposon end sequence optionally contains at least one modification, including a lesion such as at least one nick, gap, apurinic site or apyrimidinic site, wherein the first transposon end sequence is capable of binding to the plurality of transposases, wherein the second transposon end sequence is capable of binding to the plurality of transposases, and wherein the first and second transposon end sequences are the same (e.g., homo-transpososome complexes).

In some embodiments, the disclosure relates generally to compositions, as well as related methods, systems, kits and apparatuses, comprising a mixture of different transpososome complexes which includes at least 2 different sets of transpososome complexes. The mixture can contain 2-100 or more different sets of transpososome complexes. In some embodiments, individual transpososome complexes within each set include: (i) a plurality of transposases, (ii) a first transposon end sequence, and (iii) a second transposon end sequence, wherein the first transposon end sequence contains at least one modification, including a lesion such as at least one nick, gap, apurinic site or apyrimidinic site, wherein the second transposon end sequence optionally contains at least one modification, including a lesion such as at least one nick, gap, apurinic site or apyrimidinic site, wherein the first transposon end sequence is capable of binding to the plurality of transposases, wherein the second transposon end sequence is capable of binding to the plurality of transposases, wherein the first and second transposon end sequences within each set are the same, and wherein the first and second transposon end sequences of a first set differ from the first and second transposon end sequences of any other set in the mixture of transpososome complexes (e.g., hetero-transpososome complexes).

In some embodiments, the disclosure relates generally to compositions, as well as related methods, systems, kits and apparatuses, comprising a transpososome/target nucleic acid complex.

In some embodiments a transpososome/target nucleic acid complex comprises: (i) a plurality of transposases, (ii) a polynucleotide containing a first transposon end sequence, (iii) a polynucleotide containing a second transposon end sequence, and (iv) a target nucleic acid molecule. In some embodiments, the target nucleic acid molecule comprises a target DNA molecule.

In some embodiments, the first transposon end sequence is capable of binding to the plurality of transposases.

In some embodiments, the second transposon end sequence is capable of binding to the plurality of transposases.

In some embodiments, the first transposon end sequence contains at least one modification, including a lesion such as a nick, gap, apurinic site or apyrimidinic site.

In some embodiments, the second transposon end sequence contains at least one modification, including a lesion such as a nick, gap, apurinic site or apyrimidinic site.

In some embodiments, the first and the second transposon end sequences contain at least one modification, including a lesion such as a nick, gap, apurinic site or apyrimidinic site.

In some embodiments, the first or the second transposon end sequence lacks a modification, including a lesion such as a nick, gap, apurinic site or apyrimidinic site.

In some embodiments, the first and the second transposon end sequences have identical or different sequences.

Optionally, the plurality of transpososome complexes comprises a plurality of homo-transpososome complexes or a mixture of hetero-transpososome complexes.

In some embodiments a plurality of transpososome/target nucleic acid complexes comprises a plurality of individual transpososome/target nucleic acid complexes, where the individual transpososome/target nucleic acid complexes comprise: (i) a plurality of transposases, (ii) a polynucleotide containing a first transposon end sequence, wherein the first transposon end sequence is capable of binding to the plurality of transposases and wherein the first transposon end sequence contains at least one modification, including a lesion such as a nick, gap, apurinic site or apyrimidinic site, (iii) a polynucleotide containing a second transposon end sequence, wherein the second transposon end sequence is capable of binding to the plurality of transposases and wherein the second transposon end sequence contains at least one modification, including a lesion such as a nick, gap, apurinic site or apyrimidinic site, and (iv) a target nucleic acid molecule. In some embodiments, the target nucleic acid molecule comprises a target DNA molecule. Optionally, the transpososome complex comprises two, three, four or more transposases. In some embodiments, the first and the second transposon end sequences have identical or different sequences. Optionally, the plurality of transpososome complexes comprises a plurality of homo-transpososome complexes or a mixture of hetero-transpososome complexes.

In some embodiments, the transpososome/target DNA complex can be produced by conducting any method for preparing the transposome/target DNA complex, or any method for fragmenting DNA in vitro, described herein.

In some embodiments, the disclosure relates generally to compositions, as well as related methods, systems, kits and apparatuses, comprising a nucleic acid fragmentation reaction mixture. In some embodiments, the nucleic acid fragmentation reaction mixture comprises: (i) a plurality of transposases, (ii) a polynucleotide containing a first transposon end sequence, (iii) a polynucleotide containing a second transposon end sequence, (iv) a target nucleic acid molecule, and (v) an activating cation.

In some embodiments, the first transposon end sequence is capable of binding to the plurality of transposases.

In some embodiments, the second transposon end sequence is capable of binding to the plurality of transposases.

In some embodiments, the first transposon end sequence contains at least one modification, including a lesion such as a nick, gap, apurinic site or apyrimidinic site.

In some embodiments, the second transposon end sequence contains at least one modification, including a lesion such as a nick, gap, apurinic site or apyrimidinic site.

In some embodiments, the first and the second transposon end sequences contain at least one modification, including a lesion such as a nick, gap, apurinic site or apyrimidinic site.

In some embodiments, the first or the second transposon end sequence lacks a modification, including a lesion such as a nick, gap, apurinic site or apyrimidinic site.

In some embodiments, the first and the second transposon end sequences have identical or different sequences.

Optionally, the plurality of transpososome complexes comprises a plurality of homo-transpososome complexes or a mixture of hetero-transpososome complexes.

In some embodiments, the activating agent includes one or any combination of magnesium and/or manganese.

In some embodiments, the nucleic acid fragmentation reaction mixture comprises: (i) a plurality of transposases, (ii) a polynucleotide containing a first transposon end sequence, wherein the first transposon end sequence is capable of binding to the plurality of transposases and wherein the first transposon end sequence contains at least one modification, including a lesion such as a nick, gap, apurinic site or apyrimidinic site, (iii) a polynucleotide containing a second transposon end sequence, wherein the second transposon end sequence is capable of binding to the plurality of transposases and wherein the second transposon end sequence contains at least one modification, including a lesion such as a nick, gap, apurinic site or apyrimidinic site, (iv) a target nucleic acid molecule, and (v) an activating cation (e.g., magnesium or manganese). In some embodiments, the target nucleic acid molecule comprises a target DNA molecule. In some embodiments, the first and the second transposon end sequences have identical or different sequences. Optionally, the plurality of transpososome complexes comprises a plurality of homo-transpososome complexes or a mixture of hetero-transpososome complexes.

In some embodiments, the nucleic acid fragmentation reaction mixture further comprises a buffer (e.g., Tris-HCl), an alkali metal (e.g., NaCl and/or KCl), a detergent (e.g., TritonX-100, TritonX-114, NP-40, Brij, Tween-20, SDS, or CHAPS), and an activating cation (e.g., magnesium or manganese). Optionally, the nucleic acid fragmentation reaction mixture lacks any activating cation (e.g., magnesium or manganese). For example, an activating cation includes any cation required by a transposase for catalyzing a transposition reaction. In some embodiments, a nucleic acid fragmentation reaction mixture lacks an activating cation (or contains a very low level of activating cation).

In some embodiments, the disclosure relates generally to compositions, as well as related methods, systems, kits and apparatuses, comprising a fragmented nucleic acid molecule.

In some embodiments, the fragmented nucleic acid molecule comprises: (i) a first end of the DNA molecule joined to the first transposon end sequence and (ii) a second end of the DNA molecule joined to the second transposon end sequence.

In some embodiments, the first transposon end sequence includes at least one modification, including a lesion such as a nick, gap, apurinic site or apyrimidinic site.

In some embodiments, the second transposon end sequence includes at least one modification, including a lesion such as a nick, gap, apurinic site or apyrimidinic site.

In some embodiments, the first and the second transposon end sequences contain at least one modification, including a lesion such as a nick, gap, apurinic site or apyrimidinic site.

In some embodiments, the first or the second transposon end sequence lacks a modification, including a lesion such as a nick, gap, apurinic site or apyrimidinic site.

In some embodiments, the first and the second transposon end sequences have identical or different sequences. Optionally, the plurality of transpososome complexes comprises a plurality of homo-transpososome complexes or a mixture of hetero-transpososome complexes.

In some embodiments, the fragmented DNA molecule, or a plurality of fragmented DNA molecules, can be produced by conducting any method for preparing a plurality of transposon complexes, or any method for fragmenting DNA in vitro, described in the present teachings.

In some embodiments, the plurality of fragmented DNA molecules have a size range of about 100-2000 bp, or about 100-250 bp, or about 250-500 bp, or about 500-750 bp, or about 750-1000 bp, or about 1000-1250 bp, or about 1250-1500 bp, or about 1500-1750 bp, or about 1750-2000 bp.

In some embodiments, the disclosure relates generally to compositions, as well as related methods, systems, kits and apparatuses, comprising a single reaction mixture containing a nucleic acid amplification reaction mixture.

In some embodiments, the single reaction mixture permits conducting the amplification reaction after the fragmentation/tagging step, in the same reaction mixture and in the same reaction vessel, without any intervening steps to remove the fragmentation reaction mixture to a new reaction vessel. The reaction mixture used to fragment target DNA molecules, using any of the transpososome complexes or any of the transpososome/target nucleic acid complexes described herein, can also be used to amplify the fragmented DNA molecules. Optionally, the nucleic acid fragmentation and the amplification steps are performed in a different reaction mixture, in the same or in a different reaction vessel.

In some embodiments, the single reaction mixture containing a nucleic acid amplification reaction mixture comprises: a nucleic acid fragmentation reaction mixture, at least one fragmented DNA molecule and at least one component for amplifying nucleic acids.

For example, components for amplifying nucleic acids include any one or any combination of: primers, polymerase and/or nucleotides.

In some embodiments, the single reaction mixture containing a nucleic acid amplification reaction mixture comprises: (i) a nucleic acid fragmentation reaction mixture, (ii) at least one fragmented DNA molecule, (iii) one or more primers that hybridize with at least a portion of the fragmented DNA molecule or a sequence that is complementary to the fragmented DNA molecule, (iv) one or more polymerases, and (v) one or more nucleotides.

For example, the nucleic acid fragmentation reaction mixture includes any one or any combination of: a buffer (e.g., Tris-HCl), a salt (e.g., NaCl and/or KCl), a detergent (e.g., TritonX-100), and/or an activating cation (e.g., magnesium or manganese).

In some embodiments, at least one end of a fragmented DNA molecule is joined to the first transposon end sequence having at least one modification. Optionally, the at least one modification includes a lesion such as a nick, gap, apurinic site or apyrimidinic site.

In some embodiments, at least one end of a fragmented DNA molecule is joined to the second transposon end sequence having at least one modification. Optionally, the at least one modification includes a lesion such as a nick, gap, apurinic site or apyrimidinic site.

In some embodiments, the fragmented DNA molecule is joined at a first end to a first transposon end sequence, and is joined at a second end to a second transposon end sequence, and the first and the second transposon end sequences have identical or different sequences. Optionally, the plurality of transpososome complexes comprises a plurality of homo-transpososome complexes or a mixture of hetero-transpososome complexes.

In some embodiments, the disclosure relates generally to compositions, as well as related methods, systems, kits and apparatuses, comprising transpososome complexes in the presence of one or more stabilizing agents.

In some embodiments, the transpososome complexes comprise: (i) a plurality of transposases, (ii) a polynucleotide containing a first transposon end sequence, (iii) a polynucleotide containing a second transposon end sequence, and (iv) at least one stabilizing agent.

In some embodiments, the first transposon end sequence is capable of binding to the plurality of transposases.

In some embodiments, the second transposon end sequence is capable of binding to the plurality of transposases.

In some embodiments, the first transposon end sequence contains at least one modification, including a lesion such as a nick, gap, apurinic site or apyrimidinic site.

In some embodiments, the second transposon end sequence contains at least one modification, including a lesion such as a nick, gap, apurinic site or apyrimidinic site.

In some embodiments, the first and the second transposon end sequences contain at least one modification, including a lesion such as a nick, gap, apurinic site or apyrimidinic site.

In some embodiments, the first or the second transposon end sequence lacks a modification, including a lesion such as a nick, gap, apurinic site or apyrimidinic site.

In some embodiments, the first and the second transposon end sequences have identical or different sequences. Optionally, the plurality of transpososome complexes comprises a plurality of homo-transpososome complexes or a mixture of hetero-transpososome complexes.

In some embodiments, the stabilizing agent includes any compound that stabilizes the structure, conformation and/or activity of a protein or enzyme. In some embodiments, the stabilizing agent includes any compound that increases the solubility of a protein or enzyme in solution. In some embodiments, the stabilizing agent includes any compound that decreases protein aggregation.

In some embodiments, one or more stabilizing agents is added before, during or after the transpososome complexes are formed. In some embodiments, the stabilizing agent includes any compound that, when added to the transpososome complexes, helps retain some or all transpososome-mediated activity. For example, the presence of one or more stabilizing agent can retain about 5-20%, or about 20-40%, or about 40-60%, or about 60-80%, or about 80-95%, or about 95-100% activity. Optionally, the shelf-life of the transpososome complexes can be extended by adding one or more stabilizing agents. Optionally, the transpososome complexes, in the presence of at least one stabilizing agent, can retain some or all enzyme activity during shipping. In some embodiments, the transpososome complexes, in the presence of at least one stabilizing agent, can be stored or shipped at about −20° C.

In some embodiments, the transpososome complexes comprise: (i) a plurality of transposases, (ii) a polynucleotide containing a first transposon end sequence, wherein the first transposon end sequence is capable of binding to the plurality of transposases and wherein the first transposon end sequence contains at least one modification, including a lesion such as a nick, gap, apurinic site or apyrimidinic site, (iii) a polynucleotide containing a second transposon end sequence, wherein the second transposon end sequence is capable of binding to the plurality of transposases and wherein the second transposon end sequence contains at least one modification, including a lesion such as a nick, gap, apurinic site or apyrimidinic site, and (iv) at least one stabilizing agent. In some embodiments, the first and the second transposon end sequences have identical or different sequences. Optionally, the plurality of transpososome complexes comprises a plurality of homo-transpososome complexes or a mixture of hetero-transpososome complexes.

For example, the stabilizing agent includes any amino acid including charged amino acids. Optionally, the stabilizing agent includes any one or any combination of arginine, histidine, lysine, aspartic acid, glutamic acid (Golovanvo, et al., 2004 Journal of Am. Chem. Soc. 126(29): 8933-8939, Baynes, Wang and Trout 2005 Biochemistry 44(12):4919-4925, Shukla and Trout 2011 Journal of Phys. Chem B 115(41):11831). In some embodiments, the stabilizing agent includes a mixture of arginine and glutamic acid. In some embodiments, the stabilizing agent comprises a polyol. In some embodiments, the stabilizing agent includes any one or any combination of glycol, propylene glycol, and/or glycerol. In some embodiments, the stabilizing agent comprises a polysaccharide. In some embodiments, the stabilizing agent comprises any one or any combination of sucrose, trehalose, polyhydric alcohol, glucose (e.g., L- or D-glucose), and/or galactose (e.g., D-galactose). In some embodiments, the transpososome complex includes BSA.

In some embodiments, the disclosure relates generally to kits, as well as related compositions, methods, systems, and apparatuses, comprising components for assembling a plurality of transpososome complexes, including: (i) a plurality of transposases, (ii) a polynucleotide containing a first transposon end sequence, and (iii) a polynucleotide containing a second transposon end sequence.

In some embodiments, the disclosure relates generally to kits, as well as related compositions, methods, systems, and apparatuses, comprising pre-assembled transpososome complexes, which include: (i) a plurality of transposases, (ii) a plurality of polynucleotides containing a first transposon end sequence, and (iii) a plurality of polynucleotides containing a second transposon end sequence. Optionally, the pre-assembled transpososome complexes comprises two, three, four or more transposases.

In some embodiments, the first transposon end sequence is capable of binding to the plurality of transposases.

In some embodiments, the second transposon end sequence is capable of binding to the plurality of transposases.

In some embodiments, the first transposon end sequence contains at least one modification, including a lesion such as a nick, gap, apurinic site or apyrimidinic site.

In some embodiments, at least one first transposon end sequence lacks a modification (e.g., a lesion such as a nick, gap, apurinic site or apyrimidinic site).

In some embodiments, the plurality of first transposon end sequences includes a plurality of double-stranded polynucleotides having a first strand (e.g., an attacking strand) and second strand (e.g., a non-attacking strand).

In some embodiments, the second transposon end sequence contains at least one modification, including a lesion such as a nick, gap, apurinic site or apyrimidinic site.

In some embodiments, at least one second transposon end sequence lacks a modification (e.g., a lesion such as a nick, gap, apurinic site or apyrimidinic site).

In some embodiments, the plurality of second transposon end sequences includes a plurality of double-stranded polynucleotides having a first strand (e.g., an attacking strand) and second strand (e.g., a non-attacking strand).

In some embodiments, the first and the second transposon end sequences contain at least one modification, including a lesion such as a nick, gap, apurinic site or apyrimidinic site.

In some embodiments, the first and the second transposon end sequences have identical or different sequences. Optionally, the plurality of transpososome complexes comprises a plurality of homo-transpososome complexes or a mixture of hetero-transpososome complexes.

In some embodiments, the kits, as well as related compositions, methods, systems, and apparatuses, further comprise one or more activating cation. For example, the activating cation includes magnesium and manganese.

In some embodiments, the kits, as well as related compositions, methods, systems, and apparatuses, further comprise one or more stabilizing agent. For example, the stabilizing agent includes any compound that stabilizes the structure, conformation and/or activity of a protein or enzyme. In some embodiments, the stabilizing agent includes any compound that increases the solubility of a protein or enzyme in solution. In some embodiments, the stabilizing agent includes any compound that decreases protein aggregation. For example, the stabilizing agent includes any amino acid including charged amino acids. Optionally, the stabilizing agent includes any one or any combination of arginine, histidine, lysine, aspartic acid, glutamic acid (Golovanvo, et al., 2004 Journal of Am. Chem. Soc. 126(29):8933-8939, Baynes, Wang and Trout 2005 Biochemistry 44(12):4919-4925, Shukla and Trout 2011 Journal of Phys. Chem B 115(41):11831). In some embodiments, the stabilizing agent includes a mixture of arginine and glutamic acid. In some embodiments, the stabilizing agent comprises a polyol. In some embodiments, the stabilizing agent includes any one or any combination of glycol, propylene glycol, and/or glycerol. In some embodiments, the stabilizing agent comprises a polysaccharide. In some embodiments, the stabilizing agent comprises any one or any combination of sucrose, trehalose, polyhydric alcohol, glucose (e.g., L- or D-glucose), and/or galactose (e.g., D-galactose). In some embodiments, the kits, as well as related compositions, methods, systems, and apparatuses, further comprise BSA.

In some embodiments, the kits, as well as related compositions, methods, systems, and apparatuses, further comprise one or more containers for holding the components for assembling transpososome complexes or the pre-assembled transpososome complexes.

In some embodiments, the kits, as well as related compositions, methods, systems, and apparatuses, can also include buffers and reagents. For example, the buffers can include Tris, Tricine, HEPES, or MOPS, or chelating agents such as EDTA or EGTA. The buffers or reagents can include monovalent ions, such as KCl, K-acetate, $NH_4$-acetate, K-glutamate, $NH_4Cl$, or ammonium sulfate. In yet another example, the reagents can include divalent ions, such as $Ca^{2+}$, $Mg^{2+}$, $Mn^{2+}$, or $CaCl_2$, $MgCl_2$, $MnCl_2$, or Mg-acetate, and the like.

In some embodiments, the kits, as well as related compositions, methods, systems, and apparatuses, further include instructions for performing the controlled nucleic acid fragmentation reactions.

In some embodiments, the disclosure relates generally to methods, as well as related compositions, systems, kits and apparatuses, for preparing a plurality of transpososome complexes.

In some embodiments, methods for preparing a plurality of transpososome complexes comprise contacting a plurality of transposases with a plurality of polynucleotides.

In some embodiments, the plurality of transposases is contacted with the plurality of polynucleotides in a single reaction mixture. For example, the single reaction mixture can be contained in a single reaction vessel or a single well (e.g., a single reaction chamber).

In some embodiments, methods for preparing a plurality of transpososome complexes comprise contacting in a single reaction mixture a plurality of transposases with a plurality of polynucleotides.

In some embodiments, the plurality of polynucleotides contain a plurality of first transposon end sequences, a plurality of second transposon end sequences, or a mixture of first and second transposon end sequences.

In some embodiments, the first transposon end sequences are capable of recognizing and binding a transposase.

In some embodiments, the plurality of first transposon end sequences includes at least one modification. Optionally, the at least one modification includes a lesion such as a nick, gap, apurinic site or apyrimidinic site.

In some embodiments, at least one first transposon end sequence lacks a modification (e.g., a lesion such as a nick, gap, apurinic site or apyrimidinic site).

In some embodiments, the plurality of first transposon end sequences includes a plurality of double-stranded polynucleotides having a first strand (e.g., an attacking strand) and second strand (e.g., a non-attacking strand).

In some embodiments, the second transposon end sequences are capable of recognizing and binding a transposase.

In some embodiments, the plurality of second transposon end sequences includes at least one modification. Optionally, the at least one modification includes a lesion such as a nick, gap, apurinic site or apyrimidinic site.

In some embodiments, at least one second transposon end sequence lacks a modification (e.g., a lesion such as a nick, gap, apurinic site or apyrimidinic site).

In some embodiments, the plurality of second transposon end sequences includes a plurality of double-stranded polynucleotides having a first strand (e.g., an attacking strand) and second strand (e.g., a non-attacking strand).

In some embodiments, the first and the second transposon end sequences have identical or different sequences.

Optionally, the plurality of transpososome complexes contains individual transpososome complexes which include (i) one or more transposases and (ii) a pair of transposon end sequences (e.g. first and second transposon end sequences) having the same sequence, where the first and second transposon end sequences of any given transpososome complex has the same sequence of the first and second transposon end sequences of substantially all other transpososome complexes in the plurality of transpososome complexes (homo-transpososome complexes).

Optionally, the plurality of transpososome complexes includes a mixture of different sets of transpososome complexes, where the transpososome complexes in the different sets include (i) one or more transposases and (ii) a pair of transposon end sequences (e.g. first and second transposon end sequences) having the same sequence, and where the sequence of the first and second transposon end sequences from one set differs compared to the sequence of the first and second transposon end sequences from any other set (heterotranspososome complexes). Optionally, the mixture of different sets of transpososome complexes contains 2-100 or more different sets of transpososome complexes.

In some embodiments, one or more stabilizing agents is added before, during or after the transpososome complexes are formed. For example, the stabilizing agent includes any amino acid including charged amino acids. Optionally, the stabilizing agent includes any one or any combination of arginine, histidine, lysine, aspartic acid, glutamic acid (Golovanvo, et al., 2004 Journal of Am. Chem. Soc. 126 (29):8933-8939, Baynes, Wang and Trout 2005 Biochemistry 44(12):4919-4925, Shukla and Trout 2011 Journal of Phys. Chem B 115(41):11831). In some embodiments, the stabilizing agent includes a mixture of arginine and glutamic acid. In some embodiments, the stabilizing agent comprises a polyol. In some embodiments, the stabilizing agent includes any one or any combination of glycol, propylene glycol, and/or glycerol. In some embodiments, the stabilizing agent comprises a polysaccharide. In some embodiments, the stabilizing agent comprises any one or any combination of sucrose, trehalose, polyhydric alcohol, glucose (e.g., L- or D-glucose), and/or galactose (e.g., D-galactose). In some embodiments, the transpososome complex includes BSA.

In some embodiments, the disclosure relates generally to methods, as well as related compositions, systems, kits and apparatuses, for preparing a plurality of transpososome complexes, comprise: (a) contacting in a single reaction mixture (i) a plurality of transposases, (ii) a plurality of polynucleotides containing a first transposon end sequence, wherein the first transposon end sequence is capable of binding to a transposase from the plurality of transposases, and (iii) a plurality of polynucleotides containing a second transposon end sequence, wherein the second transposon end sequence is capable of binding to a transposase from the plurality of transposases; and (b) forming at least one transpososome complex having a transposase, a first transposon end sequence, and a second transposon end sequence, wherein the first transposon end sequence contains at least one modification, including a lesion such as at least one nick, gap, apurinic site or apyrimidinic site, and wherein the second transposon end sequence optionally contains at least one modification, including a lesion such as at least one nick, gap, apurinic site or apyrimidinic site. Optionally, the transposome complex may contain a plurality of transposases, including two, three, four or more transposases. Optionally, the plurality of transpososome complexes comprises a plurality of homo-transpososome complexes or a mixture of hetero-transpososome complexes. Optionally, one or more stabilizing agents is added after the transpososome complexes are formed.

In some embodiments, the disclosure relates generally to methods, as well as related compositions, systems, kits and apparatuses, for preparing a plurality of hetero-transpososome complexes, which includes at least a first and a second transpososome complex, comprising: (a) contacting in a first reaction mixture (i) a first plurality of transposases that can form at least a first transpososome complex, (ii) a plurality of polynucleotides containing a first transposon end sequence, wherein the first transposon end sequence is capable of binding to the first transpososome complex, and the plurality of polynucleotides containing a second transposon end sequence, wherein the second transposon end sequence is capable of binding to the first transpososome complex; and (b) forming at least the first transpososome complex having a plurality of transposases, the first transposon end sequence, and the second transposon end sequence, wherein the first transposon end sequence contains at least one modification, including a lesion such as at least one nick, gap, apurinic site or apyrimidinic site, and wherein the second transposon end sequence optionally contains at least one modification, including a lesion such as at least one nick, gap, apurinic site or apyrimidinic site; (c) contacting in a second reaction mixture (e.g., which is separate from the first reaction mixture) (i) a second plurality of transposases that can form at least a second transpososome complex, (ii) a plurality of polynucleotides containing a third transposon end sequence, wherein the third transposon end sequence is capable of binding to the second transpososome complex, and the plurality of polynucleotides containing a fourth transposon end sequence, wherein the fourth transposon end sequence is capable of binding to the second transpososome complex; and (d) forming at least the second transpososome complex having a plurality of transposases, the third transposon end sequence, and the fourth transposon end sequence, wherein the third transposon end sequence contains at least one modification, including a lesion such as at least one nick, gap, apurinic site or apyrimidinic site, and wherein the fourth transposon end sequence optionally contains at least one modification, including a lesion such as at least one nick, gap, apurinic site or apyrimidinic site.

Optionally, the first and second transposon end sequences contain sequences that are identical or different with each other. Optionally, the first transposome complex contains a plurality of transposases, including two, three, four or more transposases. Optionally, one or more stabilizing agents is added after the first transpososome complexes are formed.

Optionally, the third and fourth transposon end sequences contain sequences that are identical or different with each other. Optionally, the second transposome complex contains a plurality of transposases, including two, three, four or more transposases. Optionally, one or more stabilizing agents are added after the second transpososome complexes are formed.

Optionally, the first and second transposon end sequences contain sequences that are identical with each other, and the third and fourth transposon end sequences contain sequences that are identical with each other, and the first and second transposon end sequences differ from the third and fourth transposon end sequences.

One skilled in the art will appreciate that a third, fourth, and fifth transposome complexes (and many more) can be prepared in separate single reaction mixtures (e.g., third, fourth, fifth, and many more separate single reaction mixtures) in the same manner as described herein, where the third, fourth, and fifth transposome complexes (and many more) each include a plurality of transposases and two transposon end sequences, where the two transposon end sequences contain at least one modification, including a lesion such as at least one nick, gap, apurinic site or apyrimidinic site, and where the two transposon end sequences differ between the third, fourth and fifth transpososome complexes.

In some embodiments, the disclosure relates generally to methods, as well as related compositions, systems, kits and apparatuses, for fragmenting nucleic acids. In some embodiments, methods for fragmenting nucleic acids comprise contacting a plurality of transpososome complexes with a plurality of target polynucleotides. In some embodiments, the plurality of transpososome complexes is contacted with the plurality of target polynucleotides in an in vitro reaction. In some embodiments, the plurality of transpososome complexes is contacted with the plurality of target polynucleotides in a single reaction mixture. For example, the single reaction mixture can be contained in a single reaction vessel or a single well (e.g., a single reaction chamber). In some embodiments, in vitro methods for fragmenting nucleic acids comprise contacting in a single reaction mixture a plurality of transpososome complexes with a plurality of target polynucleotides. In some embodiments, at least one transpososome complex in the plurality of transpososome complexes comprises a first transposon end sequence and a second transposon end sequence. In some embodiments, at least one transpososome complex in the plurality of transpososome complexes comprises a first transposon end sequence having at least one modification. Optionally, the at least one modification includes a lesion such as a nick, gap, apurinic site or apyrimidinic site. In some embodiments, at least one transpososome complex in the plurality of transpososome complexes comprises a second transposon end sequence having at least one modification. Optionally, the at least one modification includes a lesion such as a nick, gap, apurinic site or apyrimidinic site. In some embodiments, at least one transpososome complex in the plurality of transpososome complexes comprises a first or a second transposon end sequence that lacks a modification (e.g., a lesion such as a nick, gap, apurinic site or apyrimidinic site). In some embodiments, the first and the second transposon end sequences have identical or different sequences. Optionally, the plurality of transpososome complexes comprises a plurality of homo-transpososome complexes or a mixture of hetero-transpososome complexes. In some embodiments, in vitro methods for fragmenting nucleic acids comprise transposing the first or the second transposon end sequences into the target DNA molecule and fragmenting the target DNA molecule, and joining a first end of a DNA fragment to the first transposon end sequence or the second transposon end sequence. In some embodiments, in vitro methods for fragmenting nucleic acids comprise transposing the first and the second transposon end sequences into the target DNA molecule and fragmenting the target DNA molecule, and joining a first end of a DNA fragment to the first transposon end sequence and optionally joining a second end of the DNA fragment to the second transposon end sequence. In some embodiments, at least one end of a fragmented DNA molecule is joined to the first transposon end sequence having at least one modification. Optionally, the at least one modification includes a lesion such as a nick, gap, apurinic site or apyrimidinic site. In some embodiments, at least one end of a fragmented DNA molecule is joined to the second transposon end sequence having at least one modification. Optionally, the at least one modification includes a lesion such as a nick, gap, apurinic site or apyrimidinic site. In some embodiments, the fragmented DNA molecule is joined at a first end to a first transposon end sequence, and is joined at a second end to a second transposon end sequence, and the first and the second transposon end sequences have identical or different sequences.

In some embodiments, the disclosure relates generally to methods, as well as related compositions, systems, kits and apparatuses, for fragmenting DNA in vitro, comprise: (a) forming a plurality of transpososome complexes by contacting in a single reaction mixture (i) a plurality of transposases, (ii) a plurality of polynucleotides containing a first transposon end sequence, wherein the first transposon end sequence is capable of binding to a transposase from the plurality of transposases, and (iii) a plurality of polynucleotides containing a second transposon end sequence, wherein the second transposon end sequence is capable of binding to a transposase from the plurality of transposases, wherein the first transposon end sequence contains at least one modification, including a lesion such as at least one nick, gap, apurinic site or apyrimidinic site, and wherein the second transposon end sequence optionally contains at least one modification, including a lesion such as at least one nick, gap, apurinic site or apyrimidinic site, (b) contacting the plurality of transpososome complexes with a plurality of target nucleic acids (e.g., target DNA), and (c) transposing the first and the second transposon end sequences into the target DNA molecule and fragmenting the target DNA molecule, and joining a first end of a DNA fragment to the first transposon end sequence and optionally joining a second end of the DNA fragment to the second transposon end sequence. Optionally, the transposome complexes may contain a plurality of transposases, including two, three, four or more transposases. In some embodiments, one or more stabilizing agents is added before, during or after the transpososome complexes are formed. Optionally, one or more stabilizing agents are added after the transpososome complexes are formed (e.g., before step (b)). Optionally, the first and the second transposon end sequences have identical or different sequences.

In some embodiments, the disclosure relates generally to methods, as well as related compositions, systems, kits and apparatuses, for preparing a plurality of transpososome complexes, or for fragmenting DNA in vitro, which further comprise: producing at least one fragmented DNA molecule, by transposing the first and the second transposon end sequences into the target DNA molecule and fragmenting the target DNA molecule, and joining a first end of a DNA fragment to the first transposon end sequence and optionally joining a second end of the DNA fragment to the second transposon end sequence. Optionally, the first and the second transposon end sequences, which are joined to the ends of the target DNA molecule, have identical or different sequences.

In some embodiments, the disclosure relates generally to methods, as well as related compositions, systems, kits and apparatuses, for preparing a plurality of transpososome complexes, or for fragmenting DNA in vitro, which further comprise: forming at least one transpososome/target DNA complex by contacting the plurality of transpososome complexes with a plurality of target nucleic acid molecules. Optionally, the plurality of target nucleic acid molecules comprises DNA molecules.

In some embodiments, the disclosure relates generally to methods, as well as related compositions, systems, kits and apparatuses, for preparing a plurality of transpososome complexes, or for fragmenting DNA in vitro, which further comprise: producing at least one fragmented DNA molecule, by transposing the first and the second transposon end sequences into the target DNA molecule and fragmenting the target DNA molecule, and joining a first end of a DNA fragment to the first transposon end sequence and optionally joining a second end of the DNA fragment to the second transposon end sequence.

Optionally, the at least one fragmented DNA molecule includes a first transposon end sequence having at least one modification, including a lesion such as at least one nick, gap, apurinic site or apyrimidinic site.

Optionally, the at least one fragmented DNA molecule includes a second transposon end sequence having at least one modification, including a lesion such as at least one nick, gap, apurinic site or apyrimidinic site.

Optionally, the first and the second transposon end sequences have identical or different sequences.

In some embodiments, the disclosure relates generally to methods, as well as related compositions, systems, kits and apparatuses, for fragmenting DNA in vitro, comprise:

(a) providing a plurality of transpososome complexes, which includes at least a first and second transpososome complex, wherein the first transpososome complex includes (i) a first plurality of transposases, (ii) a first transposon end sequence, and (iii) a second transposon end sequence, wherein the first transposon end sequence contains at least one modification, including a lesion such as at least one nick, gap, apurinic site or apyrimidinic site, and wherein the second transposon end sequence optionally contains at least one modification, including a lesion such as at least one nick, gap, apurinic site or apyrimidinic site; (b) contacting in a single reaction mixture the plurality of transpososome complexes, including the first transpososome complex, with a plurality of target nucleic acids (e.g., target DNA), which includes a first target DNA molecule; (c) transposing the first and the second transposon end sequences into the first target DNA molecule using the first transpososome complex and fragmenting the first target DNA molecule at a first location, thereby generating a first double-stranded break in the first target DNA molecule, where the first double-stranded break includes a first and a second end, and joining the first end of the first double-stranded break to the first transposon end sequence and optionally joining the second end of the first double-stranded break to the second transposon end sequence, where the first transposon end sequence that is joined to the first end of the first double-stranded break contains at least one modification, including a lesion such as at least one nick, gap, apurinic site or apyrimidinic site, where the second transposon end sequence that is joined to the second end of the first double-stranded break contains at least one modification, including a lesion such as at least one nick, gap, apurinic site or apyrimidinic site; (d) transposing the first and the second transposon end sequences into the first target DNA molecule using the second transpososome complex and fragmenting the first target DNA molecule at a second location which differs from the first location, thereby generating a second double-stranded break in the first target DNA molecule, where the second double-stranded break includes a third and a fourth end, and joining the third end of the second double-stranded break to the first transposon end sequence and optionally joining the fourth end of the second double-stranded break to the second transposon end sequence, where the first transposon end sequence that is joined to the third end of the second double-stranded break contains at least one modification, including a lesion such as at least one nick, gap, apurinic site or apyrimidinic site, where the second transposon end sequence that is joined to the third end of the second double-stranded break contains at least one modification, including a lesion such as at least one nick, gap, apurinic site or apyrimidinic site. Optionally, the first and second transposon end sequences contain sequences that are identical with each other. Optionally, the first transposomosome complex contains a plurality of transposases, including two, three, four or more transposases. Optionally, the plurality of transpososome complexes comprises a plurality of homo-transpososome complexes In some embodiments, the disclosure relates generally to methods, as well as related compositions, systems, kits and apparatuses, for fragmenting DNA in vitro, using a plurality of transpososome complexes, where different transpososome complexes include a different transposon end sequence (e.g., hetero-transpososome complexes), to produce a population of fragmented target DNA molecules having both ends joined to a transposon end sequence, and optionally where a plurality of fragmented target DNA molecules within the population have a first end and a second end that is joined to a second transposon end sequence, and where the first and second ends are joined to transposon end sequences having different sequences.

In some embodiments, the disclosure relates generally to methods, as well as related compositions, systems, kits and apparatuses, for fragmenting DNA in vitro, comprise:
(a) providing a plurality of transpososome complexes, which includes at least a first and a second transpososome complex, wherein (i) the first transpososome complex includes a first plurality of transposases, a first transposon end sequence, and a second transposon end sequence, wherein the first transposon end sequence contains at least one modification, including a lesion such as at least one nick, gap, apurinic site or apyrimidinic site, and wherein the second transposon end sequence optionally contains at least one modification, including a lesion such as at least one nick, gap, apurinic site or apyrimidinic site, and (ii) the second transpososome complex includes a second plurality of transposases, a third transposon end sequence, and a fourth transposon end sequence, wherein the third transposon end sequence contains at least one modification, including a lesion such as at least one nick, gap, apurinic site or apyrimidinic site, and wherein the fourth transposon end sequence optionally contains at least one modification, including a lesion such as at least one nick, gap, apurinic site or apyrimidinic site; (b) contacting in a single reaction mixture the plurality of transpososome complexes, including the first and the second transpososome complexes, with a plurality of target nucleic acids (e.g., target DNA), which includes a first target DNA molecule; (c) transposing the first and the second transposon end sequences into the first target DNA molecule using the first transpososome complex and fragmenting the first target DNA molecule at a first location, thereby generating a first double-stranded break in the first target DNA molecule, where the first double-stranded break includes a first and a second end, and joining the first end of the first double-stranded break to the first transposon end sequence and optionally joining the second end of the first double-stranded break to the second transposon end sequence, where the first transposon end sequence that is joined to the first end of the first double-stranded break contains at least one modification, including a lesion such as at least one nick, gap, apurinic site or apyrimidinic site, where the second transposon end sequence that is joined to the second end of the first double-stranded break contains at least one modification, including a lesion such as at least one nick, gap, apurinic site or apyrimidinic site; (d) transposing the third and the fourth transposon end sequences into the first target DNA molecule using the second transpososome complex and fragmenting the first target DNA molecule at a second location (e.g., which differs from the first location), thereby generating a second double-stranded break in the first target DNA molecule, where the second double-stranded break includes a third and a fourth end, and joining the third end of the second double-stranded break to the third transposon end sequence and optionally joining a fourth end of the second double-stranded break to the fourth transposon end sequence, where the third transposon end sequence that is joined to the third end of the second double-stranded break contains at least one modification, including a lesion such as at least one nick, gap, apurinic site or apyrimidinic site, where the fourth transposon end sequence that is joined to the fourth end of the second double-stranded break contains at least one modification, including a lesion such as at least one nick, gap, apurinic site or apyrimidinic site.

Optionally, the first and second transposon end sequences contain sequences that are identical or different with each other. Optionally, the third and fourth transposon end sequences contain sequences that are identical or different with each other. Optionally, the first and second transposon end sequences contain sequences that are identical with each other, and the third and fourth transposon end sequences contain sequences that are identical with each other, and the first and second transposon end sequences differ from the third and fourth transposon end sequences. Optionally, the plurality of transpososome complexes comprises mixture of hetero-transpososome complexes. Optionally, the first transposomosome complex contains a plurality of transposases, including two, three, four or more transposases. Optionally, the second transposomosome complex contains a plurality of transposases, including two, three, four or more transposases.

In some embodiments, an improved workflow can include reducing or eliminating separate steps to remove the transposase enzymes that may inhibit a subsequent step. It is postulated that the transposase enzyme remains bound to the DNA fragments (which are joined at the ends to the transposon end sequences), and inhibits a subsequent primer extension reaction (e.g., PCR reaction). One advantage of conducting a transpososome-mediated DNA fragmentation reaction with the transposon end sequence described herein, is that the first, second, third and/or fourth transposon end sequences having at least one nick or gap, which may reduce the number of hydrogen bonds between the first and second strands of the transposon end sequences, which may lead to dissociation of the single-stranded terminal portion of the transposon end sequence without the need for a separate removal or extraction step. For example, use of any of the transposon end sequence that are described herein, may reduce or obviate the need to perform separate SDS and/or phenol extractions to remove the transposase enzymes, and optionally can permit conducting a subsequent reaction (e.g., PCR reaction) in the same reaction vessel and/or the same reaction mixture. The absence of the terminal portion of the transposon end sequence may lead to dissociation of the transposase enzyme from the transposon end sequence after the transposon-mediated fragmentation step. A PCR reaction can be conducted in the same reaction mixture (and in the same reaction vessel) once the terminal portion of the transposon end sequence and the transposase dissociate from the fragmented DNA. Since a separate chemical extraction step is not necessary, and the fragmented DNA need not be transferred to a separate reaction vessel, the workflow can be streamlined and automated.

In some embodiments, methods for preparing a plurality of transpososome complexes, or methods for fragmenting DNA in vitro, further comprise: reducing the length of the first transposon end sequence which is joined to the target DNA, by truncating a terminal portion of the attacking strand at the location of the first nick (i.e., disintegration).

In some embodiments, methods for preparing a plurality of transpososome complexes, or methods for fragmenting DNA in vitro, further comprise: reducing the length of the first transposon end sequence which is joined to the target DNA, by truncating a terminal portion of the non-attacking strand at the location of the second nick (i.e., disintegration).

In some embodiments, methods for preparing a plurality of transpososome complexes, or methods for fragmenting DNA in vitro, further comprise: reducing the length of the second transposon end sequence which is joined to the target DNA, by truncating a terminal portion of the attacking strand at the location of the first nick (i.e., disintegration).

In some embodiments, methods for preparing a plurality of transpososome complexes, or methods for fragmenting DNA in vitro, further comprise: reducing the length of the second transposon end sequence which is joined to the target DNA, by truncating a terminal portion of the non-attacking strand at the location of the second nick (i.e., disintegration).

Optionally, the plurality of transpososome complexes comprises mixture of hetero-transpososome complexes.

In some embodiments, any one or any combination of the following steps can be conducted manually or by automation, including: preparing a plurality of transpososome complexes, forming a plurality of transpososome/target DNA complexes, producing at least one fragmented DNA molecule, adaptor-appending, amplifying the fragmented DNA molecule (e.g., via PCR), denaturing the amplified target DNA, immobilizing the plurality of single-stranded fragmented DNA to a support, sequencing, and/or fragmenting the target DNA. For example, any reagents employed to conduct any of these steps can be reacted together (contacted) in one or more reaction vessels. Non-limiting examples of the reagents include: transposases, first transposon end sequences, second transposon end sequences, target DNA molecules, PCR reagents (e.g., amplification polymerase, primers, tailed primers and/or nucleotides), sequencing reagents (e.g., sequencing polymerase, primers and/or nucleotides), activating agents (e.g., magnesium and/or manganese) and/or stabilizing agents.

In some embodiments, the disclosure relates generally to methods, as well as related compositions, systems, kits and apparatuses, for preparing a plurality of transpososome complexes, or for fragmenting DNA in vitro, further comprise: controlling the average length of the fragmented DNA molecules which can be achieved by any one or any combination of: (i) varying the amount of transpososome complexes which is contacted with the plurality of target DNA, (ii) varying the amount of target DNA which is contacted with the transpososome complexes, (iii) varying the amount of time of the transposition reaction, and/or (iv) varying the location of the nick or gap on the transposon end sequence.

In some embodiments, methods for preparing a plurality of transpososome complexes, or methods for fragmenting DNA in vitro, further comprise: amplifying the at least one fragmented DNA molecule to produce amplified fragmented DNA molecules. In some embodiments, the amplifying step can be conducted in the same reaction vessel and/or in the same reaction mixture, without intervening steps (e.g., SDS treatment and/or phenol extraction) or transfer to a fresh reaction vessel.

In some embodiments, the amplifying step can be conducted by a polymerase chain reaction (PCR) for example using tailed and/or non-tailed amplification primers (U.S. Pat. Nos. 4,683,195 and 4,683,202 both granted to Mullis); ligase chain reaction (LCR) (Barany 1991 Proceedings National Academy of Science USA 88:189-193, Barnes 1994 Proceedings National Academy of Science USA91: 2216-2220); or isothermal self-sustained sequence reaction (Kwoh 1989 Proceedings National Academy of Science USA 86:1173-1177, WO 1988/10315, and U.S. Pat. Nos. 5,409,818, 5,399,491, and 5,194,370); or recombinase polymerase amplification (RPA) (U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308).

In some embodiments, amplifying the at least one fragmented DNA molecule comprises: contacting the at least one fragmented DNA molecule with (i) one or more primers that hybridize with at least a portion of the fragmented DNA molecule or a sequence that is complementary to the fragmented DNA molecule, (ii) one or more polymerases, and (iii) one or more nucleotides. Optionally, the amplifying can be conducted under isothermal or thermo-cycling conditions. Optionally, the one or more polymerases comprise thermo-stable or thermal-labile polymerases. Optionally, the amplifying can be conducted in the presence of bovine serum albumin (BSA).

In some embodiments, the amplifying step is conducted in the same reaction mixture, and in the same reaction vessel, that is used to conduct the nucleic acid fragmentation step. The reaction mixture used for fragmenting DNA molecules, using any of the transpososome complexes or any of the transpososome/target nucleic acid complexes described herein, can also be used to amplify the fragmented DNA molecule. For example, transpososome complexes may be contacted with target DNA molecules in a reaction mixture containing a buffer (e.g., Tris-HCl), a salt (e.g., NaCl and/or KCl), a detergent (e.g., TritonX-100), and an activating cation (e.g., magnesium or manganese) to fragment the target DNA molecules. Optionally, the activating agent can be added separately to start the amplification reaction. Optionally, components for amplifying nucleic acids (e.g., primers, polymerase and nucleotides) are added to the fragmentation reaction mixture, using the same reaction vessel, to amplify the fragmented DNA molecules.

In some embodiments, the disclosure relates generally to methods, as well as related compositions, systems, kits and apparatuses, for preparing a plurality of transpososome complexes, or for fragmenting DNA in vitro, further comprise: denaturing the fragmented DNA molecules, or the amplified target DNA, to produce a plurality of single-stranded fragmented DNA. Optionally, the fragmented DNA molecules can be denatured using a chemical compound or heat.

In some embodiments, the disclosure relates generally to methods, as well as related compositions, systems, kits and apparatuses, for preparing a plurality of transpososome complexes, or for fragmenting DNA in vitro, further comprise: attaching a plurality of fragmented DNA (single-stranded or double-stranded) to a support. In some embodiments, the plurality of fragmented DNA attached to a support includes attachment to the surface of a support, or to the interior scaffold of the support. In some embodiments, the plurality of fragmented DNA is hybridization to capture oligonucleotides that are attached to the support. In some embodiments, the plurality of fragmented DNA is attached to the support by a chemical compound without hybridization to capture oligonucleotides. In some embodiments, any chemical compound that can be used to attach nucleic acids to a support, can be used to attach fragmented DNA molecules or capture oligonucleotides to the support. For example, the support can be coated with an acrylamide, carboxylic or amine compound for attaching nucleic acids (e.g., capture oligonucleotides or fragmented DNA). In another example, amino-modified nucleic acids can be attached to a support that is coated with a carboxylic acid. In some embodiments, amino-modified nucleic acids can be reacted with ethyl (dimethylaminopropyl) carbodiimide (EDC) or EDAC for attachment to a carboxylic acid coated support (with or without N-hydroxysuccinimide (NHS)). In yet another example, nucleic acids can be immobilized to an acrylamide compound coating on a support. In some embodiments, the support can be coated with an avidin-like compound (e.g., streptavidin) for binding biotinylated nucleic acids.

In some embodiments, the disclosure relates generally to methods, as well as related compositions, systems, kits and apparatuses, for preparing a plurality of transpososome complexes, or for fragmenting DNA in vitro, further comprise: sequencing the plurality of single-stranded fragmented DNA with a massively parallel sequencing reaction.

In some embodiments, the massively parallel sequencing reaction comprises incorporating a nucleotide (e.g., a nucleic acid sequence-by-synthesis reaction) or ligation-based reaction (e.g., SOLiD sequencing, Applied Biosystems/Life Technologies).

In some embodiments, the disclosure relates generally to methods, as well as related compositions, systems, kits and apparatuses, for preparing a plurality of transpososome complexes, or for fragmenting DNA in vitro, wherein the massively parallel sequencing reaction comprises providing a surface having a plurality of reaction sites (e.g., array). Optionally, the plurality of reaction sites is arranged in an organized or random pattern.

In some embodiments, at least one reaction site is operatively linked to one or more sensors.

In some embodiments, the one or more sensors detect at least one byproduct or cleavage product of a nucleotide incorporation reaction.

In some embodiments, the byproduct or cleavage product of a nucleotide incorporation reaction includes ions (e.g., hydrogen ions), protons, phosphate groups, including pyrophosphate groups.

In some embodiments, the one or more sensors detect a change in ions, hydrogen ions, protons, phosphate groups, including pyrophosphate groups.

In some embodiments, the one or more sensors comprise a field effect transistor (FET).

Optionally, the sensor comprises an ion-sensitive field effect transistor (ISFET).

In some embodiments, a plurality of fragmented DNA molecules can be produced by conducting any method using any transpososome complex described herein, including any plurality of homo-transpososome complexes or a mixture of hetero-transpososome complexes.

In some embodiments, the disclosure relates generally to methods, as well as related compositions, systems, kits and apparatuses, for preparing a plurality of transpososome complexes, or for fragmenting DNA in vitro, wherein the plurality of first transposon end sequences includes a plurality of double-stranded polynucleotides having a first and second strand.

In some embodiments, the first transposon end sequences include first strands containing at least one modification (e.g., at least one modification includes a lesion such as a nick, gap, apurinic site or apyrimidinic site).

In some embodiments, the first transposon end sequences include second strands which optionally contain at least one modification (e.g., at least one modification includes a lesion such as a nick, gap, apurinic site or apyrimidinic site).

In some embodiments, the first transposon end sequences include double-stranded polynucleotides containing first strands having at least one modification, and second strands containing at least one modification, where the modification(s) on the first strands are located at a different position than the modification(s) on the second strands. Optionally, the modifications include a lesion such as a nick, gap, apurinic site or apyrimidinic site.

In some embodiments, the first transposon end sequences include double-stranded polynucleotides containing first and second strands, where at least one first strand or at least one second strand lacks a modification.

In some embodiments, the first transposon end sequence includes an identification sequence (e.g., barcode sequence), a primer extension sequence, or a sequence which is complementary to a primer extension sequence. Optionally, a primer extension sequence includes an amplification primer sequence or a sequencing primer sequence.

In some embodiments, the disclosure relates generally to methods, as well as related compositions, systems, kits and apparatuses, for preparing a plurality of transpososome complexes, or for fragmenting DNA in vitro, wherein the plurality of second transposon end sequences includes a plurality of double-stranded polynucleotides having a first and second strand.

In some embodiments, the second transposon end sequences include first strands containing at least one modification (e.g., at least one modification includes a lesion such as a nick, gap, apurinic site or apyrimidinic site).

In some embodiments, the second transposon end sequences include second strands which optionally contain at least one modification (e.g., at least one modification includes a lesion such as a nick, gap, apurinic site or apyrimidinic site).

In some embodiments, the second transposon end sequences include double-stranded polynucleotides containing first strands having at least one modification, and second strands containing at least one modification, where the modification(s) on the first strands are located at a different position than the modification(s) on the second strands. Optionally, the modifications include a lesion such as a nick, gap, apurinic site or apyrimidinic site.

In some embodiments, the second transposon end sequences include double-stranded polynucleotides containing first and second strands, where at least one first strand or at least one second strand lacks a modification.

In some embodiments, the second transposon end sequence includes an identification sequence (e.g., barcode sequence), a primer extension sequence, or a sequence which is complementary to a primer extension sequence. Optionally, a primer extension sequence includes an amplification primer sequence or a sequencing primer sequence.

In some embodiments, the disclosure relates generally to methods, as well as related compositions, systems, kits and apparatuses, for preparing a plurality of transpososome complexes, or for fragmenting DNA in vitro, wherein the first and the second transposon end sequences have identical or different sequences.

In some embodiments, the disclosure relates generally to methods, as well as related compositions, systems, kits and apparatuses, for preparing a plurality of transpososome complexes, or for fragmenting DNA in vitro, wherein the first transposon end sequence comprises a double-stranded polynucleotide having a first attacking strand and a first non-attacking strand.

In some embodiments, the first attacking strand includes a least one modification, including a lesion such as at least one nick, gap, apurinic site or apyrimidinic site.

In some embodiments, the first non-attacking strand includes a least one modification, including a lesion such as at least one nick, gap, apurinic site or apyrimidinic site.

Optionally, the first transposon end sequence includes a first attacking strand and a first non-attacking strand, wherein the first attacking strand and/or the first non-attacking strand include a least one modification, including a lesion such as at least one nick, gap, apurinic site or apyrimidinic site.

In some embodiments, the first transposon end sequences include a first attacking strand and a first non-attacking strand, wherein the first attacking strand or the first non-attacking strand lacks a modification.

In some embodiments, the disclosure relates generally to methods, as well as related compositions, systems, kits and apparatuses, for preparing a plurality of transpososome complexes, or for fragmenting DNA in vitro, wherein the second transposon end sequence comprises a double-stranded polynucleotide having a second attacking strand and a second non-attacking strand.

In some embodiments, the second attacking strand includes a least one modification, including a lesion such as at least one nick, gap, apurinic site or apyrimidinic site.

In some embodiments, the second non-attacking strand includes a least one modification, including a lesion such as at least one nick, gap, apurinic site or apyrimidinic site.

Optionally, the second transposon end sequence includes a second attacking strand and a second non-attacking strand, wherein the second attacking strand and/or the second non-attacking strand include a least one modification, including a lesion such as at least one nick, gap, apurinic site or apyrimidinic site.

In some embodiments, the second transposon end sequences include a first attacking strand and a first non-attacking strand, wherein the first attacking strand or the first non-attacking strand lacks a modification.

Optionally, the first and/or the second transposon end sequence includes an attacking strand having a nick which is located at any position, including after the sixth, eighth, tenth, fourteenth, sixteenth, eighteenth, nineteenth or twenty-seventh nucleotide from the 3' end of the attacking strand (see FIG. 8).

Optionally, the first and/or the second transposon end sequence includes a non-attacking strand having a nick which is located at any position, including after the eleventh, thirteenth, twenty-fifth or twenty-seventh nucleotide from the 5' end of the attacking strand (see FIG. 8).

In some embodiments, the disclosure relates generally to methods, as well as related compositions, systems, kits and apparatuses, for preparing a plurality of transpososome complexes, or for fragmenting DNA in vitro, wherein the transpososome complexes include a transposase enzyme comprising any transposase enzyme, including a DDE transposase enzyme such as a prokaryotic transposase enzyme from ISs, Tn3, Tn5, Tn7, and Tn10, bacteriophage transposase enzyme from phage Mu (Nagy and Chandler 2004, reviewed by Craig et al. 2002; U.S. Pat. No. 6,593,113), and eukaryotic "cut and paste" transposase enzymes (Jurka et al. 2005; Yuan and Wessler 2011). In some embodiments, the transposase enzymes include retroviral transposases, such as HIV (Dyda et al. 1994; Haren et al. 1999; Rice et al. 1996; Rice and Baker 2001).

In some embodiments, the disclosure relates generally to methods, as well as related compositions, systems, kits and apparatuses, for preparing a plurality of transpososome complexes, or for fragmenting DNA in vitro, wherein the transpososome complexes include a first and/or the second transposon end sequence comprising any transposon sequence (e.g., a transposon end sequence) from a prokaryotic insertion sequences including (ISs), Tn3, Tn5, Tn7, and Tn10, bacteriophage included phage Mu (Nagy and Chandler 2004, reviewed by Craig et al. 2002), and eukaryotic "cut and paste" transposons (Jurka et al. 2005; Yuan and Wessler 2011). In some embodiments, the first and/or the second transposon end sequence includes any transposon sequence from retroviruses such as HIV (Dyda et al. 1994; Haren et al. 1999; Rice et al. 1996; Rice and Baker 2001).

In some embodiments, the first transposon end sequence comprises a MuA transposon end sequence, Mos1 transposon end sequence, Vibrio harvey transposon end sequence, or Tn5 transposon end sequence.

In some embodiments, the second transposon end sequence comprises a MuA transposon end sequence, Mos1 transposon end sequence, Vibrio harvey transposon end sequence, or Tn5 transposon end sequence.

In some embodiments, the transposase enzyme comprises a MuA, Mos1, Vibrio harvey, ISs, Tn3, Tn5, Tn7, or Tn10 transposase.

In some embodiments, the first and second transposon end sequences comprise MuA transposon end sequences and the transposase comprises a MuA transposase.

In some embodiments, the first and second transposon end sequences comprise Mos1 transposon end sequences and the transposase comprises a Mos1 transposase.

In some embodiments, the first and second transposon end sequences comprise Vibrio harvey transposon end sequences and the transposase comprises a Vibrio harvey transposase.

In some embodiments, the first and second transposon end sequences comprise Tn5 transposon end sequences and the transposase comprises a Tn5 transposase.

In some embodiments, the disclosure relates generally to methods, as well as related compositions, systems, kits and apparatuses, for preparing a plurality of transpososome complexes, or for fragmenting DNA in vitro, wherein any combination of reagents used to conduct any step or reaction described herein can be deposited into one or more reaction vessels in any order, including sequentially or substantially simultaneously or a combination of both. Non-limiting examples of the reagents include: transposases, first transposon end sequences, second transposon end sequences, target DNA molecules, PCR reagents (e.g., amplification polymerase, primers and/or nucleotides), sequencing reagents (e.g., sequencing polymerase, primers and/or nucleotides), activating agents and/or stabilizing agents.

BRIEF DESCRIPTION OF THE DRAWINGS

FIG. 6F shows Ion Torrent PGM DNA library, prepared from *E. coli* gDNA fragmented with 44-6 pre-nicked transposon end containing MuA transpososome, run summary fragments: alignment summary.

FIG. 7A-1 shows an Agilent 2100 Bioanalyzer curve of fragmented (using native transposon ends human gDNA.

FIG. 7A-2 shows an Agilent 2100 Bioanalyzer curve of fragmented (using native transposon ends) and then amplified human gDNA.

FIG. 7B-1 shows an Agilent 2100 Bioanalyzer curve of fragmented (using 34-16 pre-nicked transposon ends) human gDNA.

FIG. 7B-2 shows an Agilent 2100 Bioanalyzer curve of fragmented (using 34-16 pre-nicked transposon ends) and then amplified human gDNA.

FIG. 10A-1 shows an Agilent 2100 Bioanalyzer curve of fragmented *E. coli* gDNA illustrating DNA fragment length dependence on the transposon end structure assembled into MuA transpososome, amount (0.5 µl) of MuA transpososome containing native transposon ends and in vitro transposition reaction time (1.5 min).

FIG. 10A-2 shows an Agilent 2100 Bioanalyzer curves of fragmented *E. coli* gDNA illustrating DNA fragment length dependence on the transposon end structure assembled into MuA transpososome, amount (0.5 µl) of MuA transpososome containing native transposon ends and in vitro transposition reaction time (5 min).

FIG. 10A-3 shows an Agilent 2100 Bioanalyzer curves of fragmented *E. coli* gDNA illustrating DNA fragment length dependence on the transposon end structure assembled into MuA transpososome, amount (0.5 µl) of MuA transpososome containing native transposon ends and in vitro transposition reaction time (10 min).

FIG. 10A-4 shows an Agilent 2100 Bioanalyzer curve of fragmented *E. coli* gDNA illustrating DNA fragment length dependence on the transposon end structure assembled into MuA transpososome, amount (0.5 µl) of MuA transpososome containing 38-12 nicked transposon ends and in vitro transposition reaction time (1.5 min).

FIG. 10A-5 shows an Agilent 2100 Bioanalyzer curve of fragmented *E. coli* gDNA illustrating DNA fragment length dependence on the transposon end structure assembled into MuA transpososome, amount (0.5 µl) of MuA transpososome containing 38-12 nicked transposon ends and in vitro transposition reaction time (5 min).

FIG. 10A-6 shows an Agilent 2100 Bioanalyzer curve of fragmented *E. coli* gDNA illustrating DNA fragment length dependence on the transposon end structure assembled into MuA transpososome, amount (0.5 µl) of MuA transpososome containing 38-12 nicked transposon ends and in vitro transposition reaction time (10 min).

FIG. 10A-7 shows an Agilent 2100 Bioanalyzer curve of fragmented *E. coli* gDNA illustrating DNA fragment length dependence on the transposon end structure assembled into MuA transpososome, amount (0.5 µl) of MuA transpososome containing gapped 42-6 transposon ends with gap and in vitro transposition reaction time (1.5 min).

FIG. 10A-8 shows an Agilent 2100 Bioanalyzer curve of fragmented *E. coli* gDNA illustrating DNA fragment length dependence on the transposon end structure assembled into MuA transpososome, amount (0.5 µl) of MuA transpososome containing gapped 42-6 transposon ends with gap and in vitro transposition reaction time (5 min).

FIG. 10A-9 shows an Agilent 2100 Bioanalyzer curve of fragmented *E. coli* gDNA illustrating DNA fragment length dependence on the transposon end structure assembled into MuA transpososome, amount (0.5 µl) of MuA transpososome containing gapped 42-6 transposon ends with gap and in vitro transposition reaction time (10 min).

FIG. 10B-1 shows an Agilent 2100 Bioanalyzer curve of fragmented *E. coli* gDNA illustrating DNA fragment length dependence on the transposon end structure assembled into MuA transpososome, amount (1.5 µl) of MuA transpososome containing native transposon ends and in vitro transposition reaction time (1.5 min).

FIG. 10B-2 shows an Agilent 2100 Bioanalyzer curve of fragmented *E. coli* gDNA illustrating DNA fragment length dependence on the transposon end structure assembled into MuA transpososome, amount (1.5 µl) of MuA transpososome containing native transposon ends and in vitro transposition reaction time (5 min).

FIG. 10B-3 shows an Agilent 2100 Bioanalyzer curve of fragmented *E. coli* gDNA illustrating DNA fragment length dependence on the transposon end structure assembled into MuA transpososome, amount (1.5 µl) of MuA transpososome containing native transposon ends and in vitro transposition reaction time (10 min).

FIG. 10B-4 shows an Agilent 2100 Bioanalyzer curve of fragmented *E. coli* gDNA illustrating DNA fragment length dependence on the transposon end structure assembled into MuA transpososome, amount (1.5 µl) of MuA transpososome containing 38-12 nicked transposon ends and in vitro transposition reaction time (1.5 min).

FIG. 10B-5 shows an Agilent 2100 Bioanalyzer curve of fragmented *E. coli* gDNA illustrating DNA fragment length dependence on the transposon end structure assembled into MuA transpososome, amount (1.5 µl) of MuA transpososome containing 38-12 nicked transposon ends and in vitro transposition reaction time (5 min).

FIG. 10B-6 shows an Agilent 2100 Bioanalyzer curve of fragmented *E. coli* gDNA illustrating DNA fragment length dependence on the transposon end structure assembled into MuA transpososome, amount (1.5 µl) of MuA transpososome containing 38-12 nicked transposon ends and in vitro transposition reaction time (10 min).

FIG. 10B-7 shows an Agilent 2100 Bioanalyzer curve of fragmented *E. coli* gDNA illustrating DNA fragment length dependence on the transposon end structure assembled into MuA transpososome, amount (1.5 µl) of MuA transpososome containing 42-6 transposon ends with gap and in vitro transposition reaction time (1.5 min).

FIG. 10B-8 shows an Agilent 2100 Bioanalyzer curve of fragmented *E. coli* gDNA illustrating DNA fragment length dependence on the transposon end structure assembled into MuA transpososome, amount (1.5 µl) of MuA transpososome containing 42-6 transposon ends with gap and in vitro transposition reaction time (5 min).

FIG. 10B-9 shows an Agilent 2100 Bioanalyzer curve of fragmented E. coli gDNA illustrating DNA fragment length dependence on the transposon end structure assembled into MuA transpososome, amount (1.5 µl) of MuA transpososome containing 42-6 transposon ends with gap and in vitro transposition reaction time (10 min).

DESCRIPTION

Figure 1:
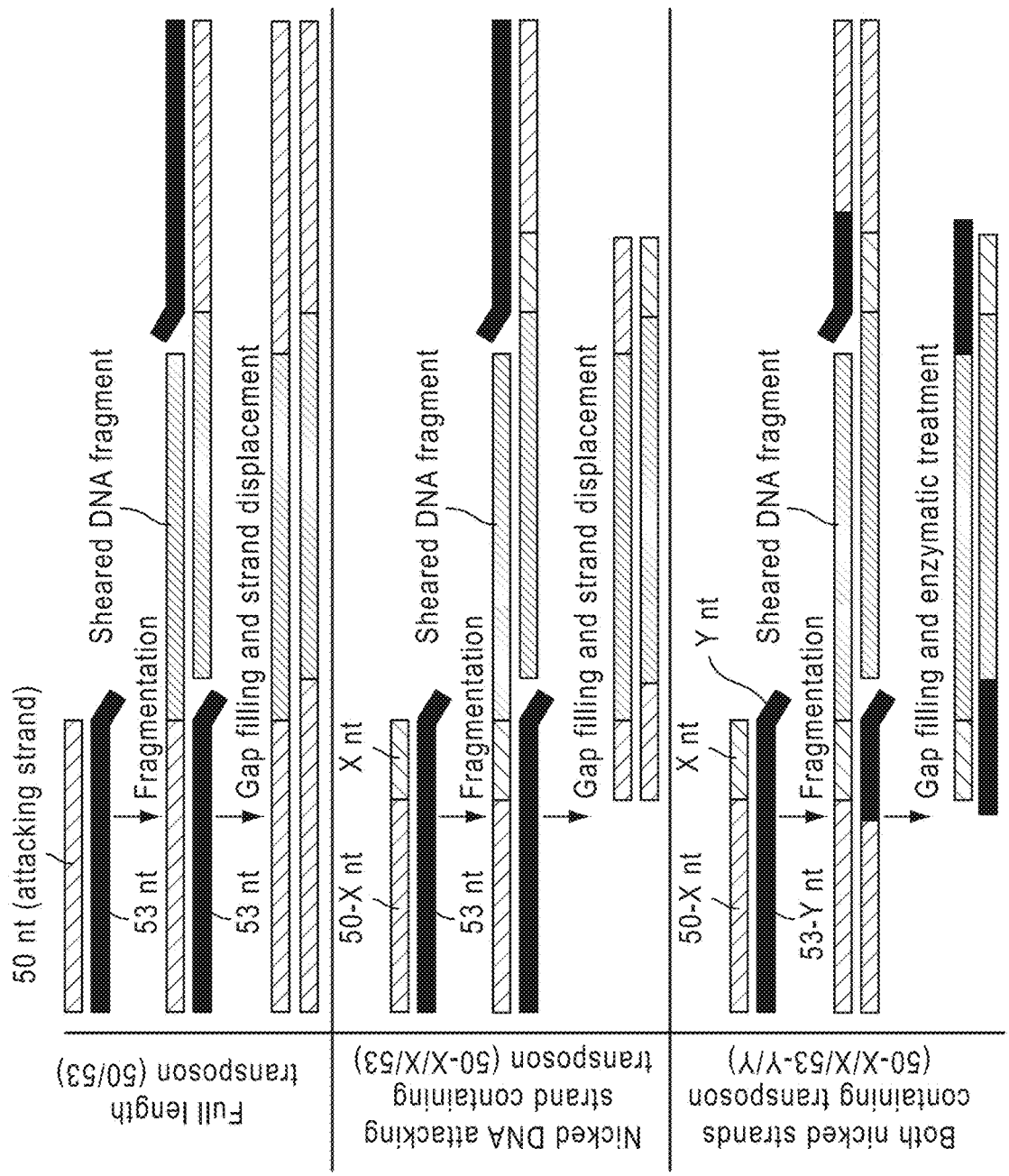
FIG. 1 shows the structure of fragmented target DNA with uniform transposon ends when a standard full length (native) transposon end, transposon end with pre-nicked attacking strand, and transposon end with both pre-nicked strands are used.
Figure 2A:
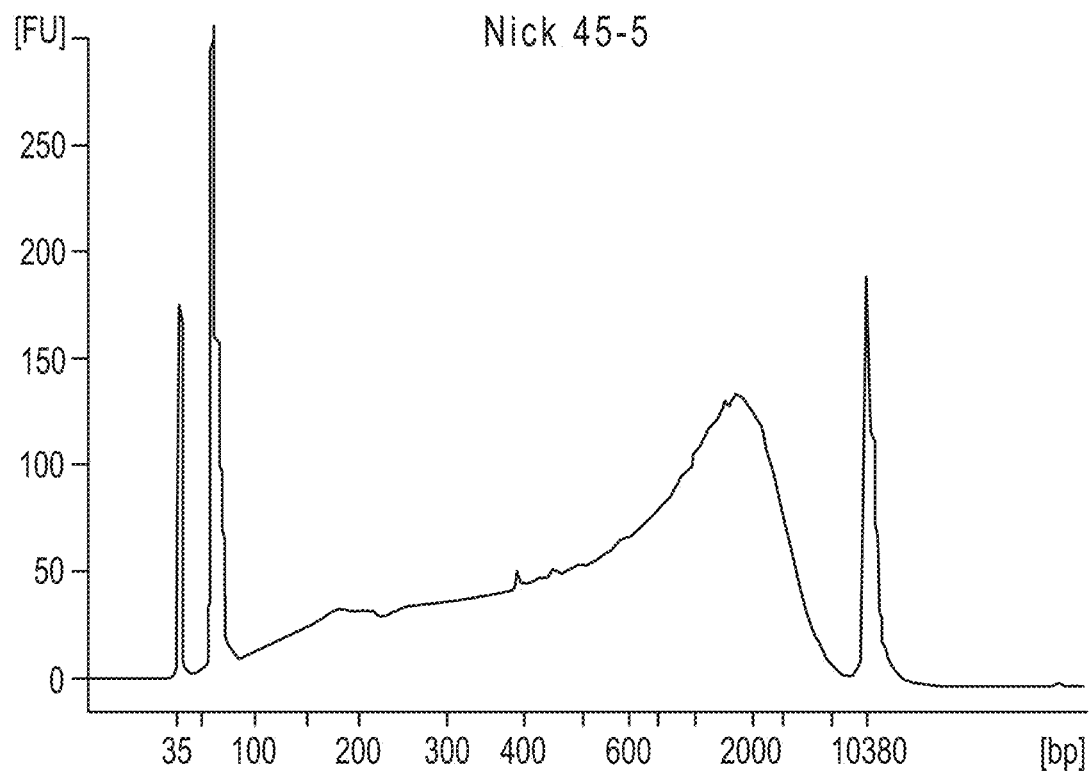
FIG. 2A shows an Agilent 2100 Bioanalyzer curve of fragmented *Escherichia coli* genomic DNA (gDNA) when pre-nicked transposon ends (45-5) were used for MuA transpososome formation and subsequent DNA fragmentation.
Figure 2B:
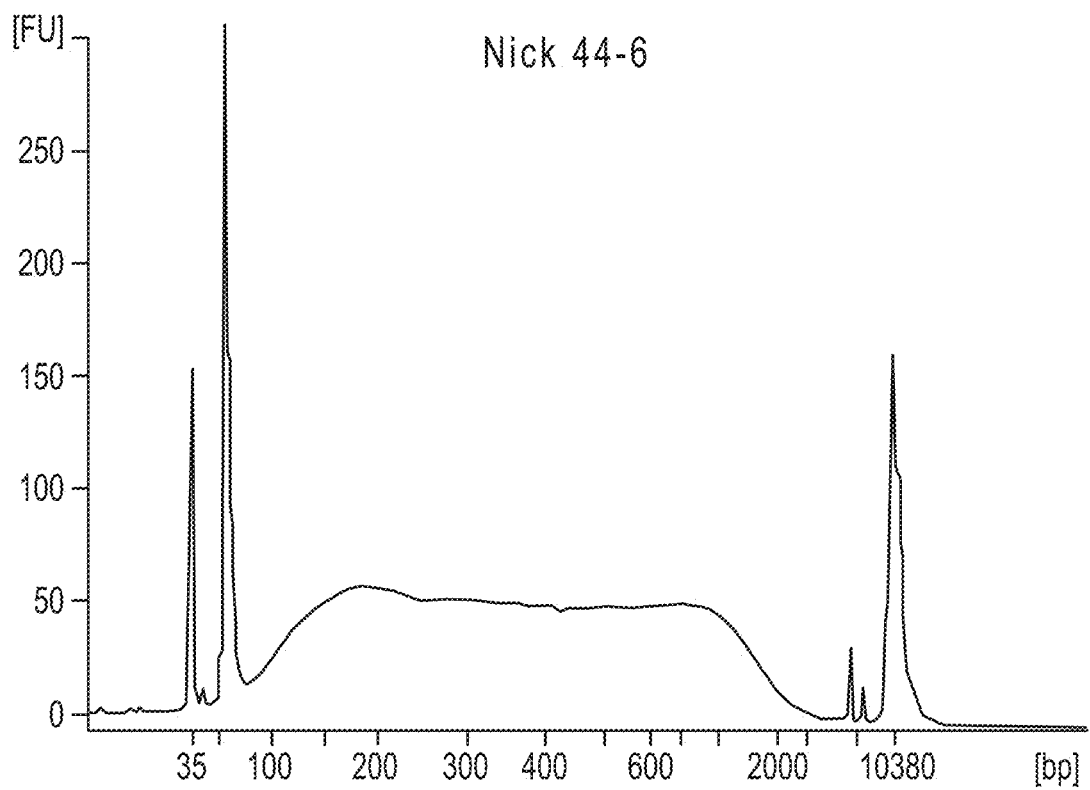
FIG. 2B shows an Agilent 2100 Bioanalyzer curve of fragmented *Escherichia coli* genomic DNA (gDNA) when pre-nicked transposon ends (44-6) were used for MuA transpososome formation and subsequent DNA fragmentation.
Figure 2C:
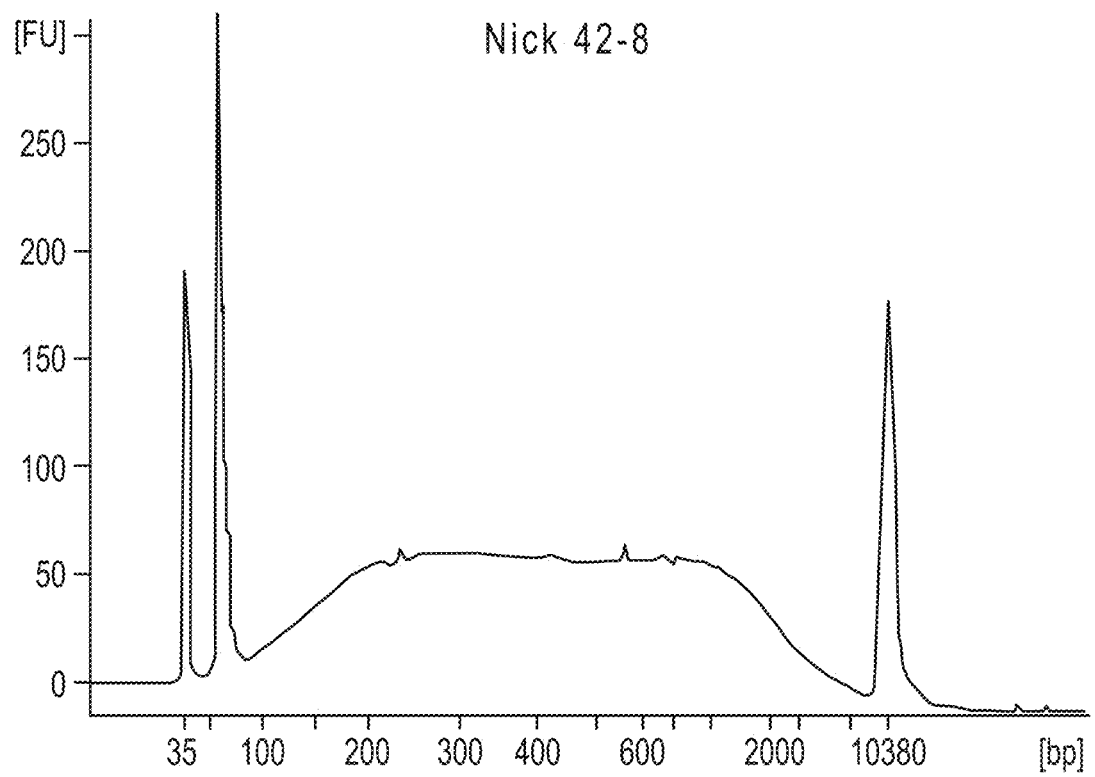
FIG. 2C shows an Agilent 2100 Bioanalyzer curve of fragmented *Escherichia coli* genomic DNA (gDNA) when pre-nicked transposon ends (42-8) were used for MuA transpososome formation and subsequent DNA fragmentation.
Figure 2D:
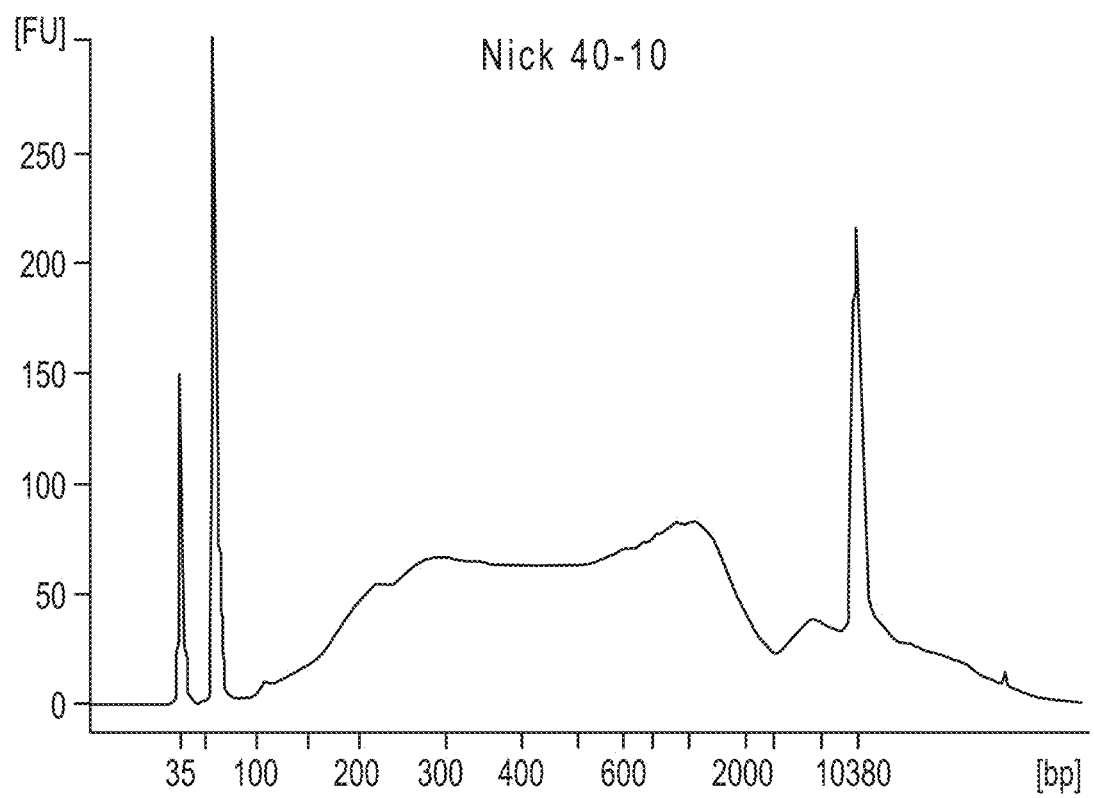
FIG. 2D shows an Agilent 2100 Bioanalyzer curve of fragmented *Escherichia coli* genomic DNA (gDNA) when pre-nicked transposon ends (40-10) were used for MuA transpososome formation and subsequent DNA fragmentation.
Figure 2E:
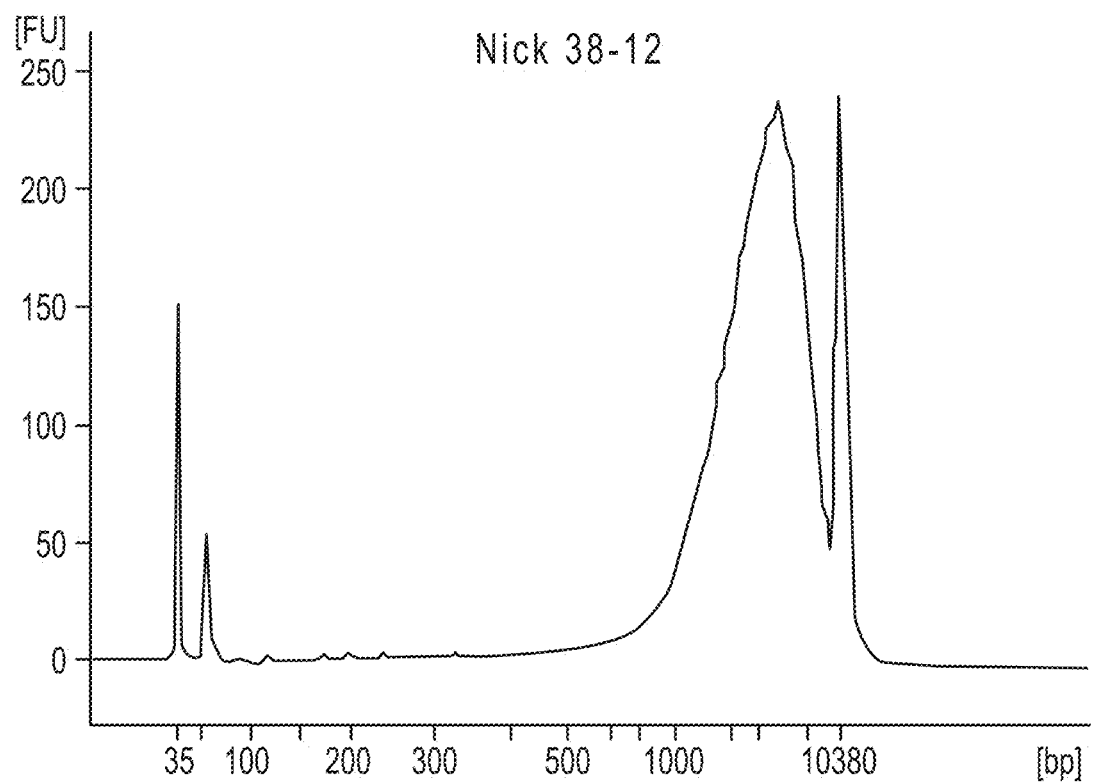
FIG. 2E shows an Agilent 2100 Bioanalyzer curve of fragmented *Escherichia coli* genomic DNA (gDNA) when pre-nicked transposon ends (38-12) were used for MuA transpososome formation and subsequent DNA fragmentation.
Figure 2F:
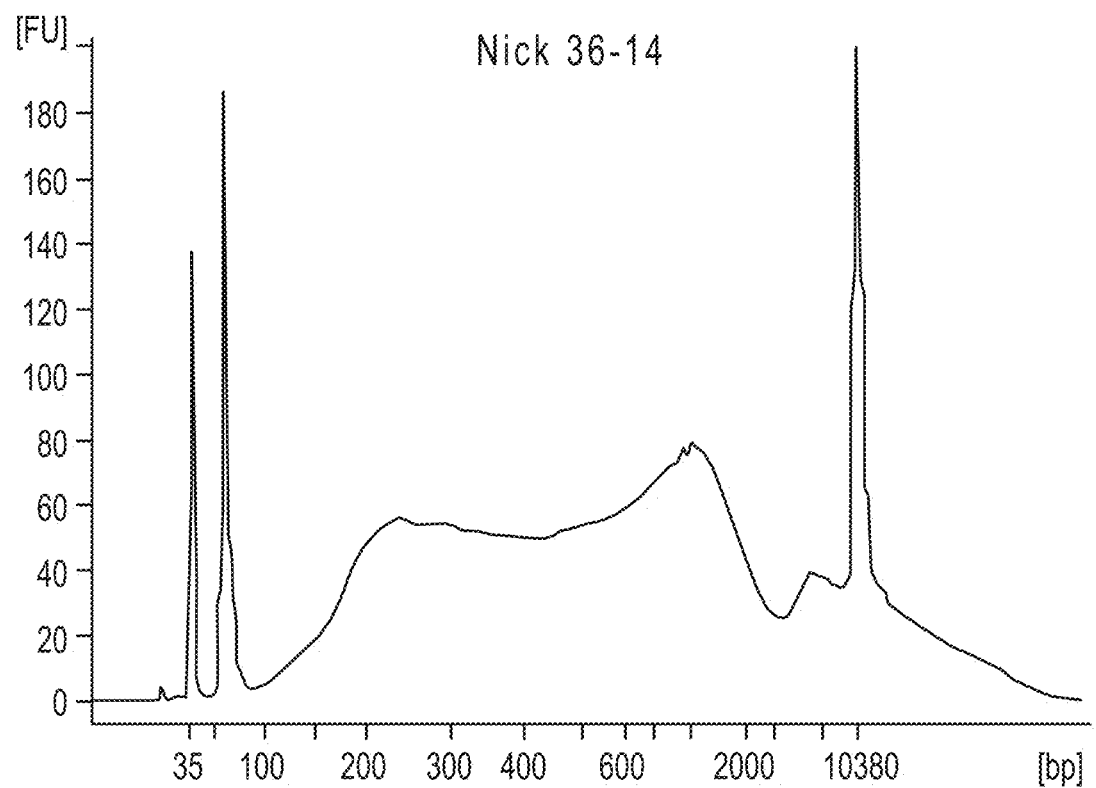
FIG. 2F shows an Agilent 2100 Bioanalyzer curve of fragmented *Escherichia coli* genomic DNA (gDNA) when pre-nicked transposon ends (36-14) were used for MuA transpososome formation and subsequent DNA fragmentation.
Figure 2G:
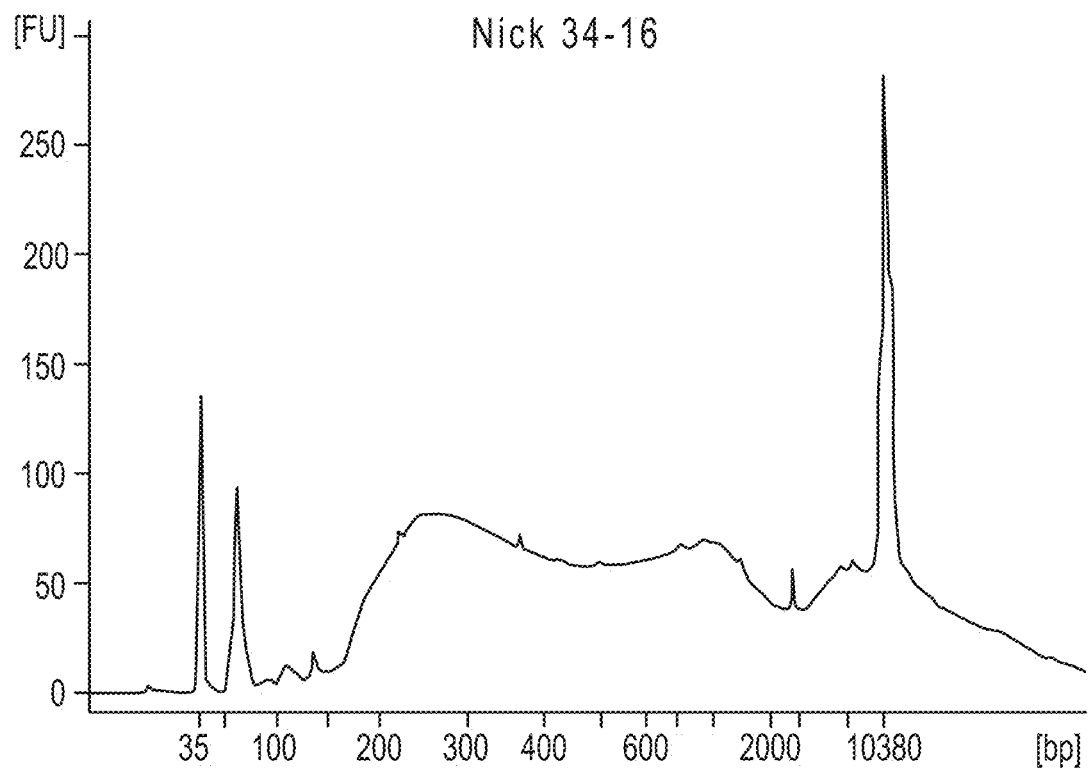
FIG. 2G shows an Agilent 2100 Bioanalyzer curve of fragmented *Escherichia coli* genomic DNA (gDNA) when pre-nicked transposon ends (34-16) were used for MuA transpososome formation and subsequent DNA fragmentation.
Figure 2H:
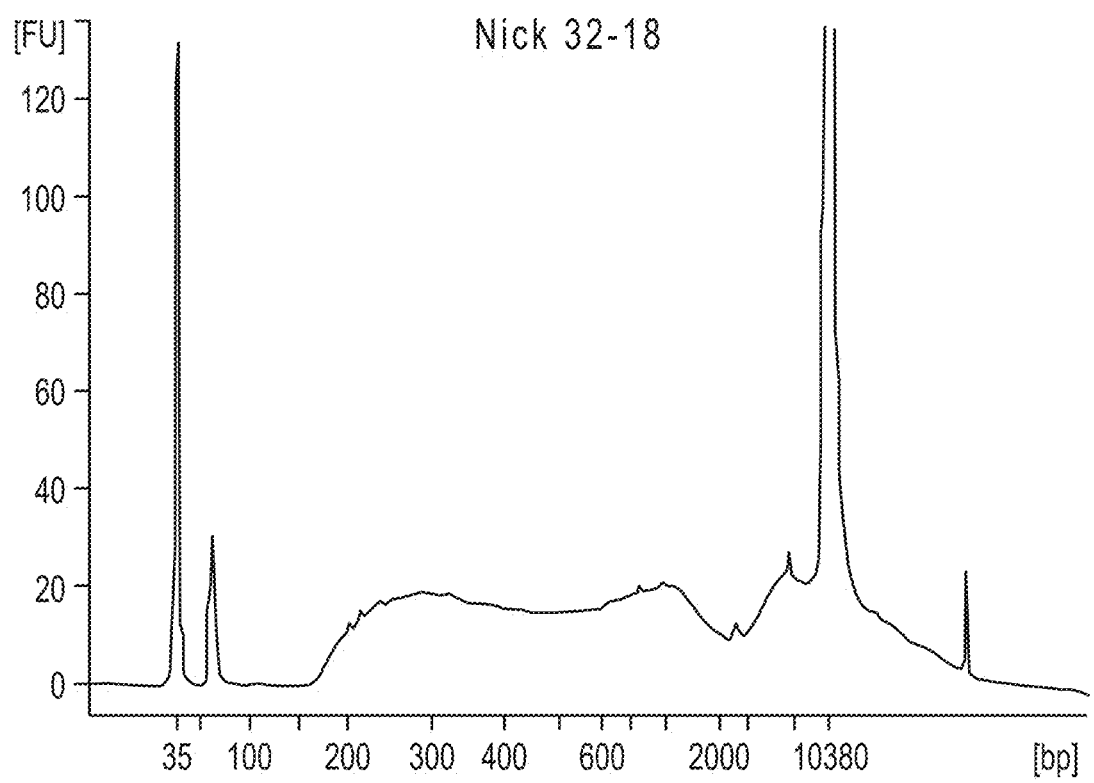
FIG. 2H shows an Agilent 2100 Bioanalyzer curve of fragmented *Escherichia coli* genomic DNA (gDNA) when pre-nicked transposon ends (32-18) were used for MuA transpososome formation and subsequent DNA fragmentation.
Figure 2I:
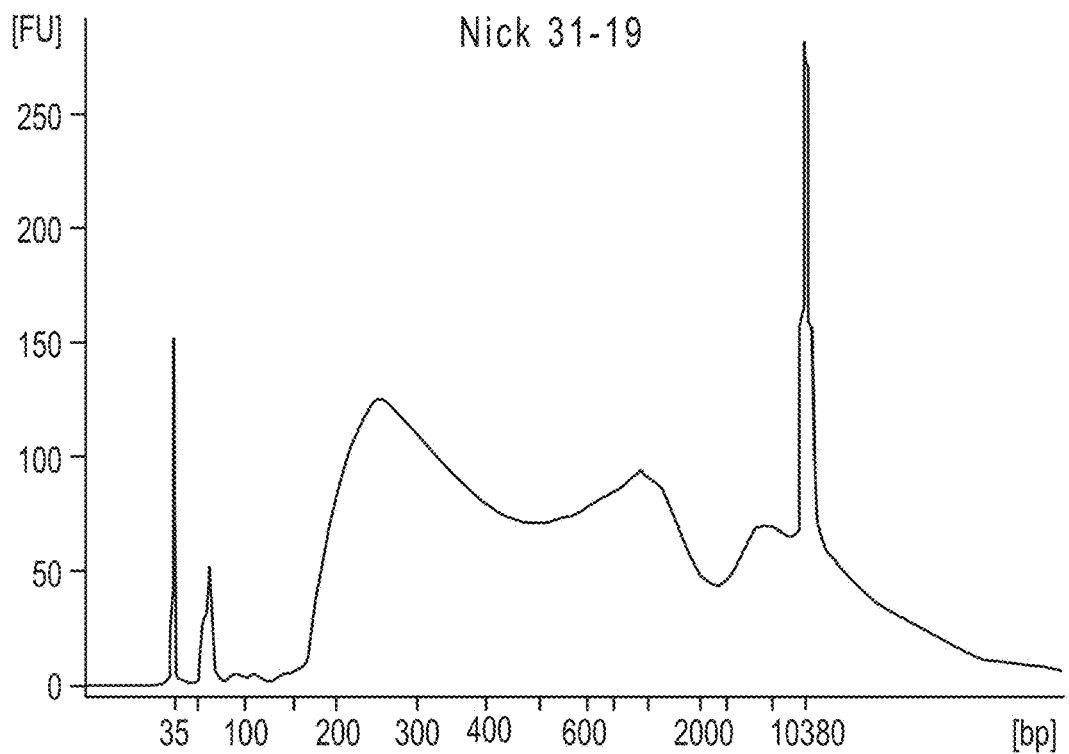
FIG. 2I shows an Agilent 2100 Bioanalyzer curve of fragmented *Escherichia coli* genomic DNA (gDNA) when pre-nicked transposon ends (31-19) were used for MuA transpososome formation and subsequent DNA fragmentation.
Figure 2J:
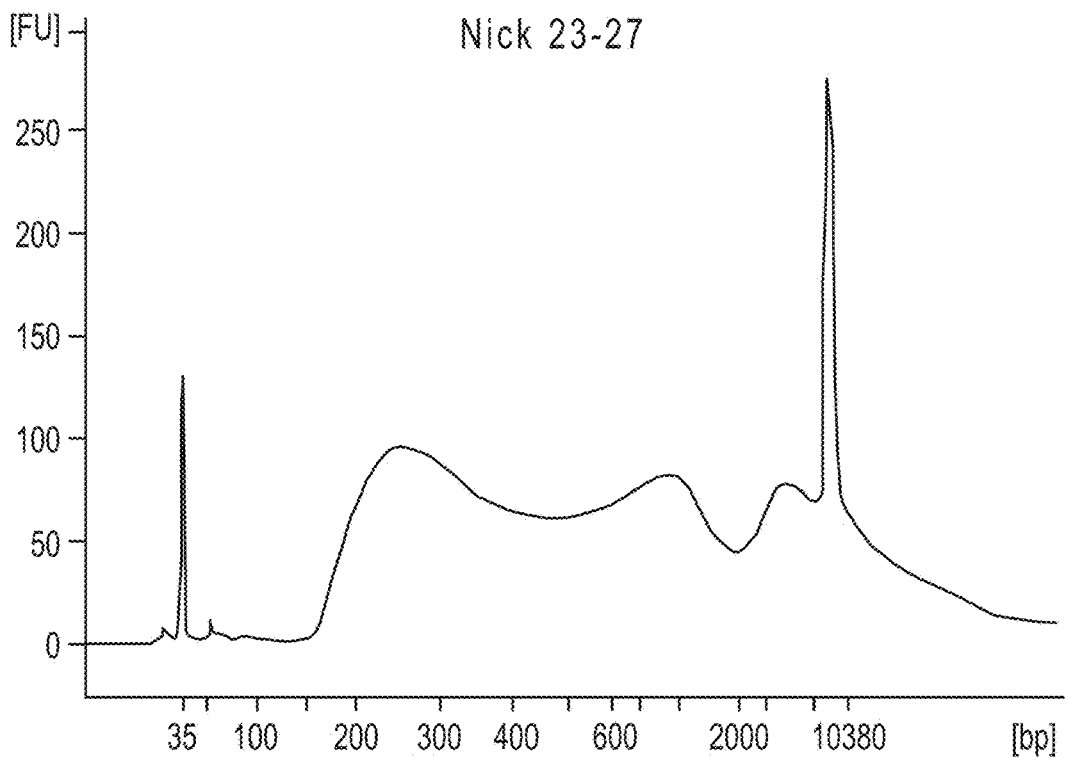
FIG. 2J shows an Agilent 2100 Bioanalyzer curve of fragmented *Escherichia coli* genomic DNA (gDNA) when pre-nicked transposon ends (23-27) were used for MuA transpososome formation and subsequent DNA fragmentation.
Figure 2K:
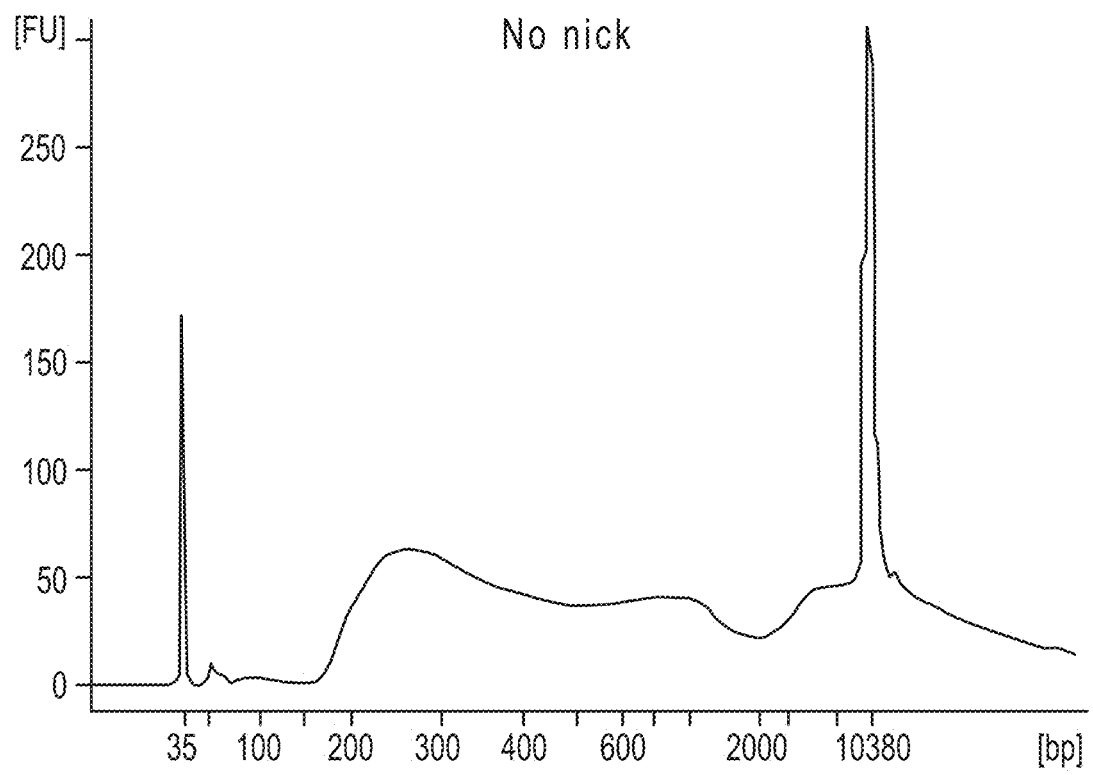
FIG. 2K shows an Agilent 2100 Bioanalyzer curve of non-fragmented *Escherichia coli* genomic DNA (gDNA).
Figure 2L:
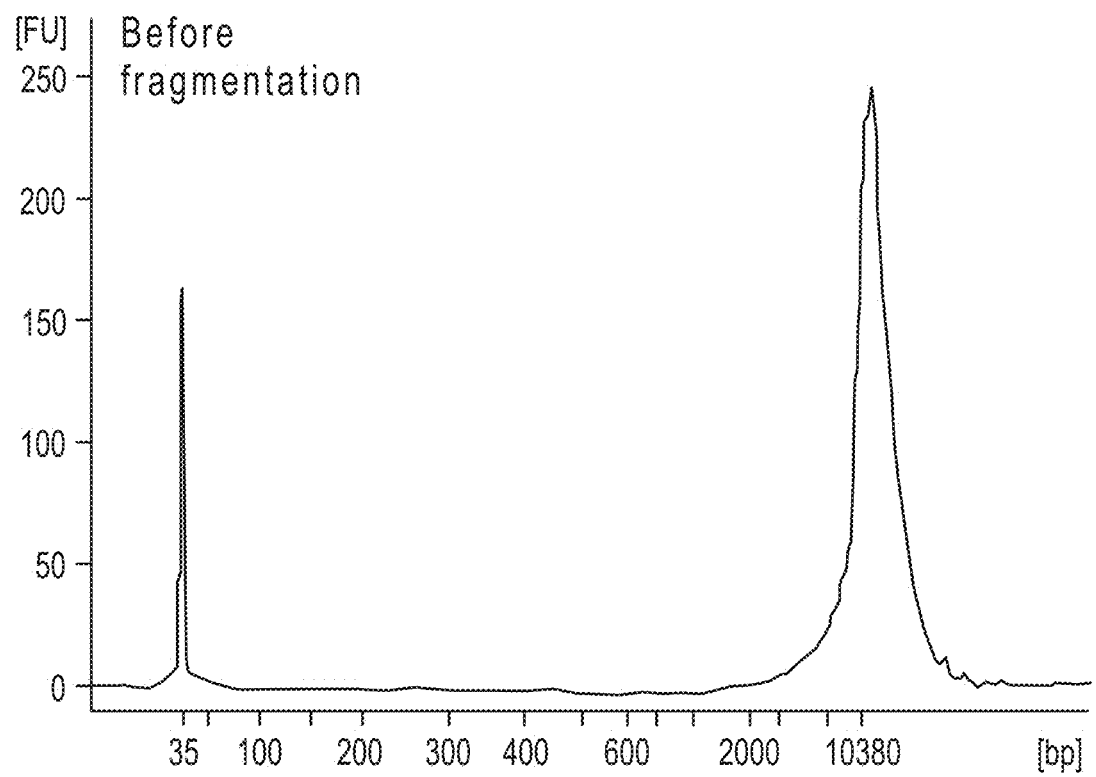
FIG. 2L shows an Agilent 2100 Bioanalyzer curve of *Escherichia coli* genomic DNA (gDNA) before fragmentation.
Figure 3A:
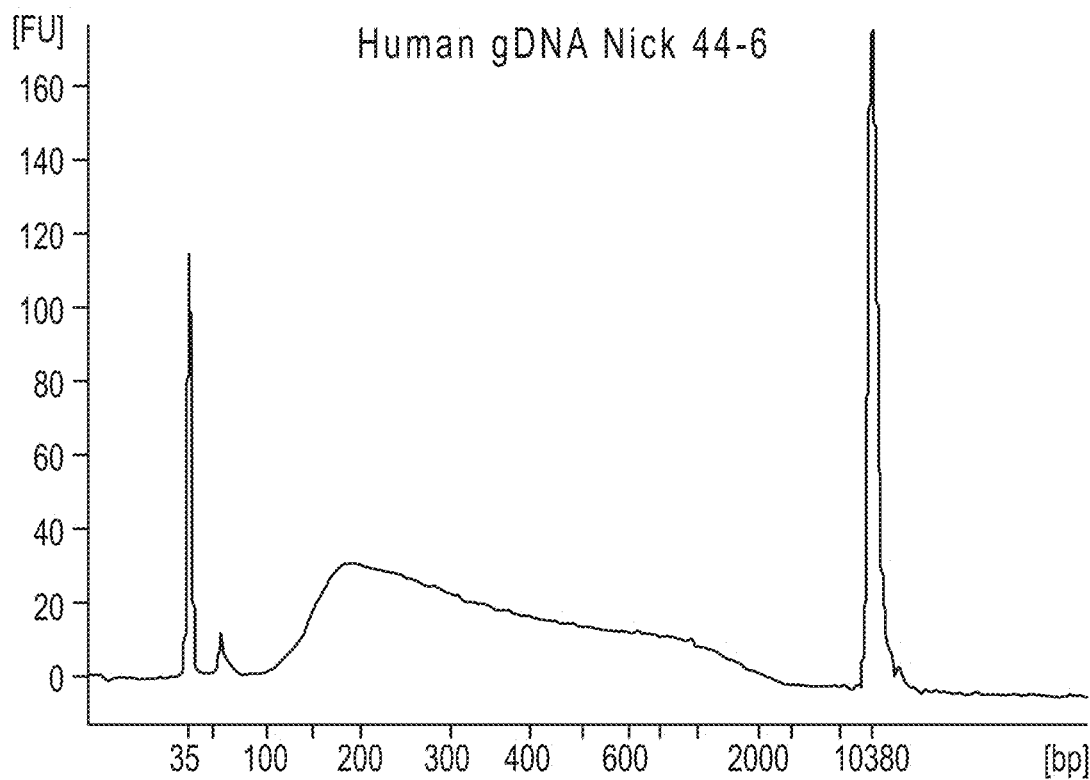
FIG. 3A shows an Agilent 2100 Bioanalyzer curve of Human gDNA fragmented using MuA-pre-nicked transposon end complex (44-6).
Figure 3B:
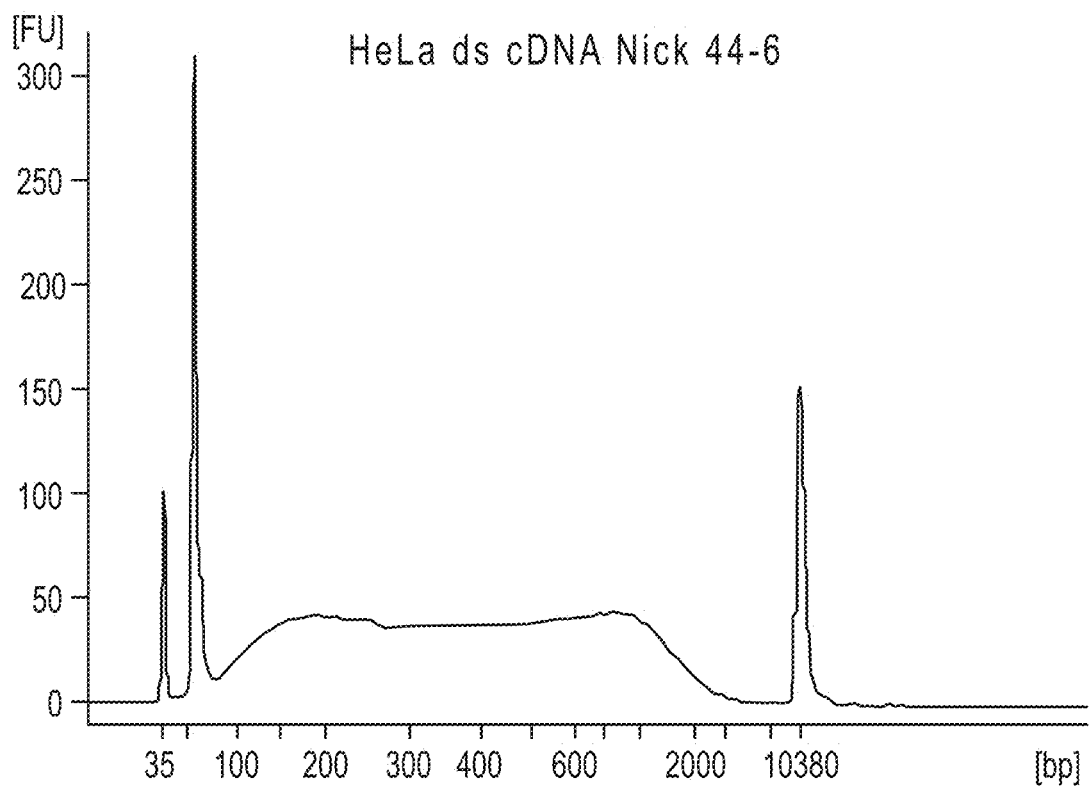
FIG. 3B shows an Agilent 2100 Bioanalyzer curve of HeLa ds cDNA fragmented using MuA-pre-nicked transposon end complex (44-6).
Figure 3C:
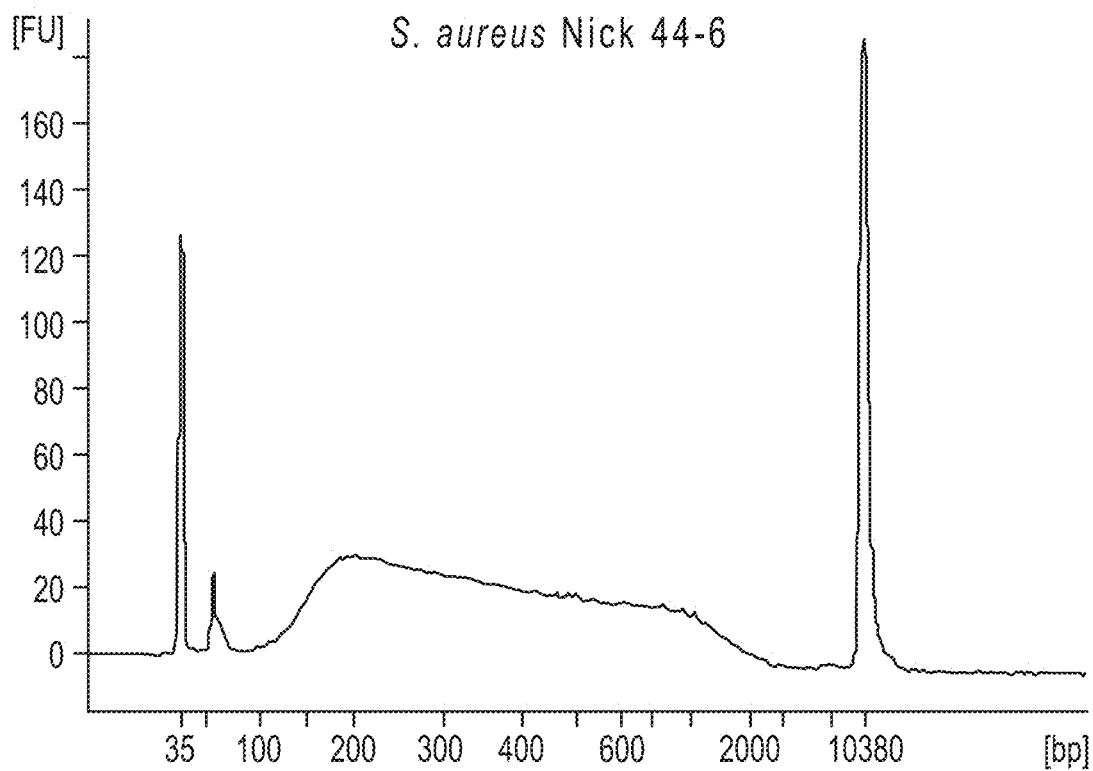
FIG. 3C shows an Agilent 2100 Bioanalyzer curve of *S. aureus* gDNA fragmented using MuA-pre-nicked transposon end complex (44-6).
Figure 3D:
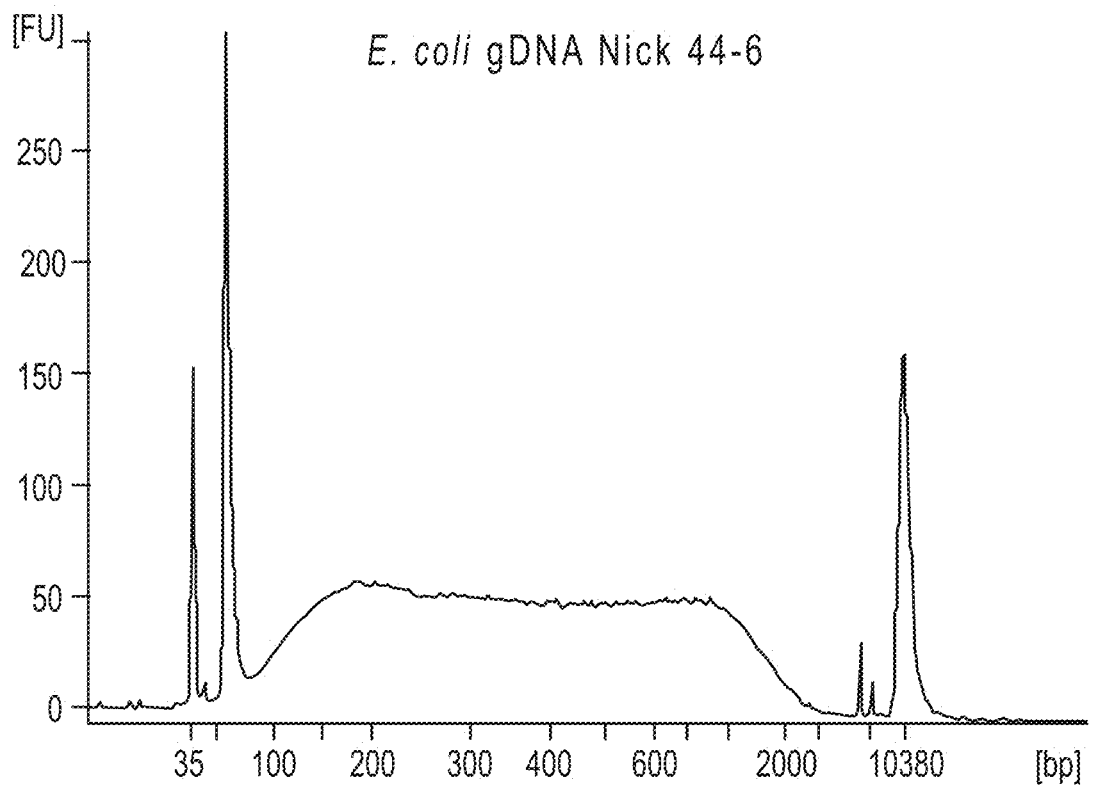
FIG. 3D shows an Agilent 2100 Bioanalyzer curve of *E. coli* gDNA fragmented using MuA-pre-nicked transposon end complex (44-6).
Figure 3E:
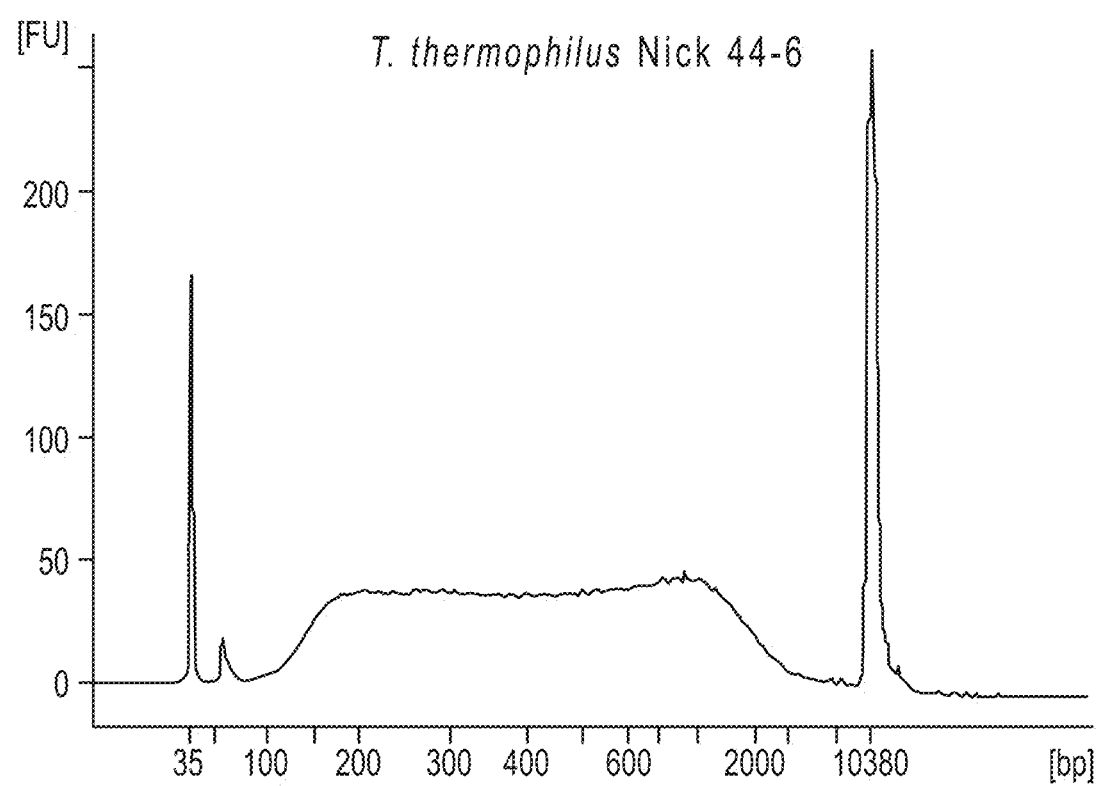
FIG. 3E shows an Agilent 2100 Bioanalyzer curve of *T. thermophilus* gDNA fragmented using MuA-pre-nicked transposon end complex (44-6).
Figure 4A:
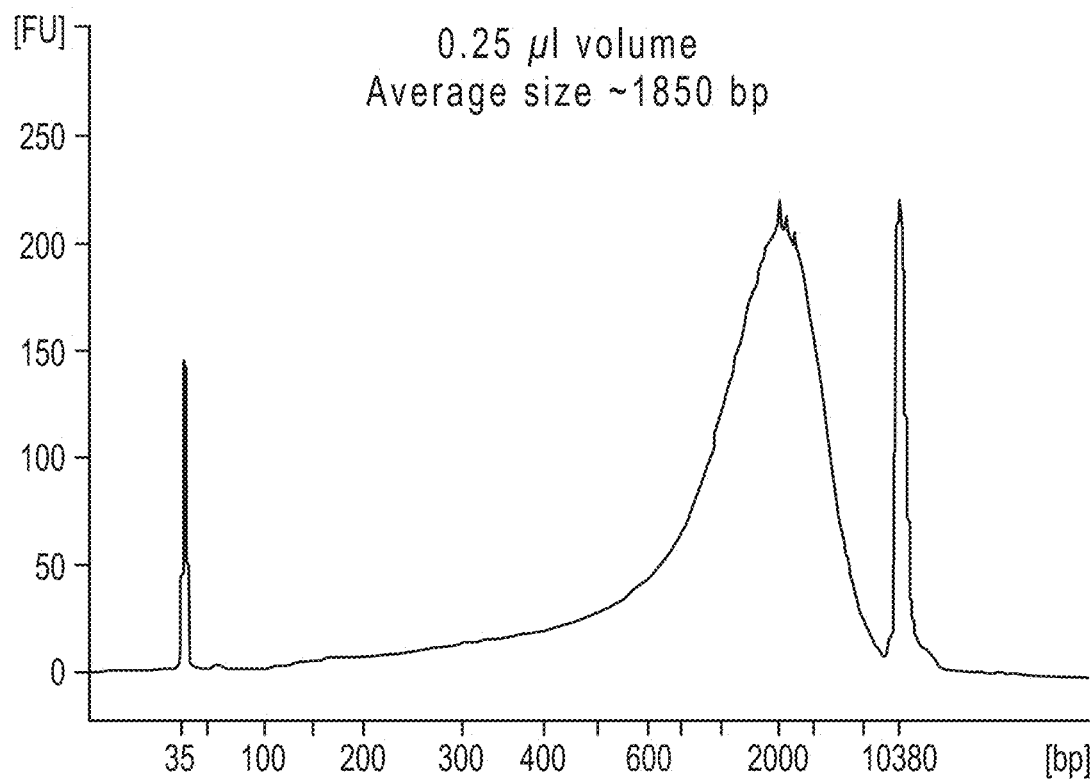
FIG. 4A shows an Agilent 2100 Bioanalyzer curves of fragmented *E. coli* gDNA which displays DNA fragment length dependence on the amount of MuA-pre-nicked transposon end complex (0.25 µl) used in the DNA fragmentation reaction.
Figure 4B:
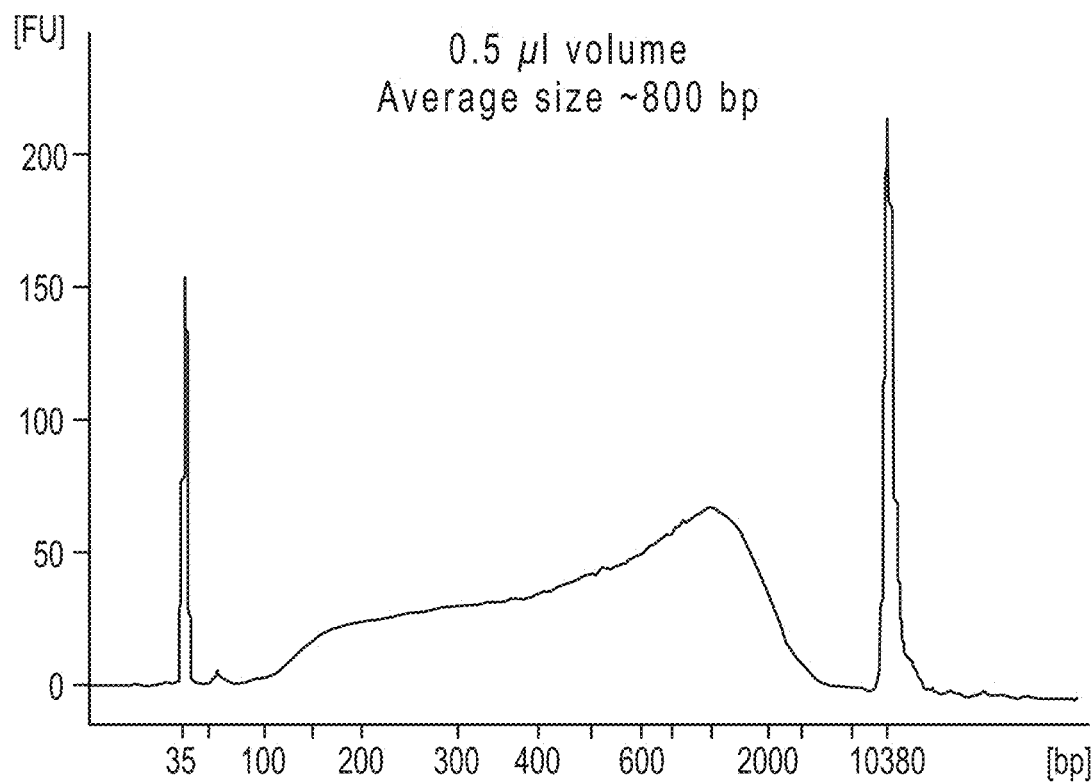
FIG. 4B shows an Agilent 2100 Bioanalyzer curve of fragmented *E. coli* gDNA which displays DNA fragment length dependence on the amount of MuA-pre-nicked transposon end complex (0.5 µl) used in the DNA fragmentation reaction.
Figure 4C:
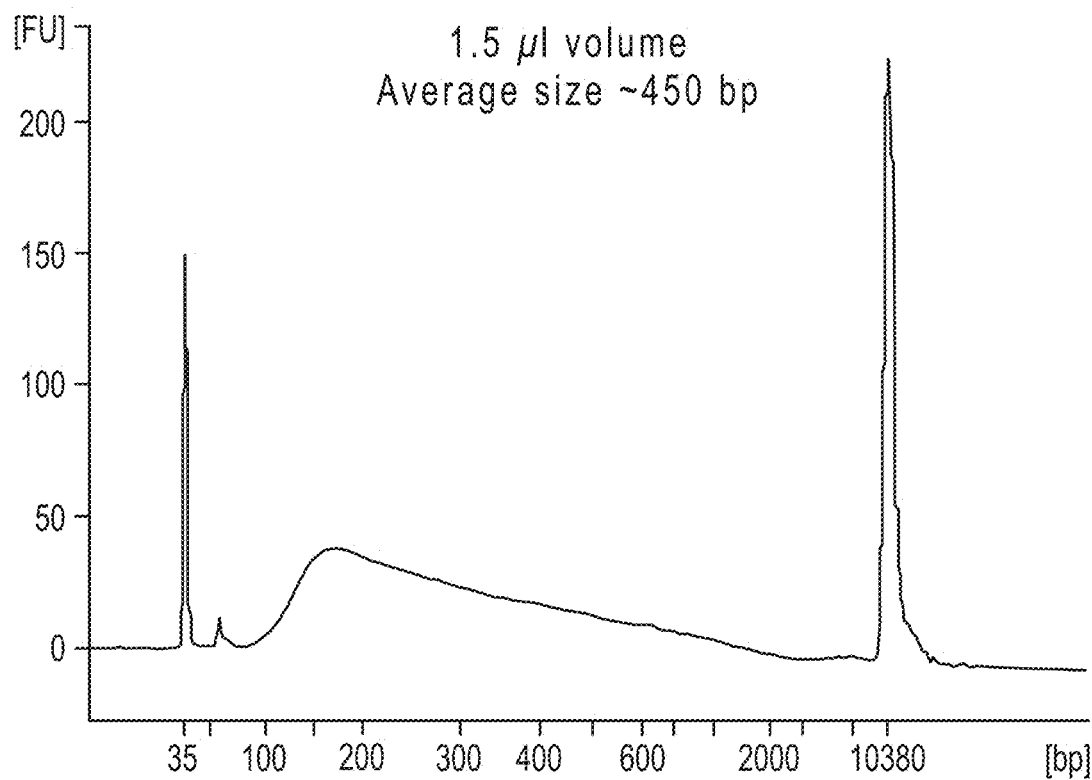
FIG. 4C shows an Agilent 2100 Bioanalyzer curve of fragmented *E. coli* gDNA which displays DNA fragment length dependence on the amount of MuA-pre-nicked transposon end complex (1.5 µl) used in the DNA fragmentation reaction.
Figure 4D:
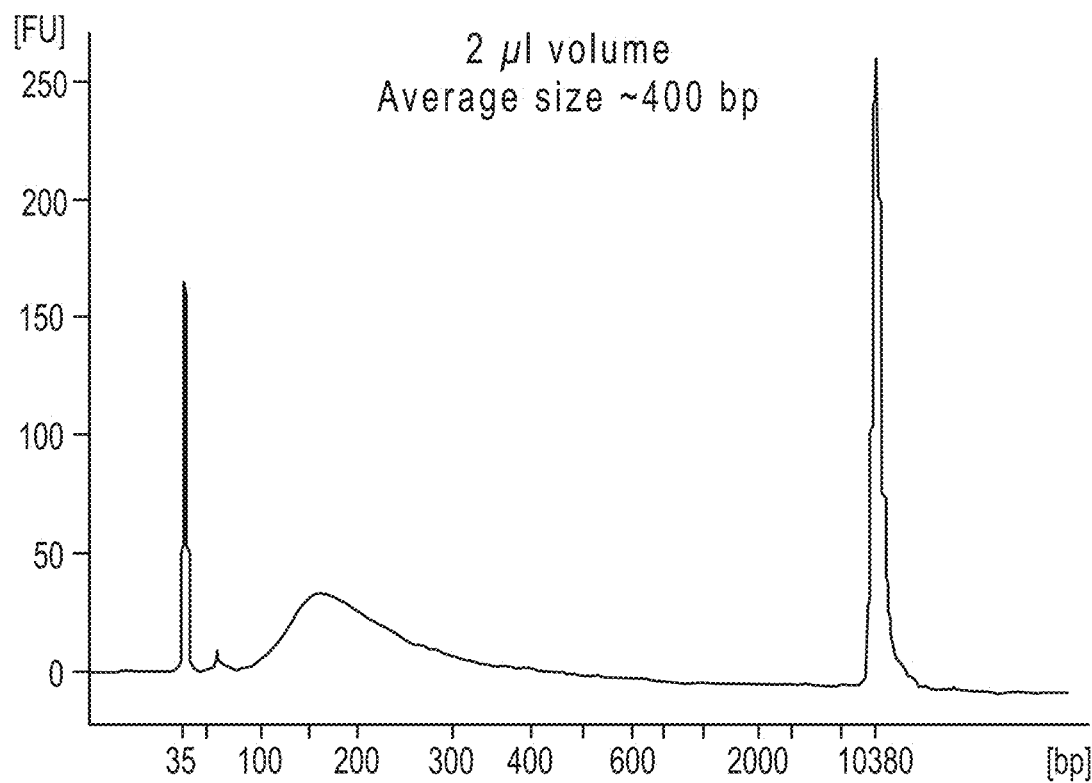
FIG. 4D shows an Agilent 2100 Bioanalyzer curve of fragmented *E. coli* gDNA which displays DNA fragment length dependence on the amount of MuA-pre-nicked transposon end complex (2 µl) used in the DNA fragmentation reaction.

The invention relates to the field of controlled fragmentation of nucleic acids.

Artificial transposons containing nicked DNA strands and their use in applications including, but not limited to, Next Generation Sequencing (NGS) library preparation.

A method for generation of nucleic acid fragments of desired length based on in vitro transposition reaction in the presence of a transposase, and a specially designed pair of transposon ends, either one or both harboring a modified sequence. A modified sequence encompasses both degenerate sequences, defined as a sequence other than wild type, and a sequence containing an artificially introduced apurinic site, apyrimidinic site, nick, or nucleotide gap, which may generally be termed an artificially introduced lesion. A transposase and a transposon end containing a modified sequence and/or modified to contain apurinic/apyrimidinic sites, nicks, or gaps are assembled into catalytically active complexes and are used to enzymatically shear a nucleic acid sample in a controlled fragmentation process that yields desired average nucleic acid fragment size. Such complexes of a transposase and a modified transposon end, when used in generation of DNA sequencing templates, offer advantages compared to currently available transposon-based DNA fragmentation kits. Such advantages include shortened stretches of transposon end sequences, ability to add specific adapters, and ability to be used in applications where production of asymmetrically tailed DNA fragments, i.e., possessing the transposed transposon end of the full length only at one end of processed DNA fragment, is preferred. The invention is further directed to transposon nucleic acids comprising a transposon DNA end sequence harboring a modified sequence.

Transposons containing modified sequences, either in an attacking strand or in both DNA strands, can be used for transposon/transposase complex formation and subsequent fragmentation of DNA of interest. As a result, transposition reaction products (sheared DNA fragments) contain uniform terminal sequences whose length and structure is anticipated by a modified transposon end sequence position in primary transposons, and which is considerably shorter compared to using full-length artificial transposons. Introduction of a modified transposon end sequence at specific positions of transposons ensures considerably higher PCR efficiency and allows formation of sticky ends of known structure that may be used for ligation with adapters carrying complementary sticky ends.

The inventive transposase-based DNA fragmenting approach is a powerful alternative to other DNA fragmentation techniques. It requires very low amounts of input DNA material. For example, the transposase-based approach described herein can be performed using about 1-25 pg, or about 25-50 pg, or about 50-100 pg, or about 100 pg-1 ng, or about 1-500 ng, or about 500-1000 ng, or about 1-10 ug, or more input DNA. In addition to DNA fragmentation, it results in specific uniform DNA sequences at both ends of the resulting DNA fragments.

In embodiments, sequences originating from transposons are used for annealing PCR primers. For a transposase-based method, uniform fragment ends are generally long enough for primer annealing, e.g., about 10 nt-25 nt, if PCR is intended to be used for amplification of reaction products. Longer complementary ends of resulting fragments lead to formation of very stable secondary DNA structures, known as "stem-loops", which prevent primer annealing and drastically inhibit PCR efficiency. When full length transposons are used, terminal complimentary ends are 50 bp long and thus require special conditions for subsequent gap-filling and strand displacement steps to ensure sufficiently high PCR efficiency.

Such drawbacks are solved using transposons with internal modified sequences in attacking DNA strands, leading to the formation of complementary ends of optimal length. Depending on experimental conditions, these complimentary ends may vary from a few to several tens of nucleotides, based upon the introduction of modified sequences into appropriate positions of transposons used for DNA shearing. For example, in PCR assisted adaptor addition reactions, longer fragments are preferred over shorter fragments when DNA was sheared with transposons containing modified sequences or lesions, which provided an advantage when recently developed 400 bp or longer sequencing protocols are further applied. However, if ligation is intended to be used for adding specific adapters, transposons for DNA fragmentation should have modified sequences either in the attacking or in both transposon strands. The latter modification of transposons results in the appearance of sticky ends at both ends of DNA fragments which are suitable for ligation with adapters having complementary sticky ends. Products of either PCR or ligation reaction or both may be used in various assays, including but not limited to NGS and microarray analysis.

In some embodiments, the disclosure relates generally to methods, as well as related compositions, systems, kits and apparatuses, for generating tagged nucleic acid fragments using the transpososome-mediated procedures describes herein, which are simple, rapid, and offer advantages over traditional library preparation methods. A typical traditional library prep workflow require multiple steps and transfer of the nucleic acid material to different reaction vessels, which can lead to loss of nucleic acid material and therefore requires large input amounts of the initial nucleic acids. Additionally, traditional library prep workflows generate libraries with sequence biases. Also, some traditional library prep methods include a separate adaptor ligation step which increases the risk of producing chimeric sequences that are not present in the initial nucleic acid sample. By contrast, the transpososome-mediated procedures of the present teachings are conducted in a single reaction mixture, in a single reaction vessel, which does not require transfer to separate reaction vessels, using transpososome complexes to yield randomly fragmented nucleic acids that are tagged at both ends with the transposon end sequences (with or without adaptor sequences and/or barcode sequences), which obviates the need for separate fragmentation and adaptor-appending reactions. The transpososome-mediated procedures of the present teachings also requires low input amounts of target nucleic acids, requiring as little as 1-25 pg, or about 25-50 pg, or about 50-100 pg, or about 100 pg-1 ng, or about 1-500 ng, or about 500-1000 ng, or about 1-10 ug, or more input DNA (Adey and Shendure 2012 Genome Research 22:1139-1143). The transpososome-mediated procedures of the present teachings offer other advantages, including generating random nucleic acid fragments that exhibit low sequence bias, generating tagged nucleic acid fragments having overlapping portions that permit contig assembly and de novo assembly of genomic sequences, generating tagged nucleic acid fragments having enough complexity to perform whole genome sequencing analysis, and achieving coverage of a high percent of a genome with preparing and analyzing (e.g., sequencing) only one or a few libraries. The transpososome-mediated procedures of the present teachings can also generate random tagged nucleic acid fragments from small genomes (e.g., microbial and viral genomes), and can generate unbiased tagged nucleic acid fragments that represent a high percent of populations within a microbial community for metagenomic analysis and microbe identification (Marine, et al., 2011 Applied and Environmental Microbiology 77(22):8071-8079).

In some embodiments, the disclosure relates generally to methods, as well as related compositions, systems, kits and apparatuses, for fragmenting and tagging nucleic acids using a plurality of transpososome complexes, which include a plurality of transposase and a first and second transposon end sequences. The transpososome complexes are contacted/reacted with target nucleic acids (e.g., double-stranded DNA) in an in vitro reaction under conditions that are suitable for transposing the transposon end sequences into the target nucleic acids, fragmenting the target nucleic acids, and joining transposon end sequences to the fragment ends. The transpososome complexes binds random positions (or nearly random positions) along the target nucleic acid, transposes the transposon end sequences into the target nucleic acid, generates double-stranded cuts at or near the transposition sites, and joins the transposon end sequences to the fragment ends, thereby producing a plurality of tagged fragmented nucleic acids where both ends of the fragmented nucleic acids are joined/tagged to a transposon end sequence from the transpososase complexes. Optionally, the plurality of transpososome complexes comprises a plurality of homo-transpososome complexes or a mixture of hetero-transpososome complexes. In some embodiments, the transposome-mediated reaction includes contacting the target nucleic acids with a plurality of transposome-complexes having transposon end sequences with the same sequence, or with a plurality of transpososome-complexes which includes at least two transpososome-complexes having different transposon end sequences (hetero-transpososome complexes). The hetero-transpososome complexes include a mixture of 2-100 or more different transpososome complexes.

In some embodiments, the tagged fragment nucleic acids produced by the transpososome-mediated reaction can be further manipulated. For example, the tagged fragment nucleic acids can be subject to end-repair reactions. The tagged fragments can be joined to at least one adaptor sequence by PCR using tailed primers or by adaptor ligation, or one fragment end can be joined to an adaptor sequence by PCR using tailed primers and the other end can be joined to an adaptor sequence using ligation (Gorbacheva, et al., 2015 BioTechniques 58:200-202). The adaptor sequence can include one or more universal sequences, including a universal amplification primer sequence, a universal sequencing primer sequence. The adaptor sequence can include at least one barcode sequence. The barcode sequence can be unique to individual tagged fragments, or can be unique to multiple tagged fragments in a plurality of tagged nucleic acid molecules (e.g. sample-specific barcode). Optionally, the adaptor-joined tagged fragments can be amplified to produce adaptor-joined tagged amplicons. Optionally, the adaptor-joined tagged amplicons can be sequenced to produce a plurality of sequencing reads. The adaptor-joined tagged amplicons can be sequenced using a massively parallel sequencing method or a gel electrophoresis sequencing method. The adaptor-joined tagged amplicons that are sequenced using a massively parallel sequencing method can be sequenced at a low, medium or high depth. Optionally, the tagged fragment nucleic acids or the adaptor-joined tagged amplicons are analyzed by hybridizing to a labeled or un-labeled nucleic acid capture primer that is attached to a support for microarray analysis.

In some embodiments, sequencing reads having overlapping sequences at their ends can be assembled to generate contigs.

In some embodiments, the sequencing reads can be analyzed to identify variant and non-variant sequences. Optionally, the sequencing reads can be quantified to determine the number and/or ratio of variant and/or non-variant sequences that are present in a single initial nucleic acid sample or between two or more different initial nucleic acid samples. When the initial nucleic acid sample is an RNA sample, then quantifying the variant and/or non-variant sequences can be used to determine the level of steady state RNA transcripts of at least one target sequence that is present in one or more initial nucleic acid samples for RNA transcript analysis. When the initial nucleic acid sample is a DNA sample, then quantifying the variant and/or non-variant sequences can be used to detect a single nucleotide variation (SNV), aneuploidy, including monosomy, trisomy, tetrasomy, and other orders of copy number variation (CNV), of a target sequence in one or more initial nucleic acid samples.

In some embodiments, the sequencing reads can be used to identify pathogen outbreaks in food, water, soil, hospitals, or identify a bio-hazard threat. The identification of these pathogens is useful for screening, inspection, diagnosis, and/or quarantine determination.

In some embodiments, the sequencing reads can be used for human identification purposes.

In some embodiments, the disclosure relates generally to methods, as well as related compositions, systems, kits and apparatuses, for aligning one or more sequencing reads to at least one reference sequence. The reference sequence can include at least a portion of: a genomic sequence, a consensus sequence, a spliced RNA sequence, a non-spliced RNA sequence, a variant sequence, non-variant sequence, a naturally-occurring sequence, or a non-naturally occurring sequence. The reference sequence can include exons, introns, exon-intron splice junctions, and DNA or RNA fusion junction sequences. Optionally, base positions of the sequencing read can be compared to base positions in the reference sequence. The sequencing reads may have 100% sequence identity with the reference sequence, or may have about 50%, or about 60%, or about 70%, or about 80%, or about 90%, or about 95%, or about 99% sequence identity with the reference sequence. Optionally, the sequence reads have perfect or imperfect alignment with their respective reference sequence. Optionally, the sequence reads have one or more mutations that result in imperfect alignment with the reference sequence. For example, at least one sequence read includes one or more mutations comprising one or more point mutations, deletions, insertions, or substitutions of one or more nucleotides, inversions, rearrangements, fusions, truncations, transversions, transitions, non-sense mutations, translocations, duplications, sequence repeats, fusion sequences, single nucleotide polymorphism (SNP), copy number variation (CNV) and/or variant or abnormal splice junction sequences.

In some embodiments, the disclosure relates generally to methods, as well as related compositions, systems, kits and apparatuses, for quantifying or otherwise estimating the number of sequencing reads that correspond to a target DNA sequence of interest, or corresponds to a target RNA transcript of interest, in one or more initial nucleic acid samples. Optionally, the quantified number of sequencing reads that correspond to a give target sequence of interest that are contained within a single initial nucleic acid sample, or are contained in two or more initial nucleic acid samples, can be compared.

In some embodiments, the quantifying includes analysis of sequencing reads from two or more initial nucleic acid samples. In some embodiments, the quantifying includes counting or estimating the number of sequencing reads that correspond to a first target sequence of interest from a first initial nucleic acid sample to obtain a first number, and counting or estimating the number of sequencing reads that correspond to a second target sequence of interest from a second initial nucleic acid sample to obtain a second number. In some embodiments, the methods further include using the first number to estimate the level of representation of the first target sequence of interest within the first initial nucleic acid sample, and using the second number to estimate the level of representation of the second target sequence of interest within the second initial nucleic acid sample. In some embodiments, the methods further include estimating the number of first polynucleotides (e.g., DNA or RNA polynucleotides) containing of the first target sequence of interest within the first initial nucleic acid sample using the first number, and estimating the number of second polynucleotides (e.g., DNA or RNA polynucleotides) containing of the second target sequence of interest within the second initial nucleic acid sample using the second number.

In some embodiments, the quantifying includes analysis of sequencing reads from a two or more different initial nucleic acid samples. In some embodiments, the disclosure relates generally to methods, as well as related compositions, systems, kits and apparatuses, for fragmenting nucleic acids (e.g., RNA or genomic DNA) from an initial nucleic acid sample in an in vitro reaction, comprising: (a) providing a plurality of transpososome complexes, which include (i) a plurality of transposases, (ii) a first transposon end sequence, wherein the first transposon end sequence is capable of binding to a transposase from the plurality of transposases and wherein the first transposon end sequence contains at least one nick, gap, apurinic site or apyrimidinic site, (iii) a second transposon end sequence, wherein the second transposon end sequence is capable of binding to a transposase from the plurality of transposases and wherein the second transposon end sequence contains at least one nick, gap, apurinic site or apyrimidinic site; (b) contacting, in a single reaction mixture, the plurality of transpososome complexes with the nucleic acids, under conditions that are suitable for transposing the first and second transposon end sequences into the genomic DNA and fragmenting the genomic DNA; and (c) producing at least one fragmented tagged DNA molecule having a first end joined to the first transposon end sequence and a second end joined to the second transposon end sequence, by transposing the first transposon end sequences into the genomic DNA at a first position and fragmenting and tagging the genomic DNA, and by transposing the second transposon end sequences into the same genomic DNA at a second position (e.g., at a different position) and fragmenting and tagging the genomic DNA, wherein the at least one fragmented tagged DNA molecules includes the first transposon end sequence having at least one nick, gap, apurinic site or apyrimidinic site, and a second end having at least one nick, gap, apurinic site or apyrimidinic site. Optionally, the fragmented tagged DNA molecule, which is joined at both ends to a transposon end sequence, can be further manipulated by appending at least one universal adaptor sequence using PCR with tailed primers or using adaptor ligation. The universal adaptor sequence may include any one or any combination of an amplification primer sequence, a sequencing primer sequence and/or a barcode sequence. In some embodiments, methods, as well as related compositions, systems, kits and apparatuses, further comprise (d) amplifying the at least one fragmented tagged DNA molecule to generate tagged DNA amplicons. In some embodiments, methods, as well as related compositions, systems, kits and apparatuses, further comprise (e) sequencing the tagged DNA amplicons. In some embodiments, two or more initial nucleic acid samples can be fragmented and tagged, in separate in vitro reactions, using the plurality of transpososome complexes described in the present teachings. Optionally, the sequencing data obtained from the two or more initial nucleic acid sample can be counted and compared. Optionally, the plurality of transpososome complexes comprises mixture of hetero-transpososome complexes.

In some embodiments, the disclosure relates generally to methods, as well as related compositions, systems, kits and apparatuses, for determining the amount of the first target polynucleotide in the first initial nucleic acid sample and the amount of the second target polynucleotide present in the second initial nucleic acid sample by comparing the first number and the second number. In some embodiments, the methods can include inferring or determining the amount of the first polynucleotide sequence in the first initial nucleic acid sample, and the amount of the second polynucleotide sequence in the second initial nucleic acid sample. In some embodiments, the method further comprises calculating a ratio of the first number relative to the second number. Optionally, the ratio can be used to infer aneuploidy or copy number of a target polynucleotide in an initial nucleic acid sample. For example, when the calculated ratio of the first polynucleotide to the second polynucleotide is approximately 1, then the first and second initial nucleic acid samples contain approximately the same amount of first and second polynucleotides, and aneuploidy is not present in the first or second initial nucleic acid sample. When the calculated ratio of the first polynucleotide to the second polynucleotide is approximately 1.5, then the first initial nucleic acid sample may contain an extra copy, such as about 3 copies, of the first polynucleotide, and the second initial nucleic acid sample contains about 2 copies of the second polynucleotide. Based on the calculated ratio of 1.5, when the first and second initial nucleic acid samples are derived from a diploid organism, then the first initial nucleic acid sample is trisomic with respect to the first polynucleotide compared to the second initial nucleic acid sample. When the calculated ratio of the first polynucleotide to the second polynucleotide is approximately 0.5, then the first initial nucleic acid sample contains about 1 copy of the first polynucleotide and the second initial nucleic acid sample contains about 2 copies of the second polynucleotide. Then the first initial nucleic acid sample may be monosomic with respect to the first polynucleotide compared to the second initial nucleic acid sample. One skilled in the art will appreciate that more than two initial nucleic acid samples can be compared in this manner.

In some embodiments, the quantifying includes analysis of sequencing reads from a single initial nucleic acid sample. In some embodiments, the disclosure relates generally to methods, as well as related compositions, systems, kits and apparatuses, for fragmenting nucleic acids (e.g., RNA or genomic DNA) from a single initial nucleic acid sample in an in vitro reaction, comprising: (a) providing a plurality of transpososome complexes, which include (i) a plurality of transposases, (ii) a first transposon end sequence, wherein the first transposon end sequence is capable of binding to a transposase from the plurality of transposases and wherein the first transposon end sequence contains at least one nick, gap, apurinic site or apyrimidinic site, (iii) a second transposon end sequence, wherein the second transposon end sequence is capable of binding to a transposase from the plurality of transposases and wherein the second transposon end sequence contains at least one nick, gap, apurinic site or apyrimidinic site; (b) contacting, in a single reaction mixture, the plurality of transpososome complexes with the nucleic acids, under conditions that are suitable for transposing the first and second transposon end sequences into the genomic DNA and fragmenting the genomic DNA; and (c) producing at least one fragmented tagged DNA molecule having a first end joined to the first transposon end sequence and a second end joined to the second transposon end sequence, by transposing the first transposon end sequences into the genomic DNA at a first position and fragmenting and tagging the genomic DNA, and by transposing the second transposon end sequences into the same genomic DNA at a second position (e.g., at a different position) and fragmenting and tagging the genomic DNA, wherein the at least one fragmented tagged DNA molecules includes the first transposon end sequence having at least one nick, gap, apurinic site or apyrimidinic site, and a second end having at least one nick, gap, apurinic site or apyrimidinic site. Optionally, the plurality of transpososome complexes comprises mixture of hetero-transpososome complexes. Optionally, the fragmented tagged DNA molecule, which is joined at both ends to a transposon end sequence, can be further manipulated by appending at least one universal adaptor sequence using PCR with tailed primers or using adaptor ligation. The universal adaptor sequence may include any one or any combination of an amplification primer sequence, a sequencing primer sequence and/or a barcode sequence. In some embodiments, methods, as well as related compositions, systems, kits and apparatuses, further comprise (d) amplifying the at least one fragmented tagged DNA molecule to generate tagged DNA amplicons. In some embodiments, methods, as well as related compositions, systems, kits and apparatuses, further comprise (e) sequencing the tagged DNA amplicons. Optionally, the sequencing data obtained from the single initial nucleic acid sample can be counted and compared.

In some embodiments, the quantifying includes counting or estimating the number of sequencing reads that correspond to a first target sequence of interest from a first initial nucleic acid sample to obtain a first number, and counting or otherwise estimating the number of sequencing reads that correspond to a second target sequence of interest from the same initial nucleic acid sample to obtain a second number. In some embodiments, the disclosed methods further include using the first number to estimate the level of representation of the first target sequence of interest within the first initial nucleic acid sample, and using the second number to estimate the level of representation of the second target sequence of interest within the same initial nucleic acid sample. In some embodiments, the disclosed methods further include estimating the number of first polynucleotides (e.g., DNA or RNA polynucleotides) containing the first target sequence of interest within the first initial nucleic acid sample using the first number, and estimating the number of second polynucleotides (e.g., DNA or RNA polynucleotides) containing the second target sequence of interest within the same initial nucleic acid sample using the second number.

In some embodiments, the amount of the second target polynucleotide, present in the same initial nucleic acid sample by comparing the first and second numbers. In some embodiments, the difference between the first and second numbers can be mathematically expressed as a—fold different or as a percent difference.

In some embodiments, the disclosure relates generally to methods, as well as related, systems, compositions, kits and apparatuses, for preparing a nucleic acid library for whole genome sequencing applications using the transpososome-mediated procedures described in the present teachings. In some embodiments, the transpososome complexes are reacted with genomic DNA to generate a plurality of tagged DNA fragments that contain sequences covering thousands or up to millions of bases in the genome. The tagged DNA fragments can be further manipulated to generate a DNA library.

In some embodiments, the disclosure relates generally to methods, as well as related compositions, systems, kits and apparatuses, for fragmenting genomic DNA in an in vitro reaction, comprising: (a) providing a plurality of transpososome complexes, which include (i) a plurality of transposases, (ii) a first transposon end sequence, wherein the first transposon end sequence is capable of binding to a transposase from the plurality of transposases and wherein the first transposon end sequence contains at least one nick, gap, apurinic site or apyrimidinic site, (iii) a second transposon end sequence, wherein the second transposon end sequence is capable of binding to a transposase from the plurality of transposases and wherein the second transposon end sequence contains at least one nick, gap, apurinic site or apyrimidinic site; (b) contacting, in a single reaction mixture, the plurality of transpososome complexes with genomic DNA, under conditions that are suitable for transposing the first and second transposon end sequences into the genomic DNA and fragmenting the genomic DNA; and (c) producing at least one fragmented tagged DNA molecule having a first end joined to the first transposon end sequence and a second end joined to the second transposon end sequence, by transposing the first transposon end sequences into the genomic DNA at a first position and fragmenting and tagging the genomic DNA, and by transposing the second transposon end sequences into the same genomic DNA at a second position (e.g., at a different position) and fragmenting and tagging the genomic DNA, wherein the at least one fragmented tagged DNA molecules includes the first transposon end sequence having at least one nick, gap, apurinic site or apyrimidinic site, and a second end having at least one nick, gap, apurinic site or apyrimidinic site. Optionally, the plurality of transpososome complexes comprises mixture of hetero-transpososome complexes. Optionally, the fragmented tagged DNA molecule, which is joined at both ends to a transposon end sequence, can be further manipulated by appending at least one universal adaptor sequence using PCR with tailed primers or using adaptor ligation. The universal adaptor sequence may include any one or any combination of an amplification primer sequence, a sequencing primer sequence and/or a barcode sequence. In some embodiments, methods, as well as related compositions, systems, kits and apparatuses, further comprise (d) amplifying the at least one fragmented tagged DNA molecule to generate tagged DNA amplicons. In some embodiments, methods, as well as related compositions, systems, kits and apparatuses, further comprise (e) sequencing the tagged DNA amplicons. Optionally, the sequencing data can be used for detecting sequence variants and/or non-variants in a genome, or de novo assembly of the sequencing reads, or for microbe identity, or metagenomic analysis.

In some embodiments, the plurality of transpososome complexes includes a plurality of transpososome complexes, each containing a plurality of transposons, and first and second transposon end sequences having the same sequence. In some embodiments, the plurality of transpososome complexes includes a plurality of hetero-transpososome complexes containing at least a first and second transpososome complex, where the first and second transposon end sequences of the first transpososome complex having the same sequence, and the first and second transposon end sequences of the second transpososome complex having the same sequence but differ from the first and second transposon end sequences of the first transpososome complex. The hetero-transpososome complexes include a mixture of 2-100 or more different transpososome complexes.

In some embodiments, the genomic DNA can be isolated from any organism, including prokaryote, eukaryote, bacteria, virus or fungus. The genomic DNA can be isolated from water, soil or food. The genomic DNA can be isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs. The genomic DNA can be isolated from any biological sample including a biological fluid (e.g., blood) or solid tissue obtained by biopsy, swab, or smear. In some embodiments, the solid tissue includes healthy or diseased tissue (e.g., tumor) or biological fluid, or a mixture of healthy and diseased tissue or biological fluid.

In some embodiments, the whole genome library can be prepared from low input amounts of genomic DNA, including about 1-25 pg, or about 25-50 pg, or about 50-100 pg, or about 100 pg-1 ng, or about 1-500 ng, or about 500-1000 ng, or about 1-10 ug, or more input DNA.

In some embodiments, the disclosure relates generally to methods, as well as related compositions, systems, kits and apparatuses, for conducting epigenetic analysis of chromatin using the transpososome-mediated procedures described in the present teachings. In some embodiments, transpososome complexes can transpose into chromatin (e.g., open chromatin regions) and yield tagged chromatin fragments that retains the nucleosome structure. The tagged chromatin fragments can be used for analysis of nucleosome positioning, mapping open chromatin regions, chromatin accessibility and binding patterns of DNA-binding factors including transcription and translation factors. The tagged chromatin fragments may reveal changes in chromatin structure as part of a cellular response to a change in a condition, such as genetic mutation, onset of disease, or exposure to a chemical compound, drug, hormone or physical stress.

In some embodiments, the disclosure relates generally to methods, as well as related compositions, systems, kits and apparatuses, for fragmenting chromatin in an in vitro reaction, comprising: (a) providing a plurality of transpososome complexes, which include (i) a plurality of transposases, (ii) a first transposon end sequence, wherein the first transposon end sequence is capable of binding to a transposase from the plurality of transposases and wherein the first transposon end sequence contains at least one nick, gap, apurinic site or apyrimidinic site, (iii) a second transposon end sequence, wherein the second transposon end sequence is capable of binding to a transposase from the plurality of transposases and wherein the second transposon end sequence contains at least one nick, gap, apurinic site or apyrimidinic site; (b) contacting, in a single reaction mixture, the plurality of transpososome complexes with chromatin from a first chromatin sample, under conditions that are suitable for transposing the first and second transposon end sequences into the chromatin and fragmenting the chromatin, where the chromatin includes at least one nucleosome (e.g., having DNA and histones, and optionally DNA-binding factors); and (c) producing at least one fragmented tagged chromatin having a first end joined to the first transposon end sequence and a second end joined to the second transposon end sequence, by transposing the first transposon end sequences into a first position of the chromatin and fragmenting and tagging the chromatin, and by transposing the second transposon end sequences into a second position of the chromatin and fragmenting and tagging the chromatin, wherein the at least one fragmented tagged chromatin includes the first transposon end sequence having at least one nick, gap, apurinic site or apyrimidinic site, and a second end having at least one nick, gap, apurinic site or apyrimidinic site. Optionally, the plurality of transpososome complexes comprises mixture of hetero-transpososome complexes. Optionally, the fragmented tagged chromatin, which is joined at both ends to a transposon end sequence, can be further manipulated by appending at least one universal adaptor sequence using PCR with tailed primers or using adaptor ligation. The universal adaptor sequence may include any one or any combination of an amplification primer sequence, a sequencing primer sequence and/or a barcode sequence.

In some embodiments, methods, as well as related compositions, systems, kits and apparatuses, further comprise (d) amplifying the at least one fragmented tagged chromatin to generate amplified chromatin.

In some embodiments, methods, as well as related compositions, systems, kits and apparatuses, further comprise (e) sequencing the amplified chromatin.

In some embodiments, the plurality of transpososome complexes includes a plurality of transpososome complexes, each containing a plurality of transposons, and first and second transposon end sequences having the same sequence. In some embodiments, the plurality of transpososome complexes includes a plurality of hetero-transpososome complexes containing at least a first and second transpososome complex, where the first and second transposon end sequences of the first transpososome complex having the same sequence, and the first and second transposon end sequences of the second transpososome complex having the same sequence but differ from the first and second transposon end sequences of the first transpososome complex. The hetero-transpososome complexes include a mixture of 2-100 different transpososome complexes.

In some embodiments, chromatin from a second chromatin sample can be contacted with a plurality of transpososome complexes in a separate single reaction mixture to produce a second plurality of fragmented tagged chromatin (e.g., steps (a)-(c)) which can optionally be amplified (e.g., step (d)) and the resulting amplified tagged chromatin can optionally be sequenced (e.g., step (e)), for comparison with the sequencing data obtained from the first chromatin sample. The sequence data can be analyzed to identify changes and difference in the chromatin structure (e.g., changes between open and closed chromatin, and vice versa) between the first and second chromatin samples resulting from changes in cellular conditions. Optionally, the changes in chromatin structure that are revealed by the transpososome-mediated procedures can be compared to DNase I sensitivity analysis (Buenrostro, et al., 2013 Nature Methods 12:1213-1218; and Buenrostro, et al., 2015 Current Protocols Molecular Biology 109:21.29.1-21.29.9).

In some embodiments, the first and second chromatin samples contain closed chromatin and/or open chromatin (e.g., exposed chromatin). The first and/or second chromatin samples may include 1-10 or more nucleosomes. The first and/or second chromatin may include at least one DNA-binding factor, including a transcription and/or translation factor. The first and/or second chromatin may be isolated from an initial nucleic acid sample containing as little as about 100 pg of DNA, or about 100 pg-1 ng, or about 1 ng-1 µg, or more. The first and/or second chromatin may be isolated from a single cell, or from about 2-1000 cells, or about 1000-10,000 cells, or about 10,000-100,000 cells. The first and/or second chromatin may be isolated from cells that are normal, diseased, carry at least one mutation or genetic variant, have been subjected to starvation or limited nutrients, have been treated with a chemical compound or a drug or a hormone, or have been challenged with a chemical compound, a drug, a hormone, or a physical condition that may cause a change in chromatin structure. The physical challenge condition includes temperature changes, cold, heat, light, electric shock, acoustic energy, pressure, osmotic changes, nutrient availability, pH changes, and others.

In some embodiments, the disclosure relates generally to methods, as well as related compositions, systems, kits and apparatuses, for conducting chromatin immuno-precipitation (ChIP) analysis of interactions between DNA-binding proteins and chromatin, using the transpososome-mediated procedures described in the present teachings.

In some embodiments, the chromatin immuno-precipitation workflow generally includes cross-linking the chromatin to DNA-binding proteins that are bound to the chromatin, fragmenting and tagging the cross-linked chromatin using a plurality of transpososome complexes, and immuno-precipitating at least some of the tagged cross-linked chromatin fragments with an antibody that specifically binds a target DNA-binding protein that is cross-linked to the tagged chromatin fragment. The tagged, immuno-precipitated cross-linked chromatin fragments can be used for analysis of changes in DNA-binding protein patterns that may play a role in cellular processes, including DNA replication, cell cycle regulation (e.g., mitosis and meiosis), recombination, segregation, transcription regulation, repair, translation regulation, chromosomal stability and epigenetic silencing.

In some embodiments, the disclosure relates generally to methods, as well as related compositions, systems, kits and apparatuses, for preparing immuno-precipitated chromatin fragments in an in vitro reaction, comprising: (a) providing a plurality of transpososome complexes, which include (i) a plurality of transposases, (ii) a first transposon end sequence, wherein the first transposon end sequence is capable of binding to a transposase from the plurality of transposases and wherein the first transposon end sequence contains at least one nick, gap, apurinic site or apyrimidinic site, (iii) a second transposon end sequence, wherein the second transposon end sequence is capable of binding to a transposase from the plurality of transposases and wherein the second transposon end sequence contains at least one nick, gap, apurinic site or apyrimidinic site; (b) providing a first chromatin sample that is cross-linked to at least one target DNA-binding protein by subjecting chromatin in a first plurality of cells to a cross-linking agent (e.g., formaldehyde or ultra-violet light) under conditions suitable for cross-linking the least one target DNA-binding protein to the chromatin, and extracting the cross-linked chromatin from the first plurality of cells, where the chromatin in the first plurality of cells includes at least one target DNA-binding protein bound to the chromatin, and where the cross-linking is optionally irreversible; (c) contacting the plurality of transpososome complexes with the cross-linked chromatin from the first chromatin sample, in a single reaction mixture, under conditions that are suitable for transposing the first and second transposon end sequences into the cross-linked chromatin and fragmenting the chromatin; (d) producing at least one fragmented tagged cross-linked chromatin having a first end joined to the first transposon end sequence and a second end joined to the second transposon end sequence, by transposing the first transposon end sequences into a first position of the cross-linked chromatin and fragmenting and tagging the cross-linked chromatin, and by transposing the second transposon end sequences into a second position of the cross-linked chromatin and fragmenting and tagging the cross-linked chromatin, wherein the at least one fragmented cross-linked chromatin includes the first transposon end sequence having at least one nick, gap, apurinic site or apyrimidinic site, and a second end having at least one nick, gap, apurinic site or apyrimidinic site. Optionally, the plurality of transpososome complexes comprises mixture of hetero-transpososome complexes. Optionally, the fragmented tagged cross-linked chromatin, which is joined at both ends to a transposon end sequence, can be further manipulated by appending at least one universal adaptor sequence using PCR with tailed primers or using adaptor ligation. The universal adaptor sequence may include any one or any combination of an amplification primer sequence, a sequencing primer sequence and/or a barcode sequence. In some embodiments, the first plurality of cells is treated under a first condition that may cause a change in chromatin binding pattern of the target DNA-binding protein.

In some embodiments, methods, as well as related compositions, systems, kits and apparatuses, further comprise (e) immuno-precipitating the fragmented tagged cross-linked chromatin by contacting the fragmented tagged cross-linked chromatin with an antibody that specifically binds the target DNA-binding protein, where the antibody is optionally attached to a paramagnetic particle or bead.

In some embodiments, methods, as well as related compositions, systems, kits and apparatuses, further comprise (f) separating the immuno-precipitated fragmented tagged cross-linked chromatin that is bound to the antibody from the unbound immuno-precipitated fragmented tagged cross-linked chromatin, where the separating is optionally performed with a magnet that binds the paramagnetic particle or bead. Optionally, the immuno-precipitated fragmented tagged cross-linked chromatin that is bound to the antibody is washed at least once to remove the unbound immuno-precipitated fragmented tagged cross-linked chromatin.

In some embodiments, methods, as well as related compositions, systems, kits and apparatuses, further comprise (g) reversing the cross-linking thereby releasing the fragmented tagged chromatin from the target DNA-binding protein. Optionally, the reversing step can be achieved using proteinase-K.

In some embodiments, methods, as well as related compositions, systems, kits and apparatuses, further comprise (h) amplifying the fragmented tagged chromatin to generate amplified chromatin.

In some embodiments, methods, as well as related compositions, systems, kits and apparatuses, further comprise (i) sequencing the amplified chromatin.

In some embodiments, the chromatin immuno-precipitation (ChIP) steps can be conducted according to manufacture instruction in: "Ion ChIP-Seq Library Preparation on the Ion Proton™ System" (User Bulletin 2014, Publication No. 4473623, Rev. G) and "Preparing Samples for ChIP Sequencing of DNA" (User Guide 2007, part #11257047, Rev. A).

In some embodiments, the plurality of transpososome complexes includes a plurality of transpososome complexes, each containing a plurality of transposons, and first and second transposon end sequences having the same sequence. In some embodiments, the plurality of transpososome complexes includes a plurality of hetero-transpososome complexes containing at least a first and second transpososome complex, where the first and second transposon end sequences of the first transpososome complex having the same sequence, and the first and second transposon end sequences of the second transpososome complex having the same sequence but differ from the first and second transposon end sequences of the first transpososome complex. The hetero-transpososome complexes include a mixture of 2-100 or more different transpososome complexes.

In some embodiments, chromatin from a second plurality of cells can undergo steps (a)-(i), in a manner similar to the chromatin from the first plurality of cells. In some embodiments, chromatin from a second chromatin sample can be contacted with a plurality of transpososome complexes in a separate single reaction mixture to produce fragmented tagged chromatin (e.g., steps (a)-(d)), which can optionally be immuno-precipitated with an antibody (e.g., step (e)), which can optionally be enriched (e.g., steps (f) and (g)), which can optionally be amplified (e.g., step (h)), and the resulting amplified chromatin can optionally be sequenced (e.g., step (i)), for comparison with the sequencing data obtained from the first chromatin sample. Optionally, the second plurality of cells is treated under a second condition that may cause a change in chromatin binding pattern of the target DNA-binding protein, and the first and second conditions differ from each other. The sequence data can be analyzed to identify changes in the chromatin structure (e.g., changes between open and closed chromatin, and vice versa) resulting from changes in cellular conditions. Optionally, the changes in chromatin structure that are revealed by the transpososome-mediated procedures can be compared to DNase I sensitivity analysis (Buenrostro, et al., 2013 Nature Methods 12:1213-1218; and Buenrostro, et al., 2015 Current Protocols Molecular Biology 109:21.29.1-21.29.9).

In some embodiments, the sequencing data from the first and second immuno-precipitated chromatin can be compared to identify changes in patterns of DNA-binding proteins that may play a role in cellular processes, including DNA replication, cell cycle regulation (e.g., mitosis and meiosis), recombination, segregation, transcription regulation, repair, translation regulation, chromosomal stability and epigenetic silencing.

In some embodiments, the first and second immuno-precipitated chromatin samples contain the same or different patterns of DNA-binding proteins. The first and/or second immuno-precipitated chromatin may be isolated from an initial nucleic acid sample containing as little as about 100 pg of DNA, or about 100 pg-1 ng, or about 1 ng-1 µg, or more. The first and/or second immuno-precipitated chromatin may be isolated from a single cell, or from about 2-1000 cells, or about 1000-10,000 cells, or about 10,000-100,000 cells. The first and/or second immuno-precipitated chromatin may be isolated from cells that are normal, diseased, carry at least one mutation or genetic variant, have been subjected to starvation or limited nutrients, have been treated with a chemical compound or a drug or a hormone, or have been challenged with a chemical compound, a drug, a hormone, or a physical condition that may cause a change in chromatin structure. The physical challenge condition includes temperature changes, cold, heat, light, electric shock, acoustic energy, pressure, osmotic changes, nutrient availability, pH changes, and others.

In some embodiments, the disclosure relates generally to methods, as well as related compositions, systems, kits and apparatuses, for fragmenting DNA in an in vitro reaction, using the transpososome-mediated procedures described in the present teaching, where the DNA is circulating cell-free DNA obtained from a biological fluid. The transpososome complexes can be used in a rapid and simple in vitro reaction to generate tagged DNA fragments that are further manipulated to generate a DNA library.

In some embodiments, the disclosure relates generally to methods, as well as related compositions, systems, kits and apparatuses, for fragmenting cell-free DNA in an in vitro reaction, comprising: (a) providing a plurality of transpososome complexes, which include (i) a plurality of transposases, (ii) a first transposon end sequence, wherein the first transposon end sequence is capable of binding to a transposase from the plurality of transposases and wherein the first transposon end sequence contains at least one nick, gap, apurinic site or apyrimidinic site, (iii) a second transposon end sequence, wherein the second transposon end sequence is capable of binding to a transposase from the plurality of transposases and wherein the second transposon end sequence contains at least one nick, gap, apurinic site or apyrimidinic site; (b) contacting, in a single reaction mixture, the plurality of transpososome complexes with cell-free DNA (e.g., obtained from a biological fluid), under conditions that are suitable for transposition of the first and second transposon end sequences into the cell-free DNA and fragmentation of the cell-free DNA; and (c) producing at least one fragmented tagged DNA molecule having a first end joined to the first transposon end sequence and a second end joined to the second transposon end sequence, by transposing the first transposon end sequences into a first position of the cell-free DNA and fragmenting and tagging the cell-free DNA, and by transposing the second transposon end sequences into a second position of the cell-free DNA and fragmenting and tagging the cell-free DNA, wherein the at least one fragmented tagged DNA molecules includes the first transposon end sequence having at least one nick, gap, apurinic site or apyrimidinic site, and a second end having at least one nick, gap, apurinic site or apyrimidinic site. Optionally, the plurality of transpososome complexes comprises mixture of hetero-transpososome complexes. Optionally, the fragmented tagged DNA molecule, which is joined at both ends to a transposon end sequence, can be further manipulated by appending at least one universal adaptor sequence using PCR with tailed primers or using adaptor ligation. The universal adaptor sequence may include any one or any combination of an amplification primer sequence, a sequencing primer sequence and/or a barcode sequence.

In some embodiments, methods, as well as related compositions, systems, kits and apparatuses, further comprise (d) amplifying the at least one fragmented tagged DNA molecule to generate tagged DNA amplicons.

In some embodiments, methods, as well as related compositions, systems, kits and apparatuses, further comprise (e) sequencing the tagged DNA amplicons.

In some embodiments, the plurality of transpososome complexes includes a plurality of transpososome complexes, each containing a plurality of transposons, and first and second transposon end sequences having the same sequence. In some embodiments, the plurality of transpososome complexes includes a plurality of hetero-transpososome complexes containing at least a first and second transpososome complex, where the first and second transposon end sequences of the first transpososome complex having the same sequence, and the first and second transposon end sequences of the second transpososome complex having the same sequence but differ from the first and second transposon end sequences of the first transpososome complex. The hetero-transpososome complexes include a mixture of 2-100 or more different transpososome complexes.

In some embodiments, the biological fluid is obtained from blood, serum, plasma, saliva, sputum, sweat, tears, lavage fluid, amniotic fluid (e.g., from a pregnant female), cerebrospinal fluid, ascites, urine, stool, feces, semen and the like. For example, blood, serum and plasma include fractions or processed portions thereof. Optionally, blood can be drawn from a subject using a collection tube that contains a compound that stabilizes blood cells (U.S. published application Nos. 2010/0184069, 2010/0209930, 2014/0199681; and Fernando, et al., 2010 Prenatal Diagnosis 30(5):418-424).

In some embodiments, the biological fluid is obtained from a subject that is healthy, or from a subject having a disease, or from a subject that has been treated with a chemical compound or a drug or a hormone.

In some embodiments, the biological fluid contains cells, bacteria, virus, fungus, cell-free nucleic acids or nucleic acids from circulating tumor cells.

In some embodiments, the transpososome complexes can be added directly to the biological fluid without any separate nucleic acid extraction or enrichment step. For example, the biological fluid, which contains the cell-free DNA, can be added directly to a reaction vessel along with the transpososome complexes for conducting any transpososome-mediated reaction described in the present teachings. In some embodiments, the biological fluid can undergo a separate processing step to extract the cell-free DNA, and the extracted cell-free DNA can be used to conduct a transpososome-mediated reaction. Optionally, an enrichment step can be performed on the biological fluid to remove cellular debris.

In some embodiments, the disclosure relates generally to methods, as well as related, systems, compositions, kits and apparatuses, for conducting an enrichment step on any of the tagged nucleic acid fragments that are generated using the transpososome-mediated procedures described in the present teachings. For example, the tagged nucleic acid fragments, including any of the tagged whole genome fragments, the tagged chromatin fragments, the tagged chromatin immuno-precipitated fragments, or the tagged cell-free fragments, can be subjected to an enrichment procedure. The enrichment step can be performed on a support or in solution. In some embodiments, the initial polynucleotides to be fragmented and tagged can be pre-enriched prior to performing any of the transpososome-mediated procedures of the present teachings.

In some embodiments, an enrichment step can be performed using a support (e.g., planar support or flowcell) or a plurality of supports (e.g., beads or particles) that is attached with a plurality of capture primers that can selectively hybridize to at least a portion of the tagged nucleic acid fragments. The capture primers can hybridize to at least a portion of the transposon end sequence that is joined to one end of the tagged nucleic acid fragments. The capture primers can hybridize to the target sequence of interest (e.g., insert sequence) of the tagged nucleic acid fragments. Non-limiting examples of the insert sequences include sequences that are associated with a species-specific gene sequence, an organ-specific gene sequence (e.g., skin, lung, kidney, breast, etc.), a house-keeping gene, a disease, a microbe, a pathogen, a bacteria, a virus, a fungus, or a forensic marker for human identification. Hybridization between the capture primers and the tagged nucleic acid fragments forms a nucleic acid duplex on the support. The support can include capture primers having the same sequence or multiple different sequences. The capture primers can be attached to the support in an organized or random pattern. The capture primers can be un-labeled or labeled (e.g., with a detectable label).

The methods, as well as related, systems, compositions, kits and apparatuses, for enriching the target nucleic acids includes: (a) providing a plurality of tagged nucleic acid fragments that are produced using any of the transpososome-mediated methods described in the present teachings, where tagged nucleic acid fragments include tagged target fragments and tagged non-target fragments; (b) contacting the plurality of tagged nucleic acid fragments with a plurality of capture primers that are attached to one or more supports, under conditions that selectively hybridize the tagged target fragments to the capture primers to form tagged target nucleic acid duplexes on the support and tagged non-target fragments that are not hybridized to a capture primer; (c) removing the tagged non-target fragments by washing away the tagged non-target fragments or by enzymatically degrading the tagged non-target fragments, or a combination of both; (d) eluting the tagged target fragments from the tagged target nucleic acid duplexes on the support; (e) subjecting the eluted tagged target fragments to further molecular biological manipulation (e.g., appending at least one adaptor sequence) and/or sequence analysis.

In some embodiments, an enrichment step can be performed in solution using a plurality of enrichment primers (e.g., soluble primers) that can selectively hybridize to at least a portion of the tagged nucleic acid fragments. The enrichment primers can hybridize to at least a portion of the transposon end sequence that is joined to one end of the tagged fragment. The capture primers can hybridize to the target sequence of interest (e.g., insert sequence) of the tagged nucleic acid fragments. Non-limiting examples of the insert sequences include sequences that are associated with a species-specific gene sequence, an organ-specific gene sequence (e.g., skin, lung, kidney, breast, etc.), a house-keeping gene, a disease, a microbe or a virus, a pathogen, or a forensic marker for human identification. Hybridization between the enrichment primers and the tagged nucleic acid fragments forms a nucleic acid duplex in solution. The plurality of enrichment primers can include the same sequence or multiple different sequences. At least one of the enrichment primers can be un-labeled or labeled (e.g., with a detectable label). At least one of the enrichment primers can include one member of a binding partner. The binding partner includes an affinity moiety and a receptor moiety that will bind to each other in preference to other molecules. At least one enrichment primer includes an affinity moiety to form an affinity-labeled enrichment primer. Non-limiting examples of binding partners include biotin which binds an avidin-like moiety (e.g., streptavidin). In some embodiments, at least one affinity-labeled enrichment primer includes a biotin moiety. Hybridization between the affinity-labeled enrichment primers (e.g., biotinylated enrichment primers) and the tagged nucleic acid fragments can form affinity-labeled duplexes which can be separated from molecules that are not bound to an affinity-labeled enrichment primer. For example, the affinity-labeled duplexes can be contacted with streptavidin-linked paramagnetic particles, and a magnet can be used to separate the affinity-labeled duplexes from molecules that are not bound to an affinity-labeled enrichment primer.

The methods, as well as related, systems, compositions, kits and apparatuses, for enriching the target nucleic acids includes: (a) providing a plurality of tagged nucleic acid fragments that are produced using any of the transpososome-mediated methods described in the present teachings, where the tagged nucleic acid fragments include tagged target fragments and tagged non-target fragments.

The methods, as well as related, systems, compositions, kits and apparatuses, for enriching the target nucleic acids further includes: (b) contacting the plurality of tagged nucleic acid fragments with a plurality of soluble affinity-labeled enrichment primers, which include enrichment primers attached to an affinity moiety (e.g., biotin), under conditions that selectively hybridize the tagged target fragments to the affinity-labeled enrichment primer to form (i) tagged target nucleic acid duplexes and optionally (ii) tagged non-target fragments (e.g., non-duplexed).

The methods, as well as related, systems, compositions, kits and apparatuses, for enriching the target nucleic acids further includes: (c) separating the tagged target nucleic acid duplexes from the tagged non-target fragments by contacting the (i) tagged target nucleic acid duplexes with (ii) a plurality of paramagnetic particles attached to receptor moieties (e.g., streptavidin), thereby separating the tagged target nucleic acid duplexes from the tagged non-target fragments.

The methods, as well as related, systems, compositions, kits and apparatuses, for enriching the target nucleic acids further includes: (d) removing the tagged non-target fragments from the tagged target nucleic acid duplexes.

The methods, as well as related, systems, compositions, kits and apparatuses, for enriching the target nucleic acids further includes: (e) subjecting the tagged target nucleic acid duplexes to further molecular biological manipulation (e.g., appending at least one adaptor sequence) and/or sequence analysis.

In some embodiments, the disclosure relates generally to methods, as well as related, systems, compositions, kits and apparatuses, comprising fragmenting and tagging polynucleotides in an in vitro reaction, using any of the transpososome-mediated procedures described in the present teaching, where the polynucleotides are naturally-occurring, genomic, synthetic, recombinant, cloned, fragmented, un-fragmented, amplified, unamplified or archived (e.g., preserved) forms. The polynucleotides can be randomly fragmented using enzymatic, chemical or mechanical procedures (e.g., mechanical shearing, sonication, nebulization, or acoustics). Fragmentation can be pre-determined using restriction endonucleases. Fragment sizes can be about 20-10,000 base-pairs in length. The polynucleotides include DNA, cfDNA (e.g., cell-free DNA), or ctDNA (e.g., circulating tumor DNA). The polynucleotides can be cDNA (e.g., copy DNA synthesized from RNA), or can be derived from any type of RNA, including mRNA, miRNA, rRNA, tRNA, cfRNA (cell-free RNA), RNA/DNA, or a mixture of any of these nucleic acids.

In some embodiments, the polynucleotides originate from a biological sample, including a biological fluid, cell culture, solid tissue or solid tumor. The polynucleotides originate from a single tube of drawn blood, or from multiple tubes of drawn blood. The polynucleotides originate from any organism including a prokaryote, eukaryote, human, canine, feline, bovine, equine, murine, porcine, caprine, lupine, ranine, piscine, simian, ape, plant, insect, bacteria, virus or fungus.

In some embodiments, the polynucleotides originate from samples collected from soil, food, water, a hospital, or a suspected bio-threat target. In some embodiments, the polynucleotides originate from one or a combination of infectious agents in water, soil or food, including *Campylobacter, Salmonella, Shigella, Escherichia coli, Listeria, Staphylococcus, Clostridium, Vibrio, Yersinia, Baceroides, Enterococcus, Kiebsiella, Proteus, Citrobacter, Elaemophilis, Neisseria, Lactobacillus, Bifidobacterium, Fusobacterium, Propionibacterium, Veillonella, Pseudomonas, Corynebacterium, Peptostreptcoccus*, novovirus and many others.

In some embodiments, the polynucleotides originate from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs.

In some embodiments, the polynucleotides comprise DNA, RNA or a mixture of DNA and RNA from nucleus, mitochondria, chloroplast, and also includes plasmids, phagemids and recombinant vectors.

In some embodiments, the polynucleotides originate from a biological sample, including a biological fluid obtained from blood, serum, plasma, saliva, sputum, sweat, tears, lavage fluid, amniotic fluid (e.g., from a pregnant female), cerebrospinal fluid, ascites, urine, stool, feces, semen and the like. For example, blood, serum and plasma include fractions or processed portions thereof. Optionally, the nucleic acid sample can be a formalin fixed paraffin-embedded (FFPE) sample, which contains polynucleotides, or can be from a fresh biological sample that is not archived or preserved.

In some embodiments, the polynucleotides originate from a biological sample including a biological fluid or solid tissue obtained by biopsy, swab, or smear. In some embodiments, the solid tissue includes healthy or diseased tissue (e.g., tumor) or fluid, or a mixture of healthy and diseased tissue or fluid.

In some embodiments, the polynucleotides originate from a biological sample that contains cells, bacteria, virus, fungus and/or cell-free nucleic acids or nucleic acids isolated from circulating tumor cell(s).

In some embodiments, a nucleic acid sample (e.g., which contains the polynucleotides) can undergo a separate processing step to extract the polynucleotides, and the extracted polynucleotides can be used to conduct any transpososome-mediated reaction described in the present teachings. Optionally, an enrichment step can be performed on the nucleic acid sample to remove cellular debris. Optionally, cells contained within the nucleic acid sample can be lysed to release the polynucleotides which are then enriched or purified to remove the cellular debris. In some embodiments, the transpososome complexes can be added directly to the biological fluid without any separate nucleic acid extraction or enrichment step. For example, the biological fluid, which contains the cell-free DNA, can be added directly to a reaction vessel along with the transpososome complexes for conducting any transpososome-mediated reaction described in the present teachings. In some embodiments, a separate cell lysis step is not practiced, or a lysis step is conducted prior to the transpososome-mediated reaction.

In some embodiments, the polynucleotides include single-stranded or double-stranded polynucleotides, or a mixture of both. The plurality of polynucleotides includes polynucleotides having the same sequence or a mixture of different sequences. The plurality of polynucleotides can include polynucleotides having the same or different lengths. The plurality of polynucleotides can include about 2-10, or about 10-50, or about 50-100, or about 100-500, or about 500-1,000, or about 1,000-5,000, or about $10^3$-$10^6$, or about $10^6$-$10^{10}$ or more polynucleotide molecules. The plurality of polynucleotides comprises polymers of deoxyribonucleotides, ribonucleotides, and/or analogs thereof.

In some embodiments, the transpososome-mediated reactions can be performed with as little as about 1 pg of DNA, or about 1-100 pg of DNA, or about 100 pg-1 ng of DNA, or about 1 ng-1 µg of DNA, or more.

In some embodiments, the polynucleotides include a wild-type form, and optionally include its related polymorphic forms, which can include variant, allelic and/or mutant forms. The related variant forms contain at least one genetic insertion, deletion, substitution, splice, sequence fusion (e.g., gene fusion or RNA fusion), truncation, transversion, translocation or other genetic rearrangement. The mutant or variant sequences also include copy number variation, aneuploidy, partial aneuploidy, or polyploidy.

In some embodiments, the disclosure relates generally to methods, as well as related, systems, compositions, kits and apparatuses, comprising fragmenting and tagging polynucleotides in an in vitro reaction, using any of the transpososome-mediated procedures described in the present teaching, where any of the polynucleotides, transposon end sequences, adaptors, tailed primers, amplification primers, sequencing primers, or capture primers, are non-labeled or attached to at least one label. In some embodiments, the label comprises a detectable moiety. In some embodiments, the label can generate, or cause to generate, a detectable signal. In some embodiments, the detectable signal can be generated from a chemical or physical change (e.g., heat, light, electrical, pH, salt concentration, enzymatic activity, or proximity events). For example, a proximity event can include two reporter moieties approaching each other, or associating with each other, or binding each other. In some embodiments, the detectable signal can be detected optically, electrically, chemically, enzymatically, thermally, or via mass spectroscopy or Raman spectroscopy. In some embodiments, the label can include compounds that are luminescent, photoluminescent, electroluminescent, bioluminescent, chemiluminescent, fluorescent, phosphorescent or electrochemical. In some embodiments, the label can include compounds that are fluorophores, chromophores, radioisotopes, haptens, affinity tags, atoms or enzymes. In some embodiments, the label comprises a moiety not typically present in naturally occurring nucleotides. For example, the label can include fluorescent, luminescent or radioactive moieties.

In some embodiments, the disclosure relates generally to methods, as well as related, systems, compositions, kits and apparatuses, comprising fragmenting and tagging polynucleotides in an in vitro reaction, using any of the transpososome-mediated procedures described in the present teaching, where any of the polynucleotides, transposon end sequences, adaptors, tailed primers, amplification primers, sequencing primers, or capture primers include at least one member of a binding partner. In some embodiments, a binding partners includes two molecules, or portions thereof, which have a specific binding affinity for one another and typically will bind to each other in preference to binding to other molecules. In some embodiments, binding partners include an "affinity moiety" and a "receptor moiety". Typically but not necessarily some or all of the structure of one member of a specific binding pair is complementary to some or all of the structure possessed by the other member, with the two members being able to bind together specifically by way of a bond between the complementary structures, optionally by virtue of multiple non-covalent attractions.

In some embodiments, molecules that function as binding partners include: biotin (and its derivatives) and its binding partners avidin, streptavidin and their derivatives; His-tags which bind nickel, cobalt or copper; cysteine, histidine, or histidine patch which bind Ni-NTA; maltose which binds with maltose binding protein (MBP); lectin-carbohydrate binding partners; calcium-calcium binding protein (CBP); acetylcholine and receptor-acetylcholine; protein A and binding partner anti-FLAG antibody; GST and binding partner glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin can be a biotin-binding protein from chicken (Hytonen, et al., BMC Structural Biology 7:8).

In some embodiments, an avidin moiety can include an avidin protein, as well as any derivatives, analogs and other non-native forms of avidin that can bind to biotin moieties. Other forms of avidin moieties include native and recombinant avidin and streptavidin as well as derivatized molecules, e.g. nonglycosylated avidins, N-acyl avidins and truncated streptavidins. For example, avidin moiety includes deglycosylated forms of avidin, bacterial streptavidins produced by *Streptomyces* (e.g., *Streptomyces avidinii*), truncated streptavidins, recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin™, Captavidin™, Neutravidin™ and Neutralite Avidin™.

Unless specifically defined or described differently, the invention uses the following terms and descriptions.

The term "transposon" as used herein is a nucleic acid segment that is recognized by a transposase or an integrase enzyme and which is an essential component of a functional nucleic acid-protein complex ("transposome complex") capable of transposition. The inventive transposons in one embodiment belong to class II transposable DNA elements, which use fundamentally similar reactions for their movement within and between genomes, namely, the transposition reaction is catalyzed by a transposase enzyme by either a double- or single-stranded DNA intermediate and transposon DNA is translocated in the "cut and paste" manner within genome. The term "transposon" as used herein also includes all derivatives of the original transposable element, such as mini-transposons or other reiterations of minimal nucleic acid-protein complex capable of transposition, including but not limited to two individual not interconnected transposon ends, or said ends joined by some artificial linker.

The term "transposase" as used herein refers to an enzyme that is a component of a functional nucleic acid-protein complex capable of transposition of the transposon end sequence into a target nucleic acid. The transposase enzyme mediates transposition.

The terms "transposon end" or "transposon end sequence" is a sequence recognized by a transposase enzyme necessary to form a synaptic complex or a "transpososome complex", sufficient for a subsequent transposition event to occur in vitro. "Sufficient for a subsequent transposition event to occur in vitro" means transposon end sequences necessary for both recognition and binding of a transposase enzyme, including a terminal stretch of nucleotides of about five base pairs, the last two base pairs being the attacking 5'-CA, these five base pairs necessary for the transposition reaction to occur. A transposon end and transposase protein form a "complex" or a "synaptic complex" or a "transposome complex", the complex capable of inserting or transposing the transposon end into target DNA with which it is incubated in an in vitro transposition reaction. Transpososomes contain multiple subunits of a transposase protein, bound to DNA sequences from both of the transposon's ends. These protein-DNA complexes are also called "synaptic complexes" because they bring together the two ends of the transposon DNA. The phage Mu transposase, MuA, is monomeric in solution but forms a tetramer upon binding to specific DNA recognition sites near the transposon ends. The critical reaction steps mimicking Mu transposition into external target DNA can be reconstituted in vitro using MuA transposase, 50 bp Mu R-end DNA segments, and target DNA as the only macromolecular components (Haapa et al. An efficient and accurate integration of mini-Mu transposons in vitro: A general methodology for functional genetic analysis and molecular biology applications. Nucleic Acids Res 27 (1999) 2777-2784).

The term "adaptor" as used herein refers to a non-target nucleic acid component, generally DNA, that provides a means of addressing a nucleic acid fragment to which it is joined. For example, an adaptor comprises a nucleotide sequence that permits identification, recognition, and/or molecular or biochemical manipulation of the DNA to which the adaptor is attached (e.g., by providing a site for annealing an oligonucleotide, such as a primer for extension by a DNA polymerase, or an oligonucleotide for capture or for a ligation reaction).

In some embodiments, the fragments produced using any of the transposon-based approaches described herein can be joined to at least one adaptor, or can lack any adaptor. In some embodiments, one or more adaptors can be joined to the fragments by ligation.

In some embodiments, the adaptor comprises a nucleic acid, including DNA, RNA, RNA/DNA molecules, or analogs thereof. In some embodiments, the adaptor can include one or more deoxyribonucleoside or ribonucleoside residues. In some embodiments, the adaptor can be single-stranded or double-stranded nucleic acids, or can include single-stranded and/or double-stranded portions. In some embodiments, the adaptor can have any structure, including linear, hairpin, forked (Y-shaped), or stem-loop.

Optionally, a Y-shaped adaptor contains at least one unique sequence (e.g., barcode). For example the stem portion of the Y-shaped adaptor contains at least one unique sequence.

In some embodiments, the adaptor can have any length, including fewer than 10 bases in length, or about 10-20 bases in length, or about 20-50 bases in length, or about 50-100 bases in length, or longer.

In some embodiments, the adaptor can have any combination of blunt end(s) and/or sticky end(s). In some embodiments, at least one end of the adaptor can be compatible with at least one end of a nucleic acid fragment. In some embodiments, a compatible end of the adaptor can be joined to a compatible end of a nucleic acid fragment. In some embodiments, the adaptor can have a 5' or 3' overhang end.

In some embodiments, the adaptor can have a 5' or 3' overhang tail. In some embodiments, the tail can be any length, including 1-50 or more nucleotides in length.

In some embodiments, the adaptor can include an internal nick. In some embodiments, the adaptor can have at least one strand that lacks a terminal 5' phosphate residue. In some embodiments, the adaptor lacking a terminal 5' phosphate residue can be joined to a nucleic acid fragment to introduce a nick at the junction between the adaptor and the nucleic acid fragment.

In some embodiments, the adaptor can include a nucleotide sequence that is identical or complementary to any portion of the fragments that are generated by the transposon-based approaches. In some embodiments, the adaptor can include a nucleotide sequence that is identical or complementary to an amplification primer sequence and/or a sequencing primer sequence.

In some embodiments, the adaptor can include a unique identifier sequence (e.g., barcode sequence). In some embodiments, a plurality of barcoded adaptors (e.g., plurality of different barcoded adaptors) can be used for constructing a multiplex library of polynucleotides (e.g., fragments generated using the transposon-based approaches described herein). In some embodiments, the barcoded adaptors can be appended to a polynucleotide and used for sorting or tracking the source of the polynucleotide. For example, a population of polynucleotides can be appended to a common barcoded adaptor which identifies the polynucleotides as being obtained from a common source. In some embodiments, one or more barcode sequences can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences.

In some embodiments, the adaptor can include degenerate sequences. In some embodiments, the adaptor can include one or more inosine residues.

In some embodiments, the adaptor can include at least one scissile linkage. In some embodiments, the scissile linkage can be susceptible to cleavage or degradation by an enzyme or chemical compound. Optionally, the adaptor includes at least one uracil base. In some embodiments, the adaptor can include at least one phosphorothiolate, phosphorothioate, and/or phosphoramidate linkage. For example, an adaptor containing at least one uracil base is cleavable with uracil DNA glycosylase (UDG) and formamidopyrimidine DNA glycosylase (Fpg).

In some embodiments, the adaptor can include any type of restriction enzyme recognition sequence, including type I, type II, type IIs, type IIB, type III, type IV restriction enzyme recognition sequences, or recognition sequences having palindromic or non-palindromic recognition sequences.

In some embodiments, the adaptor can include a cell regulation sequences, including a promoter (inducible or constitutive), enhancers, transcription or translation initiation sequence, transcription or translation termination sequence, secretion signals, Kozak sequence, cellular protein binding sequence, and the like.

In some embodiments, the adaptor can be compatible for use in any type of sequencing platform including chemical degradation, chain-termination, sequence-by-synthesis, pyrophosphate, massively parallel, ion-sensitive, and single molecule platforms. In some embodiments, any primer or adaptor can be compatible for use in any type of sequencing procedure including: sequencing by oligonucleotide probe ligation and detection (e.g., SOLiD™), probe-anchor ligation sequencing (e.g., Complete Genomics or Polonator™) sequence-by-synthesis (e.g., Illumina), pyrophosphate sequencing (e.g., 454 Life Sciences), ion-sensitive sequencing (e.g., Personal Genome Machine (PGM™) and Ion Proton™ Sequencer, both from Ion Torrent Systems, Inc.) and single molecule sequencing platforms (e.g., Helicos™). For example, any primer or adaptor can be used to graft a polynucleotide to a support (e.g., bead, flowcell or array of reaction sites) that is used for conducting a sequencing reaction.

The term "equimolar concentration" as used herein refers to transposase protein-transposon nucleic acid ratio enabling formation of completely assembled transposome complexes where all complex partners are utilized and no excessive complex partners remain free in solution. For the Mu transposition system such ratio represents four MuA transposase protein molecules and two Mu transposon end sequences that are able to interact with MuA, while for the Tn5 system such ratio is two Tn5 transposase protein molecules and two Tn5 transposon end sequences. In the inventive method, transposome assembly is performed in more concentrated transposase/transposon end reaction mixture (in concentrations that correspond to 4 transposase molecules per 2 transposon ends ("equimolar concentrations")) optimized for transposome complex formation. After assembly, the preformed complexes are diluted and target DNA is added. A reaction mixture with target DNA is suboptimal for complex formation, so in addition to the lack of transposase turnover, this is another factor that leads to exhaustion of preformed active transposome complexes and the reaction stops at certain level of DNA degradation.

In some embodiments, a "support" comprises a planar surface, as well as concave, convex, or any combination of surfaces thereof. In some embodiments, a "support" includes a bead, particle, microparticle, sphere, filter, flowcell, well, microwell, groove, channel reservoir, gel or inner wall of a capillary. Optionally, the support includes the inner walls of a capillary, a channel, a well, microwell, groove, channel, reservoir. Optionally, the support includes texture (e.g., etched, cavitated, pores, three-dimensional scaffolds or bumps). Optionally, the support can be porous, semi-porous or non-porous. Optionally, the support includes one or more beads having cavitation or pores, or can include three-dimensional scaffolds. Optionally, the support includes an Ion Sphere™ particle (from Ion Torrent, part of Life Technologies, Carlsbad, Calif.). Optionally, the particles have any shape including spherical, hemispherical, cylindrical, barrel-shaped, toroidal, rod-like, disc-like, conical, triangular, cubical, polygonal, tubular, wire-like or irregular. In some embodiments, the support can be made from any material, including glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond). In some embodiments, the support can be magnetic or paramagnetic. In some embodiments, the support includes paramagnetic beads attached with streptavidin (e.g., Dynabeads™ M-270 from Invitrogen, Carlsbad, Calif.). Optionally, the bead or particle can have an iron core, or comprise a hydrogel or agarose (e.g., Sepharose™). Optionally, the support is coupled to at least one sensor that detects physicochemical byproducts of a nucleotide incorporation reaction, where the byproducts include pyrophosphate, hydrogen ion, charge transfer, or heat.

Interaction of various transposases with their substrate DNA (transposon ends) are described in the prior art to the extent that allows one skilled in the art to determine borders of transposon ends for various transposome complexes (Montano and Rice 2011. Moving DNA around: DNA transposition and retroviral integration. Curr. Opin. Struct. Biol. 21, 370-378). The scientific literature may reference transposon ends as a primary substrate for a transposase protein, which is necessary for transposome complex assembly. However, only a fully assembled transposome can attack target DNA, so the target DNA is a substrate for assembled transposome complex, but not for transposase enzyme.

Conventional DNA sequencing methods are currently being replaced by so called "next-generation" technologies or "massive parallel sequencing" platforms that allow millions of nucleic acid molecules to be sequenced simultaneously. These methods rely on a sequencing-by-synthesis approach, while other platforms are based on a sequencing-by-ligation technology. All of these new technologies rely on a pool of sequencing templates (DNA library), which later may be multiplied by use of DNA amplification techniques.

There are two main methodologies in DNA library preparation. So-called conventional DNA library preparation procedures include DNA fragmentation (hydroshearing, sonication, nebulization, or enzymatic shearing) followed by DNA repair and end-polishing (blunt-end or A-overhang), and finally platform-specific adaptor ligation. Transposon-based DNA library preparation procedures use in vitro transposition to prepare sequencing-ready DNA libraries: during in vitro transposition catalyzed by transposase-transposon end complex, strand transfer occurs via random, staggered double-strand DNA breaks in the target DNA and covalent attachment of the 3' end of the transferred transposon strand to the 5' end of the target DNA. When two transposon ends which participate in the in vitro transposition reaction are not interconnected, the target DNA is fragmented and the transferred strand of the transposon end oligonucleotide is covalently attached to the 5' end of the DNA fragment. Independent tags can also be added to the fragmented DNA by appending the transposon end sequence with an engineered adaptor sequence. After extension, the sequencing adaptors enable amplification by emulsion PCR (emPCR), bridge PCR (bPCR), and other methods.

Commercial conventional and transposon based DNA library preparation methods in the form of DNA library preparation kits are available (e.g., Illumina, Life Technologies, New England Biolabs), but these face limitations: multi-step protocols require numerous DNA manipulation steps that result in long and laborious workflow and may result in significant DNA sample loss and limited throughput.

Transposon based DNA library preparation methods, although in general demand less hands-on time and are more convenient for the user, also have limitations: in vitro transposition products having complementary transposon end sequences at both ends tend to form intramolecular loop structures when denatured to single stranded DNA. This is particularly a problem when the fragmented DNA is subjected to PCR amplification.

In addition, massive parallel sequencing platforms typically require that the initially long polynucleotide chains be reduced to smaller nucleic acid fragments having average length in base pairs as specified by the operational setting of the sequence reader. Current sequencing read lengths vary from 50 bp to 1000 bp. For some massive parallel sequencing platforms mate-pair sequencing library preparation methods demanding nucleic acid fragments from 5 kb to 40 kb are applied. Conventional nucleic acid fragmentation methods, such as enzymatic digestion, nebulization, hydro-shear, and sonication are based on random nucleic acid shearing, thus required nucleic acid fragments having length corresponding to operational setting of the sequence reader need to be additionally purified from the mixture of nucleic acid fragments by various size selection protocols.

There still is a need for methods that enable fragmentation of a DNA sample to a desired predefined average DNA fragment size, and that facilitate downstream handling of the fragmented DNA obtained from the in vitro transposition step.

Methods were suggested to overcome self-annealing of complementary transposon end sequences resulting from in vitro transposition event. For example, in Nextera DNA Sample Preparation Kits that employ Tn5 transposase-transposon end complexes, transposon ends are appended with sequencing primer sequences that are not complementary.

Grunenwald U.S. Published Patent Application No. 2010/0120098 disclose methods for using a transposase and a transposon end for generating extensive fragmentation and 5'-tagging of double-stranded target DNA in vitro. The method is based on use of a DNA polymerase for generating 5'- and 3'-tagged single-stranded DNA fragments after fragmentation without performing PCR amplification reaction. Tagged transposon ends are disclosed, but the actual transposon end sequence of the used transposons corresponds to the native Tn5 transposon sequence. The tag domain combined with the native transposon end can comprise a sequence or structure of a cleavable site, with the method comprising a step of incubating the tagged DNA fragments obtained from the fragmentation step with a cleavage enzyme. The application describes transposon ends having the cleavage site in the tag sequence that is attached to the 5'-end of the transposon end sequence, but not in the transposon end sequence itself.

Kavanagh U.S. Published Patent Application No. 20130017978 teach methods to truncate transposon ends after DNA fragmentation thereby making them non complementary. The methods comprise the steps of (a) initiating an in vitro transposition reaction in the presence of a transposon end, transposase enzyme, and target DNA, wherein the transposon end comprises a transposon end sequence recognizable by a transposase, the transposon end sequence comprising a modified position or modified positions, where the modified position or positions introduce(s) a cleavage site into the transposon end sequence, and where the in vitro transposition reaction results in fragmentation of the target DNA and incorporation of the transposon end into the 5' ends of the fragmented target DNA; and (b) incubating the fragmented target DNA with an enzyme specific to the cleavage site so the transposon ends incorporated into the fragmented target DNA are cleaved at the cleavage site. Examples of such modification/cleavage are provided: transposons containing uracil can be truncated using UDG and subsequent heat or endonuclease treatment; transposons containing m5C can be truncated using methylation sensitive restriction endonuclease SgeI; and transposons containing RNA/DNA hybrid parts can be truncated using RNAse H.

Although these approaches may be used for efficient transposon end truncation, they have limitations. Use of uracil, m5C or RNA can impede transposase-transposon end complex formation or inhibit its activity in vitro (DNA fragmentation capability) due to unnatural transposon end structure. The need to introduce such modifications into transposon ends increases the cost of synthesis of transposon end oligonucleotides. Transposon end truncation is an enzymatic process that requires complicated optimization and extends DNA library preparation workflow time. After incubation, enzymes used for cleavage need to be inactivated or removed to avoid possible negative impacts in later DNA library preparation steps.

The inventive method provides modifications introduced into certain positions of transposon ends, the modifications including lesions such as a nick, nucleotide gap, or a modified sequence including a degenerated transposon end sequence which, after complexing such transposon ends with a transposase enzyme, result in synaptic complexes that, although with decreased affinity to the transposon end sequences, are both sufficiently stable in the in vitro transposition reaction mixture, and can perform in vitro transposition events resulting in a controlled DNA fragmentation that reduced the DNA sample to a desired average DNA fragment size. Such transposase/modified transposon end (containing apurinic/apyrimidinic site, nick, or gap) complexes may be applied for generation of DNA fragments of predefined length, or as in the case of DNA lesions, for generation of DNA fragments of predefined length that contain shortened stretches of transposon end sequences and for production of asymmetrically tailed DNA fragments.

The possibility of MuA transposase to accommodate and process a variety of different hairpin structured substrates containing right transposon ends with MuA-binding sites R1 and R2 was addressed (Saariaho et al., Nucleic Acids Research 34 (2006) 3139-3149). As a result, most of Mu specific hairpin substrates were generated from two oligonucleotides, and therefore these hairpin substrates contained a nick within the R1 MuA binding site. A direct comparison of in vitro transposition reactions catalyzed by MuA transposase interacting with nicked and corresponding unnicked hairpin substrate indicated that this nick does not interfere with in vitro transposition reactions. The structure of crystallized MuA final strand transfer complex, which contained a tetramer of truncated MuA proteins, two copies of the bacteriophage Mu end DNA, and one target DNA was resolved (Montano et al., Nature 491 (Nov. 15, 2012) 413-417). Mu end DNA duplexes were assembled to mimic the transposition reaction product of initial bacteriophage Mu transposon DNA cleavage by MuA transposase generating pre-cleaved right transposon ends exposing free 3'-OH groups able to attack 5'-end of the target DNA. Therefore, Mu end DNA duplexes were prepared by mixing in equal molar amounts four single stranded oligonucleotides containing R1 and R2 binding sites for recognition and binding of four MuA proteins resulting in a nick on each strand of the duplex at a position that does not interfere with transposome assembly. MuA transposition machinery tolerates certain variability in the transposon end sequences (Goldhaber-Gordon et al. J Biol Chem. 277 (2002) 7703-12). However, neither of these publications suggested that nick- or gap-bearing, or degenerate sequences-bearing, transposon ends assembled into catalytically active complexes with a transposase enzyme can be applied for controlled DNA fragmentation, generation of DNA fragments containing shortened stretches of transposon end sequences, or production of asymmetrically tailed DNA fragments.

Use of pre-nicked transposon ends or transposon ends with a nucleotide gap is a fast and simple alternative to enzymatic truncation. Pre-nicked transposon ends or transposon ends with a nucleotide gap do not contain any sophisticated modifications which could distort DNA structure, so complex formation process efficiency is comparable to that characteristic for a native transposon end. After an in vitro transposition reaction, such transposon ends are held on complementary DNA by weak hydrogen bonds and, depending on the length of the complementary region, either disintegrate from fragmented DNA itself immediately after the in vitro transposition reaction or after the initial adapter addition PCR (AA-PCR) elongation step in those cases when a nick or gap was introduced far from the 3' end of the attacking strand. As the transposon end truncation is determined by the nick or gap position in the attacking transposon strand, it may be varied easily. Transposon end truncation via nick or gap introduction may be used for generating shorter complementary transposon ends in the DNA library construction, leading to more efficient amplification of fragmented DNA, and production of asymmetrically tailed DNA fragments possessing the full length transposon end only at one end of processed DNA fragment.

The data provided herein demonstrate that, surprisingly, transpososomes formed from about equimolar concentrations of transposase and modified transposon ends comprising a nick or a nucleotide gap or degenerated nucleotide sequences can form active transposomes. Due to lower transposase affinity to its substrate (modified transposon end) the actual effective concentration of fully assembled transposomes is lower than that obtained using native transposon ends. This enables generation of DNA fragments of desired length by varying the amounts of either target genomic DNA or preassembled transposome complex in the transposition reaction mixture. It is known that DDE transposases usually do not turn over and MuA complex is so stable that it remains tightly bound to target DNA until it is removed in an ATP-dependent fashion by ClpX protein (Gueguen et al., TRENDS in Microbiology 13 (2005) 543; Nakai et al. Proc Natl Acad Sci USA. 98 (2001) 8247-54), therefore the number of transposition events in the reaction mixture is determined by the effective amount of preassembled transposomes as secondary transposition does not occur and the reaction is terminated (all preassembled transposome complexes added to the reaction mixture are exhausted) and DNA fragments of a certain average length are obtained as a result. DDE transposases are ubiquitous and represent the majority of characterized transposases, whose overall catalytic mechanism is known (Mizuuchi 1992a; reviewed by Mizuuchi 1992b). Members of the DDE transposase family carry a conserved triad of acidic residues: a DDE motif. The three acidic residues are crucial in the coordination of divalent metal ions required for catalysis (Kulkosky et al., 1992). The abundant DDE transposase family includes prokaryotic insertion sequences (ISs), members of the Tn3 family of transposons, the Tn7, Tn5 and Tn10 families and transposable bacteriophages such as phage Mu (Nagy and Chandler 2004, reviewed by Craig et al. 2002) and eukaryotic "cut and paste" transposons (Jurka et al. 2005; Yuan and Wessler 2011). The family can be extended to include retroviruses such as HIV, which encode a catalytic integrase protein similar to the DDE transposases (Dyda et al. 1994; Haren et al. 1999; Rice et al. 1996; Rice and Baker 2001). "Turn over rate" defines the maximum number of substrate molecules that the enzyme can 'turn over' to product in a set time. According to the literature, DDE transposases do not turn over under normal reaction conditions, i.e. after catalyzing one insertion into target DNA, the transposase stays bound to target DNA and is not released, thus the same enzyme molecule cannot participate in the assembly of the second transposome complex and cannot catalyze the second transposition event. As a result, the number of transposition events is dependent on the effective amount of catalytically active transposome complexes added to reaction mixture after which the reaction stops generating DNA fragments of a certain average length.

The inventive preassembled transposomes may be used as a universal and controlled DNA fragmentation tool enabling generation of DNA fragments having predefined average length. Embodiments are illustrated by the following non-limiting Examples and Figures.

One skilled in the art will find it apparent that various transposase enzymes complexed with their relevant transposon ends containing either an abasic site, nick, or gap may be used to practice the full scope of the invention. For example, in Mos1 and Mu transpososomes, transposon ends are bound by the helix-turn-helix-motifs of the bipartite DNA binding domains. Similar architecture of the transposon DNA-binding indicates that a gap or a nick can be efficiently accommodated in the transposon end DNA fragment without significant loss of function in either Mos1 transpososome, as was shown here to be the case for MuA. Another example of a suitable enzyme for practicing the invention is Tn5 transposome complex. Transposon ends required to produce stable dimeric transposome complex with Tn5 transposase are disclosed in U.S. Patent Application Publication No. 2010/0120098. It was shown that, like MuA transposase, Tn5 transposase tolerates nucleotide substitutions, abasic sites, and even nucleotide deletions in certain positions of its transposon end (Jilk et al. The organization of the outside end of transposon Tn5, J. Bacteriol. 178 (1996) 1671-1679) and is still able to bind to such substrates in vitro. It is therefore reasonable to expect that this enzyme when complexed with pre-nicked transposon ends or transposon ends containing a gap should also perform controlled DNA fragmentation disclosed in the present invention. Similarly, transposase from Vibrio harvey tolerates substitutions in its binding sequence IRR (EP 2,527,438 Methods and compositions for DNA fragmentation and tagging by transposases) hence, taking into account the significant homology between Tn5 transposase protein and Vibrio harvey transposase (40% homology), it is reasonable to expect that this transposase may also be used as one more enzyme to practice the present invention. The data provided herein are sufficient to teach the skilled artisan which sequences within the transposon end have to be modified by converting to degenerate sequences to obtain transposomes with decreased affinity to its substrate-transposon ends, resulting in a slower transposition reaction rate for the transposome complex and/or a lower transposase affinity to its substrate (transposon) within the transposome complex. By reducing the reaction rate and/or affinity, the transposome complex fragments the target DNA at a lower rate. The lower rate of target DNA fragmentation enhances control of the average length of the resulting DNA fragments by varying (a) an amount of transposon complex, (b) an amount of target DNA in the reaction complex, (c) incubation time of the transposition reaction, (d) amount of the introduced degenerate sequence, (e) location of the degenerate sequence. Manipulating the reaction conditions used with the modified transposon end sequence permits determination of reaction conditions, e.g., incubation time, that results in a particular average fragment length. Those determined conditions can then be used to create a DNA library comprising a desired, predefined average fragment length.

In some embodiments, any fragmented nucleic acid that has been generated according to the present teachings can be sequenced by any sequencing method, including sequencing-by-synthesis, ion-based sequencing involving the detection of sequencing byproducts using field effect transistors (e.g., FETs and ISFETs), chemical degradation sequencing, ligation-based sequencing, hybridization sequencing, pyrophosphate detection sequencing, capillary electrophoresis, gel electrophoresis, next-generation, massively parallel sequencing platforms, sequencing platforms that detect hydrogen ions or other sequencing by-products, and single molecule sequencing platforms. In some embodiments, a sequencing reaction can be conducted using at least one sequencing primer that can hybridize to any portion of the nucleic acid templates, including a nucleic acid adaptor or a target polynucleotide.

In some embodiments, any fragmented nucleic acid template that has been generated according to the present teachings can be sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in U.S. Pat. No. 7,948,015 to Rothberg et al, and U.S. Patent Publication No. 2009/0026082 to Rothberg et al, hereby incorporated by reference in their entireties. Other examples of methods of detecting polymerase-based extension can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992), which are hereby incorporated by reference in their entireties.

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be flowed across the well, one at a time, under nucleotide incorporation conditions. The polymerase incorporates the appropriate nucleotide into the growing strand, and the hydrogen ion that is released can change the pH in the solution, which can be detected by an ion sensor that is coupled with the well. This technique does not require labeling of the nucleotides or expensive optical components, and allows for far more rapid completion of sequencing runs. Examples of such ion-based nucleic acid sequencing methods and platforms include the Ion Torrent PGM™ or Proton™ sequencer (Ion Torrent™ Systems, Life Technologies Corporation).

In some embodiments, any fragmented nucleic acids produced using the methods, systems and kits of the present teachings can be used as a substrate for a biological or chemical reaction that is detected and/or monitored by a sensor including a field-effect transistor (FET). In various embodiments the FET is a chemFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127 (which are hereby incorporated by reference in their entireties).

In some embodiments, the biological or chemical reaction can be performed in a solution or a reaction chamber that is in contact with, operatively coupled, or capacitively coupled to a FET such as a chemFET or an ISFET. The FET (or chemFET or ISFET) and/or reaction chamber can be an array of FETs or reaction chambers, respectively.

In some embodiments, a biological or chemical reaction can be carried out in a two-dimensional array of reaction chambers, wherein each reaction chamber can be coupled to a FET, and each reaction chamber is no greater than 10 $\mu m^3$ (i.e., 1 pL) in volume. In some embodiments each chamber is no greater than 0.34 pL, 0.096 pL or even 0.012 pL in volume. A reaction chamber can optionally be no greater than 2, 5, 10, 15, 22, 32, 42, 52, 62, 72, 82, 92, or 102 square microns in cross-sectional area at the top. Preferably, the array has at least $10^2$, $10^3$, $10^4$, $10^5$, $10^6$, $10^7$, $10^8$, $10^9$, or more reaction chambers. In some embodiments, at least one of the reaction chambers is operatively coupled to at least one of the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082, which are incorporated by reference in their entireties.

In one aspect, the disclosed methods, compositions, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006) (which are hereby incorporated by reference in their entireties). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase). Examples of such ion-based nucleic acid sequencing methods and platforms include the Ion Torrent PGM™ or Proton™ sequencer (Ion Torrent™ Systems, Life Technologies Corporation).

In some embodiments, the disclosure relates generally to methods for sequencing nucleic acid templates. In one exemplary embodiment, the disclosure relates generally to a method for obtaining sequence information from polynucleotides, comprising: incorporating a nucleotide at the extendible end of the nucleic acid template; and detecting a non-optical signal indicating the nucleotide incorporation using a sensor that detects by-products (e.g., cleavage products) from the nucleotide incorporation reaction. In some embodiments, methods for sequencing comprise: (a) providing a surface including one or more reaction sites containing a polymerase and a nucleic acid template that has, or is hybridized to, an extendible end; (b) performing a first nucleotide flow by contacting one or more of the reaction sites with a first solution including one or more types of nucleotide; (c) incorporating at least one type of a nucleotide at the extendible end of the nucleic acid template contained within at least one of the reaction sites using the polymerase; and (d) detecting a non-optical signal indicating the nucleotide incorporation using a sensor that is attached or operatively linked to the at least one reaction site. Optionally, the sensor comprises a FET sensor. Optionally, at least one reaction site includes one or more FET sensors. Optionally, the methods employ any one or any combination of nucleotides, nucleotide analogs, and/or terminator nucleotides. Optionally, methods that employ one or more terminator nucleotides for sequencing further include: de-blocking the terminator nucleotide which is incorporated. Optionally, the methods for sequencing further include: performing a second nucleotide flow by contacting one or more of the reaction sites with a second solution including one or more types of nucleotides, where the second solution contains one or more terminator nucleotides, one or more non-terminator nucleotides, or a mixture of both types of nucleotides. Optionally, the methods for sequencing further include: incorporating at least a second nucleotide, where the second nucleotide is a terminator nucleotide or non-terminator nucleotide from the second solution. Optionally, the methods for sequencing further include: detecting a second non-optical signal indicating the second incorporated nucleotide using the sensor that is attached or operatively linked to the at least one reaction site.

In some embodiments, the template-dependent synthesis includes incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, the disclosure relates generally to a method for sequencing a nucleic acid, comprising: disposing the nucleic acid templates into a plurality of reaction chambers, wherein one or more of the reaction chambers are in contact with a field effect transistor (FET). Optionally, the method further includes contacting the nucleic acid templates which are disposed into one of the reaction chambers, with a polymerase thereby synthesizing a new nucleic acid strand by sequentially incorporating one or more nucleotides (e.g., terminator nucleotides or non-terminator nucleotides) into a nucleic acid molecule (e.g., extendible end). Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (isFET) and chemically-sensitive FET (chemFET).

One exemplary system involving sequencing via detection of ionic byproducts of nucleotide incorporation is the Ion Torrent PGM™ or Proton™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ or Proton™ sequencer detects the nucleotide incorporations by detecting the hydrogen ion byproducts of the nucleotide incorporations. The Ion Torrent PGM™ or Proton™ sequencer can include a plurality of nucleic acid templates to be sequenced, each template disposed within a respective sequencing reaction well in an array. The wells of the array can each be coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor can provide output signals indicative of nucleotide incorporation which can be represented as voltage changes whose magnitude correlates with the $H^+$ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of $H^+$ ions in the reaction well, along with a concomitant change in the localized pH. The release of $H^+$ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ or Proton™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

In various exemplary embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of nucleotide addition (which may be referred to herein as "nucleotide flows" from which nucleotide incorporations may result) and washing. The primer may be annealed to the sample or template so that the primer's 3' end can be extended by a polymerase whenever nucleotides complementary to the next base in the template are added. Then, based on the known sequence of nucleotide flows and on measured output signals of the chemical sensors indicative of ion concentration during each nucleotide flow, the identity of the type, sequence and number of nucleotide(s)

associated with a sample nucleic acid present in a reaction region coupled to a chemical sensor can be determined.

In a typical embodiment of ion-based nucleic acid sequencing, nucleotide incorporations can be detected by detecting the presence and/or concentration of hydrogen ions generated by polymerase-catalyzed extension reactions. In one embodiment, templates, optionally pre-bound to a sequencing primer and/or a polymerase, can be loaded into reaction chambers (such as the microwells disclosed in Rothberg et al, cited herein), after which repeated cycles of nucleotide addition and washing can be carried out. In some embodiments, such templates can be attached as clonal populations to a solid support, such as particles, bead, or the like, and said clonal populations are loaded into reaction chambers.

In another embodiment, the templates, optionally bound to a polymerase, are distributed, deposited or positioned to different sites of the array. The site of the array include primers and the methods can include hybridizing different templates to the primers within different sites.

In each addition step of the cycle, the polymerase can extend the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, can be proportional to the number of contiguous identical complementary bases. If the next base in the template is not complementary to the added nucleotide, then no incorporation occurs and no hydrogen ion is released. In some embodiments, after each step of adding a nucleotide, an additional step can be performed, in which an unbuffered wash solution at a predetermined pH is used to remove the nucleotide of the previous step in order to prevent misincorporations in later cycles. In some embodiments, the after each step of adding a nucleotide, an additional step can be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction can be exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, sequencing can be performed according to the user protocols supplied with the PGM™ or Proton™ sequencer. Example 3 provides one exemplary protocol for ion-based sequencing using the Ion Torrent PGM™ sequencer (Ion Torrent™ Systems, Life Technologies, CA).

In some embodiments, the disclosure relates generally to methods for sequencing a population of template polynucleotides, comprising: (a) generating a plurality of amplicons by clonally amplifying a plurality of template polynucleotides onto a plurality of surfaces, wherein the amplifying is performed within a single continuous phase of a reaction mixture and wherein at least 10%, 20%, 30%, 40%, 50%, 60%, 70%, 80%, 90%, or 95% of the resulting amplicons are substantially monoclonal in nature. In some embodiments, a sufficient number of substantially monoclonal amplicons are produced in a single amplification reaction to generate at least 100 MB, 200 MB, 300 MB, 400 MB, 500 MB, 750 MB, 1 GB or 2 GB of AQ20 sequencing reads on an Ion Torrent PGM™ 314, 316 or 318 sequencer. The term "AQ20 and its variants, as used herein, refers to a particular method of measuring sequencing accuracy in the Ion Torrent PGM™ sequencer. Accuracy can be measured in terms of the Phred-like Q score, which measures accuracy on logarithmic scale that: Q10=90%, Q20=99%, Q30=99.9%, Q40=99.99%, and Q50=99.999%. For example, in a particular sequencing reaction, accuracy metrics can be calculated either through prediction algorithms or through actual alignment to a known reference genome. Predicted quality scores ("Q scores") can be derived from algorithms that look at the inherent properties of the input signal and make fairly accurate estimates regarding if a given single base included in the sequencing "read" will align. In some embodiments, such predicted quality scores can be useful to filter and remove lower quality reads prior to downstream alignment. In some embodiments, the accuracy can be reported in terms of a Phred-like Q score that measures accuracy on logarithmic scale such that: Q10=90%, Q17=98%, Q20=99%, Q30=99.9%, Q40=99.99%, and Q50=99,999%. In some embodiments, the data obtained from a given polymerase reaction can be filtered to measure only polymerase reads measuring "N" nucleotides or longer and having a Q score that passes a certain threshold, e.g., Q10, Q17, Q100 (referred to herein as the "NQ17" score). For example, the 100Q20 score can indicate the number of reads obtained from a given reaction that are at least 100 nucleotides in length and have Q scores of Q20 (99%) or greater. Similarly, the 200Q20 score can indicate the number of reads that are at least 200 nucleotides in length and have Q scores of Q20 (99%) or greater.

In some embodiments, the accuracy can also be calculated based on proper alignment using a reference genomic sequence, referred to herein as the "raw" accuracy. This is single pass accuracy, involving measurement of the "true" per base error associated with a single read, as opposed to consensus accuracy, which measures the error rate from the consensus sequence which is the result of multiple reads. Raw accuracy measurements can be reported in terms of "AQ" scores (for aligned quality). In some embodiments, the data obtained from a given polymerase reaction can be filtered to measure only polymerase reads measuring "N" nucleotides or longer having a AQ score that passes a certain threshold, e.g., AQ10, AQ17, AQ100 (referred to herein as the "NAQ17" score). For example, the 100AQ20 score can indicate the number of reads obtained from a given polymerase reaction that are at least 100 nucleotides in length and have AQ scores of AQ20 (99%) or greater. Similarly, the 200AQ20 score can indicate the number of reads that are at least 200 nucleotides in length and have AQ scores of AQ20 (99%) or greater.

EXAMPLES

Examples of enzymatic compositions and methods are directed to controlled in vitro fragmentation of nucleic acids, generation of DNA fragments containing shortened stretches of transposon end sequences, and production of asymmetrically tailed DNA fragments.

Materials and Methods

All enzymes, except stand-alone MuA transposase, and reagents were from MuSeek Library Preparation Kit for Ion Torrent (Cat. No. K1331, Thermo Scientific) unless indicated otherwise.

Stand-alone MuA transposase enzyme was from Thermo Scientific (Cat. No. F-750). All oligonucleotides were synthesized at Metabion.

Transposon ends for Examples 1-3 at a final concentration of 60 µM were prepared by annealing equimolar quantities of primers in annealing buffer (10 mM Tris-HCl (pH 8.0), 1 mM EDTA, 50 mM NaCl):

Cut-key4 (No_nick) and Non-cut-key4 or
Cut-key4 (1Nick45-5), Cut-key4 (2Nick45-5) and Non-cut-key4 or
Cut-key4 (1Nick44-6), Cut-key4 (2Nick44-6) and Non-cut-key4 or
Cut-key4 (1Nick42-8), Cut-key4 (2Nick42-8) and Non-cut-key4 or
Cut-key4 (1Nick40-10), Cut-key4 (2Nick40-10) and Non-cut-key4 or
Cut-key4 (1Nick38-12), Cut-key4 (2Nick38-12) and Non-cut-key4 or
Cut-key4 (1Nick36-14), Cut-key4 (2Nick36-14) and Non-cut-key4 or
Cut-key4 (1Nick34-16), Cut-key4 (2Nick34-16) and Non-cut-key4 or
Cut-key4 (1Nick32-18), Cut-key4 (2Nick32-18) and Non-cut-key4 or
Cut-key4 (1Nick31-19), Cut-key4 (2Nick31-19) and Non-cut-key4 or
Cut-key4 (1Nick23-27), Cut-key4 (2Nick23-27) and Non-cut-key4

Transposon ends for Examples 4-6 at a final concentration of 40 µM were prepared by annealing equimolar quantities of primers in annealing buffer (10 mM Tris-HCl (pH 8.0), 1 mM EDTA, 50 mM NaCl):

Cut-key4 (No_nick) and Non-cut-key4 or
Cut-key4 (1Nick 38-12), Cut-key4 (2Nick 38-12) and Non-cut-key4 or
Cut-key4 (1Gap 42-6), Cut-key4 (2Gap 42-6) and Non-cut-key4 or
Cut-key4 (1Gap 40-8), Cut-key4 (2Gap 40-8) and Non-cut-key4 or Annealing of oligonucleotides was accomplished by using the PCR instrument Eppendorf Mastercycler ep Gradient S (Eppendorf) and the following program: 95° C. for 5 min, 70 cycles each lasting for 40 seconds and gradually decreasing the temperature of the block by 1° C. at the end of each cycle starting from 95° C. and ending with 25° C., followed by incubation at 10° C. until the annealed oligonucleotides were used for complex formation. All oligonucleotide sequences used for transposon end preparation are shown in Table 1 and Table 2.

Table 1 below shows the sequences of oligonucleotides used to form various pre-nicked transposon ends or full length transposon ends as well as sequences of oligonucleotides used for DNA amplification.

| SEQ ID NO | No. | Title | Oligonucleotide sequence |
|---|---|---|---|
| 36 | 1 | Non-cut-key4 | TGCTGAACTGACGCACGAAAAACGCGAAAGCGTTTCACGATAAATGCGAAAAC |
| 35 | 2 | Cut-key4 (No_nick) | GTTTTCGCATTTATCGTGAAACGCTTTCGCGTTTTTCGTGCGTCAGTTCA |
| 3 | 3 | Cut-key4 (1 Nick45-5) | GTTTTCGCATTTATCGTGAAACGCTTTCGCGTTTTTCGTGCGTCA |
| 4 | 4 | Cut-key4 (2 Nick45-5) | GTTCA |
| 5 | 5 | Cut-key4 (1 Nick44-6) | GTTTTCGCATTTATCGTGAAACGCTTTCGCGTTTTTCGTGCGTC |
| 6 | 6 | Cut-key4 (2 Nick44-6) | AGTTCA |
| 7 | 7 | Cut-key4 (1 Nick42-8) | GTTTTCGCATTTATCGTGAAACGCTTTCGCGTTTTTCGTGCG |
| 8 | 8 | Cut-key4 (2 Nick42-8) | TCAGTTCA |
| 9 | 9 | Cut-key4 (1 Nick40-10) | GTTTTCGCATTTATCGTGAAACGCTTTCGCGTTTTTCGTG |
| 10 | 10 | Cut-key4 (2 Nick40-10) | CGTCAGTTCA |
| 11 | 11 | Cut-key4 (1 Nick38-12) | GTTTTCGCATTTATCGTGAAACGCTTTCGCGTTTTTCG |
| 12 | 12 | Cut-key4 (2 Nick38-12) | TGCGTCAGTTCA |
| 13 | 13 | Cut-key4 (1 Nick36-14) | GTTTTCGCATTTATCGTGAAACGCTTTCGCGTTTTT |
| 14 | 14 | Cut-key4 (2 Nick36-14) | CGTGCGTCAGTTCA |
| 15 | 15 | Cut-key4 (1 Nick34-16) | GTTTTCGCATTTATCGTGAAACGCTTTCGCGTTT |
| 16 | 16 | Cut-key4 (2 Nick34-16) | TTCGTGCGTCAGTTCA |
| 17 | 17 | Cut-key4 (1 Nick32-18) | GTTTTCGCATTTATCGTGAAACGCTTTCGCGT |
| 18 | 18 | Cut-key4 (2 Nick32-18) | TTTTCGTGCGTCAGTTCA |
| 19 | 19 | Cut-key4 (1 Nick31-19) | GTTTTCGCATTTATCGTGAAACGCTTTCGCG |

-continued

| SEQ ID NO | No. | Title | Oligonucleotide sequence |
|---|---|---|---|
| 20 | 20 | Cut-key4 (2 Nick31-19) | TTTTTCGTGCGTCAGTTCA |
| 21 | 21 | Cut-key4 (1 Nick23-27) | GTTTTCGCATTTATCGTGAAACG |
| 22 | 22 | Cut-key4 (2 Nick23-27) | CTTTCGCGTTTTTCGTGCGTCAGTTCA |
| 23 | 23 | Primer A | CCATCTCATCCCTGCGTGTCTTCGTGCGTCAGTTCA |
| 24 | 24 | Primer A | CCACTACGCCTCCGCTTTCCTCTCTATGGGCAGTCGGTGATTTCGTGCGTCAGTTCA |
| 25 | 25 | Primer A' | CCATCTCATCCCTGCGTGTC |
| 26 | 26 | Primer P1' | CCACTACGCCTCCGCTTTCCTCTCTATG |

Table 2 below shows the sequences of oligonucleotides used to form full length (native) transposon ends, pre-nicked transposon ends and transposon ends with gaps for DNA fragmentation experiments using MuA transpososome containing nicked and gapped transposon ends (Examples 4-6).

directly shown by fragmenting E. coli genomic DNA using MuA transpososomes formed with several different pre-nicked transposon ends.

MuA transposomes were formed in Complex Assembly Buffer with extra DMSO.

| SEQ ID NO | No. | Title | Oligonucleotide sequence | Purpose of use |
|---|---|---|---|---|
| 36 | 1 | Non-cut-key4 | TGCTGAACTGACGCAC-GAAAAACGCGAA AGCGTTTCACGATAAATGCGAAAAC | All transposons |
| 35 | 2 | Cut-key4 (No_nick) | GTTTTCGCATTTATCGTGAAACGC TTTCGCGTTTTTCGTGCGTCAGT-TCA | Native transposon |
| 29 | 3 | Cut-key4 (1Nick 38-12) | GTTTTCGCATTTATCGTGAAACGC TTTCGCGTTTTTCG | Nick 38-12 transposon |
| 30 | 4 | Cut-key4 (2Nick 38-12) | TGCGTCAGTTCA | Nick 38-12 transposon |
| 31 | 5 | Cut-key4 (1Gap 42-6) | GTTTTCGCATTTATCGTGAAACGC TTTCGCGTTTTTCGTGCG | Gap 42-6 transposon |
| 32 | 6 | Cut-key4 (2Gap 42-6) | AGTTCA | Gap 42-6 transposon |
| 33 | 7 | Cut-key4 (1Gap 40-8) | GTTTTCGCATTTATCGTGAAACGC TTTCGCGTTTTTCGTG | Gap 40-8 transposon |
| 34 | 8 | Cut-key4 (2Gap 40-8) | TCAGTTCA | Gap 40-8 transposon |

Figure 8:
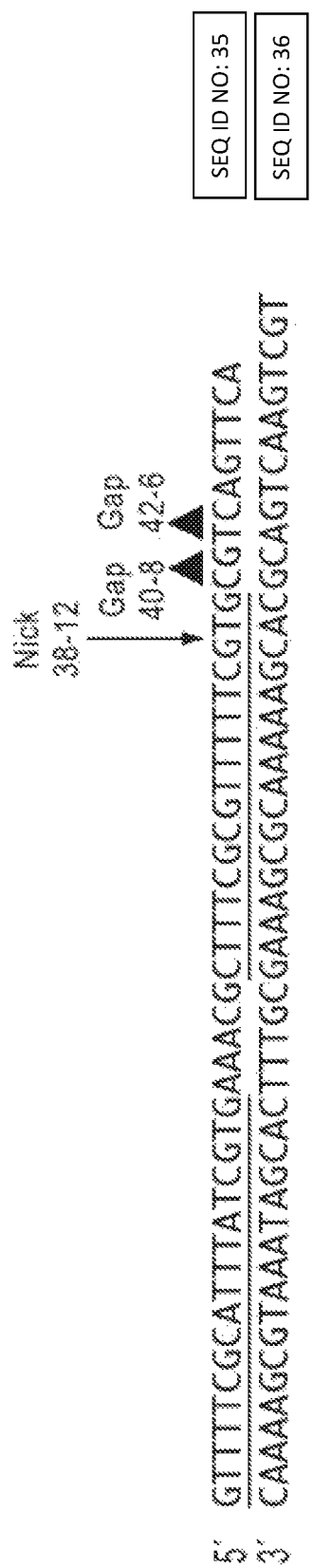
FIG. 8 shows the structure of transposon ends designed for DNA fragmentation experiments using MuA transpososome containing nicked transposon ends and gap-containing transposon ends (examples 4-6).
Figure 9A:
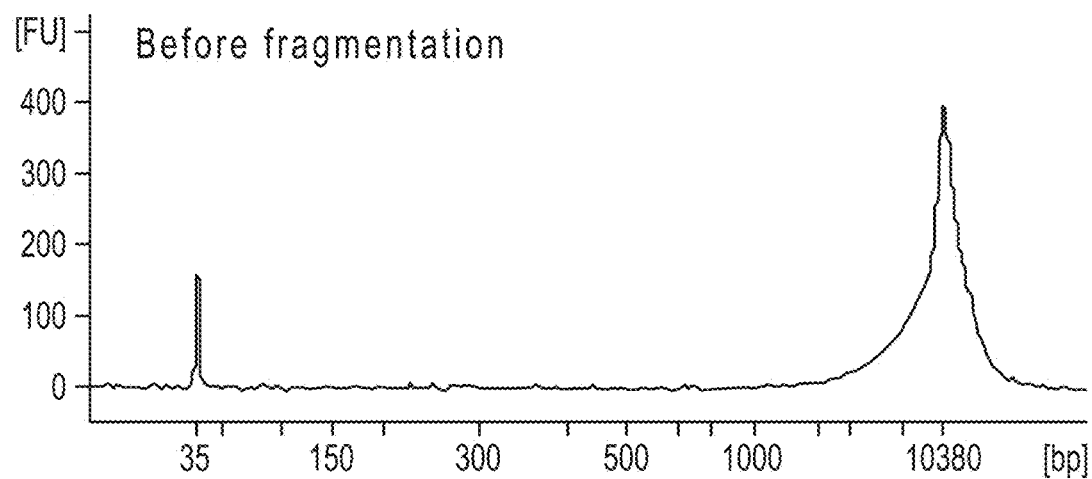
FIG. 9A shows an Agilent 2100 Bioanalyzer curve of *E. coli* gDNA before fragmentation.
Figure 9B:
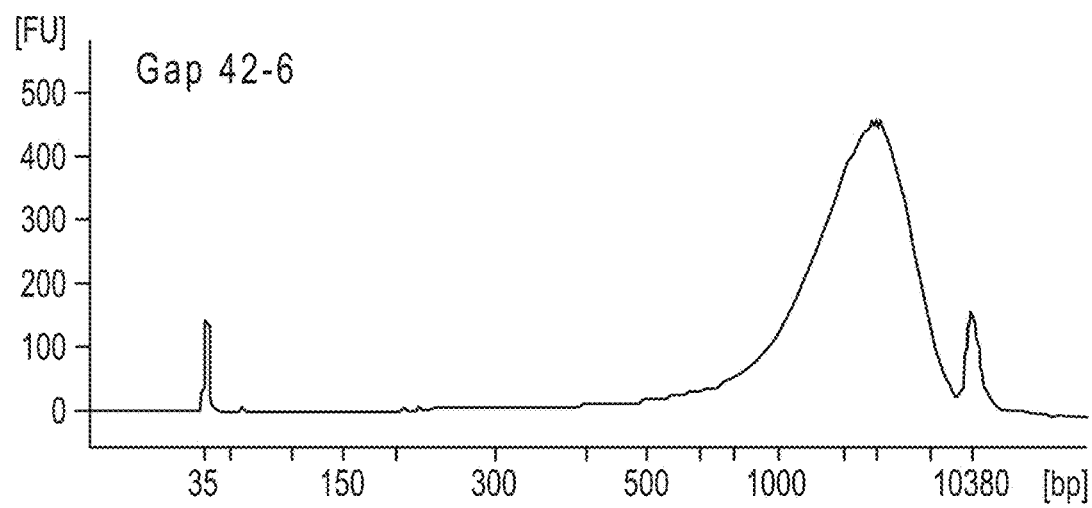
FIG. 9B shows an Agilent 2100 Bioanalyzer curve of *E. coli* gDNA fragmented using MuA transpososomes containing gapped transposon ends (Gap42-6).
Figure 9C:
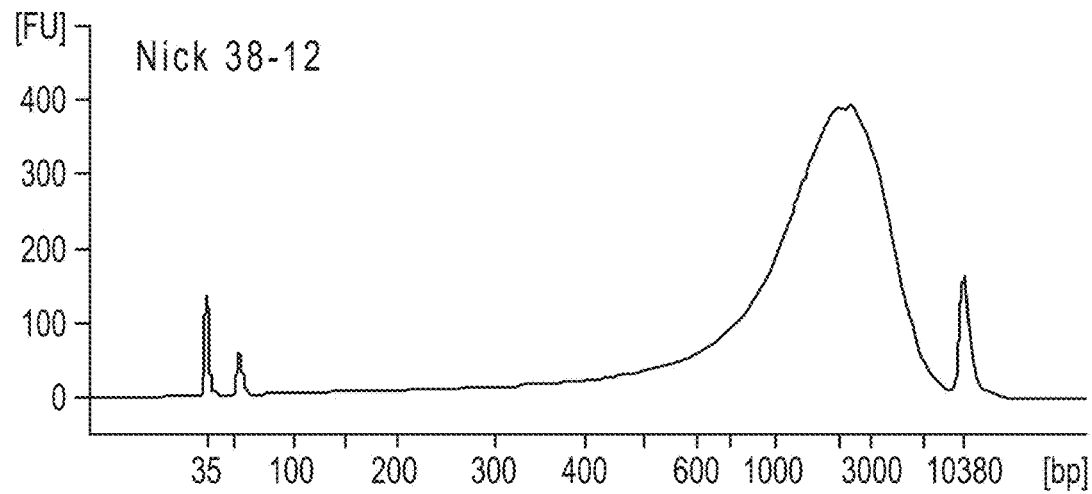
FIG. 9C shows an Agilent 2100 Bioanalyzer curve of *E. coli* gDNA fragmented using MuA transpososomes containing 38-12 nicked transposon ends.
Figure 9D:
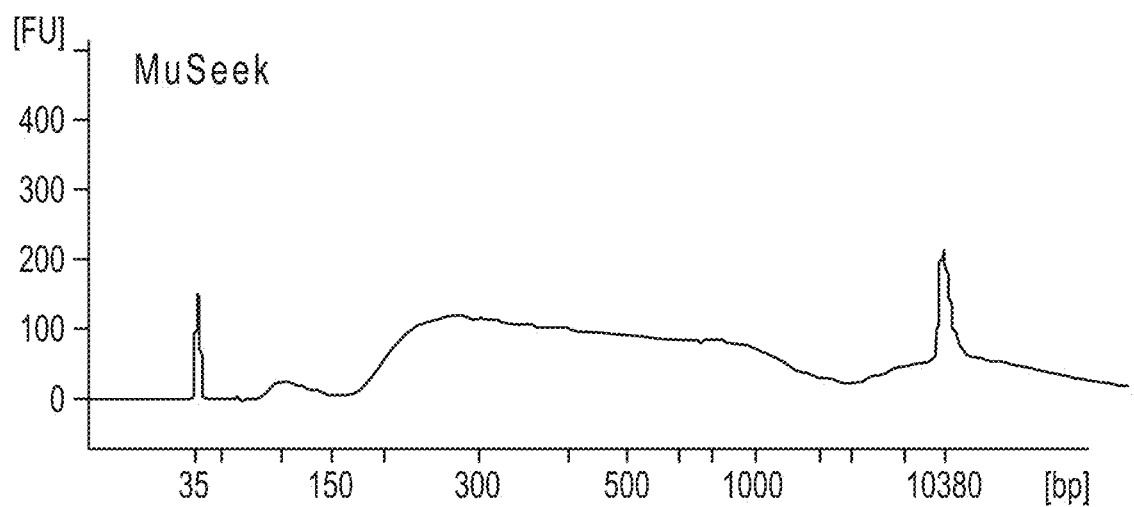
FIG. 9D shows an Agilent 2100 Bioanalyzer curve of *E. coli* gDNA fragmented using MuA transpososomes containing native transposon ends.
Figure 9E:
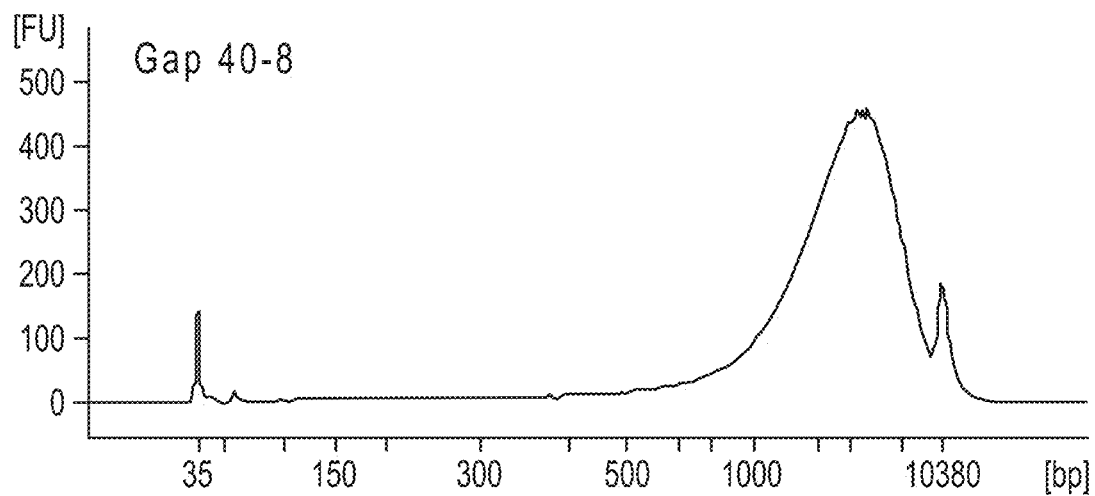
FIG. 9E shows an Agilent 2100 Bioanalyzer curve of *E. coli* gDNA fragmented using MuA transpososomes containing gapped transposon ends (40-8).

FIG. 8 shows the structure of transposon ends designed for experiments in Examples 4-6.

Complex Assembly Buffer is 150 mM Tris-HCl pH 6.0, 50% (v/v) glycerol, 0.025% (w/v) Triton X-100, 150 mM NaCl, 0.1 mM EDTA.

Extra DMSO is 4.6% DMSO at final concentration.

Fragmentation Reaction Buffer is MuSeek Fragmentation Reaction Buffer (Thermo Scientific MuSeek Library Preparation Kit for Ion Torrent™, #K1331) or alternatively 36 mM Tris-HCl (pH 8.0), 137 mM NaCl, 0.05% Triton X-100, 10 mM MgCl$_2$, 4.6% DMSO, and 6.8% glycerol.

Dilution Buffer is 47.2% glycerol, 200 mM NaCl, and 2 mM EDTA at final concentrations.

Example 1

MuA Transposase Forms Catalytically Active Complexes with Pre-Nicked Transposon Ends The ability of MuA transposase to form catalytically active complexes with pre-nicked transposon ends was Final concentration of transposon end was 8 µM and for MuA transposase 1.65 g/l in complex assembly reaction (this is equimolar concentration for MuA transposome formation). After one hour incubation at 30° C., the complex assembly mix was diluted with Dilution Buffer. The final diluted MuA transposome complex concentration was about 0.48 g/l. MuA transposome complex was stored at −70° C. for at least 16 hours before use.

Escherichia coli str. K-12 substr. DH10B gDNA was fragmented using transpososomes made from 10 different pre-nicked transposon ends and one full length (native) transposon end. Each of eleven fragmentation reactions was carried out in separate tube using 100 ng E. coli gDNA in Fragmentation Reaction Buffer. Immediately after adding the transposome mix (1 µl to final reaction volume 30 µl), vortexing, and a short spin-down, the tube was incubated at 30° C. for five minutes. The fragmentation reaction was stopped by adding 3 µl 4.4% SDS. After brief vortexing, the tube was kept at room temperature.

Fragmented DNA was purified by Agencourt AMPure XP PCR Purification (Beckman Coulter) system as follows. Fragmented DNA was transferred into a 1.5 ml tube. Then 49.5 µl of thoroughly mixed Agencourt AMPure XP (Beckman Coulter) beads were added to the reaction and mixed carefully by pipetting up and down ten times. The same procedure was applied to all eleven samples of fragmented DNA. Samples were incubated for five minutes at room temperature. After a short spin, the tubes were placed in a magnetic rack until the solutions were cleared. The supernatant was aspirated carefully without disturbing the beads and discarded. The tubes were kept in the magnetic rack and 400 µl of freshly prepared 70% ethanol was added. After 30 seconds of incubation the supernatant was removed. The ethanol wash step was repeated. The beads were then air-dried by opening the tube caps for two minutes, allowing remaining ethanol to evaporate. The tubes were removed from the magnetic rack, and the beads were suspended in 25 µl of nuclease free water by pipetting up and down ten times. The tubes were then placed back in the magnetic rack and after the solution became clear all 11 supernatants containing the purified fragmented DNA were carefully transferred to new sterile tubes.

The purified fragmented DNAs were analyzed using the Agilent 2100 Bioanalyzer (Agilent Biotechnologies) and the Agilent High Sensitivity DNA Kit (Agilent Biotechnologies) following manufacturer's recommendations. Before analysis, fragmented DNA was diluted by adding equal volume of nuclease free water.

Figures 1, 7A:
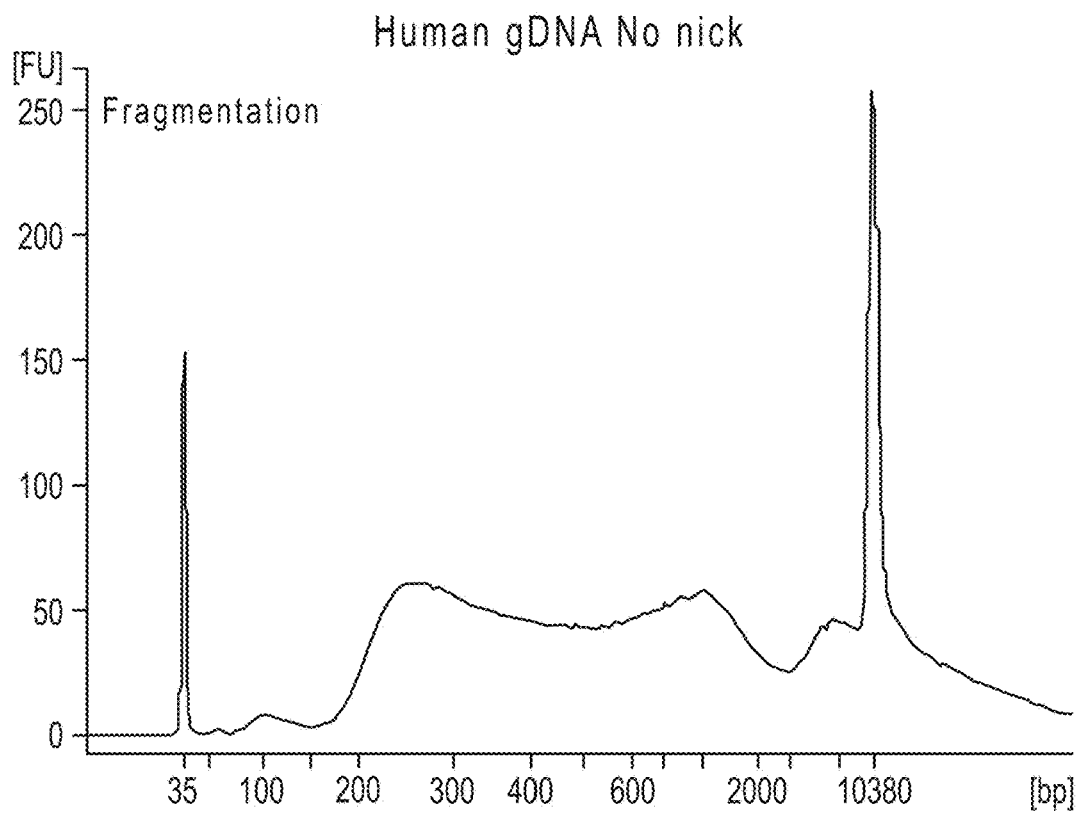
Figures 2, 7A:
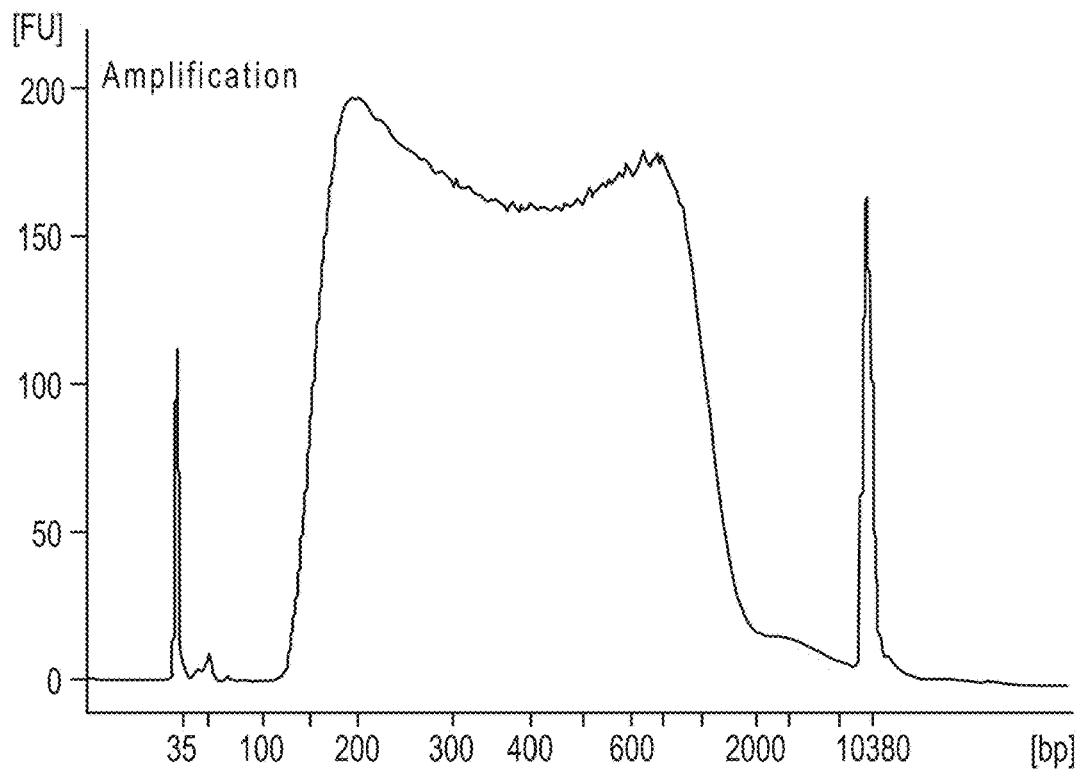
Figures 1, 7B:
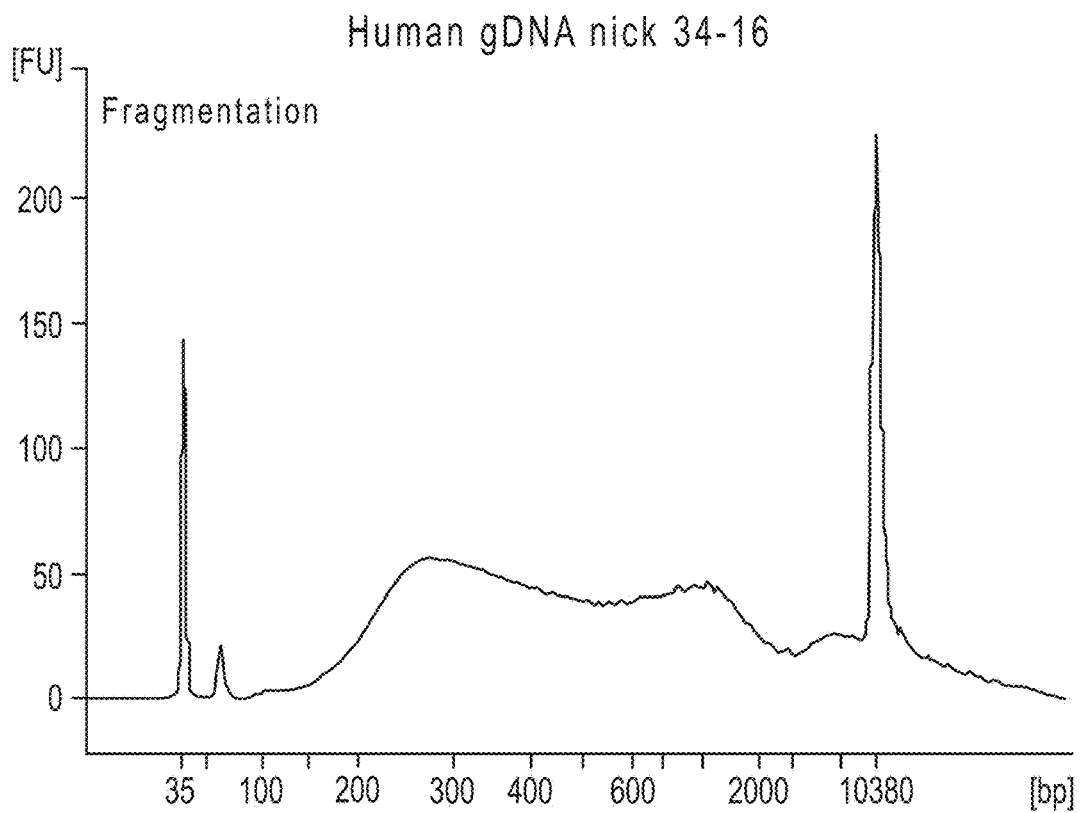
Figures 2, 7B:
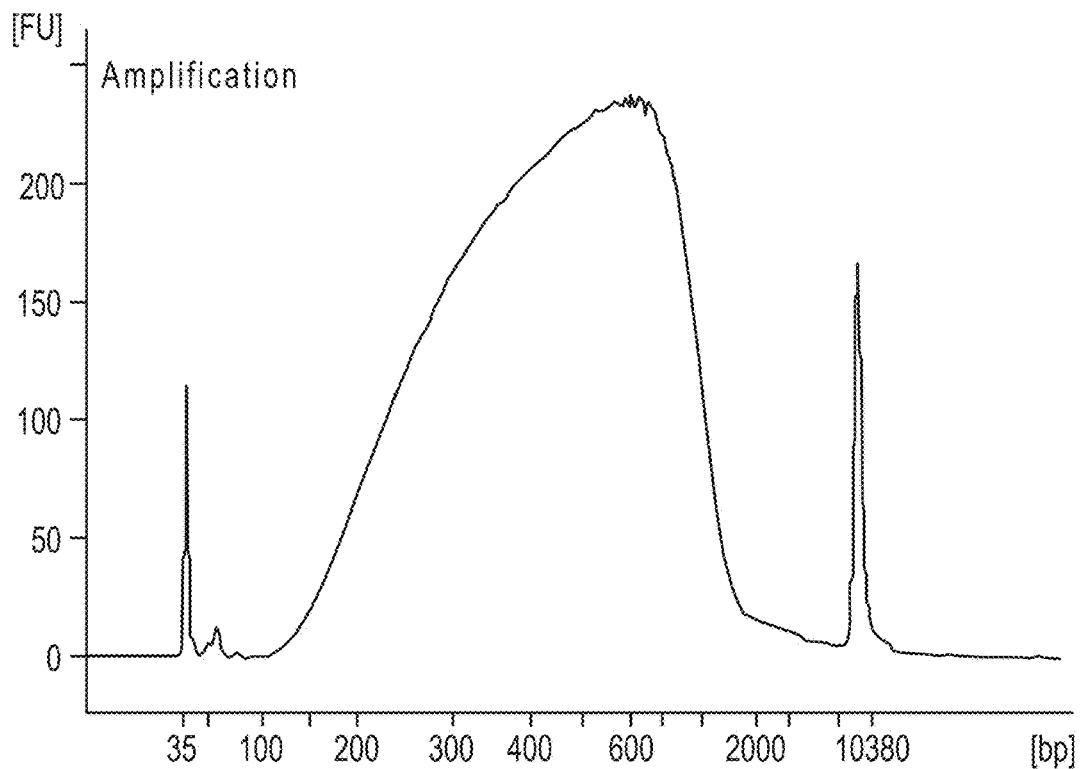

Analysis of fragmentation reaction products (FIG. 2) revealed shortening of gDNA in all cases indicating that transposon ends comprising a nick in general do not interfere with transposase catalytic activity. In vitro transposition reactions resulted in DNA fragments ranging from about 100 bp to 2000 bp in length. Similar curves of DNA fragment length distribution were observed when standard full length transposon end (i.e. native transposon end used for in vitro transposition reaction control) and transposon ends containing nicks after the $6^{th}$, $8^{th}$, $10^{th}$, $14^{th}$, $16^{th}$, $18^{th}$, $19^{th}$, $27^{th}$ positions from the 3' end of Cut-key4 oligonucleotide were used. However, nicks introduced after $5^{th}$ and $12^{th}$ positions from the 3' end of Cut-key4 oligonucleotide reduced DNA fragmentation reaction efficiency.

Example 2

MuA Transposase in Combination with Pre-Nicked Transposon Ends can be Used as a Universal and Well-Controlled DNA Fragmentation Tool Suitable for NGS and Other Molecular Biology Downstream Applications which Require DNA Shearing Versatility of MuA transposase/pre-nicked transposon end fragmentation method was demonstrated by fragmenting various DNA substrates: high complexity human gDNA, double stranded copy DNA made from mRNA isolated from HeLa cells, and three microbial gDNAs differing significantly in their GC content: 50% GC (*Escherichia coli* str. K-12 substr. DH10B), high GC (*Thermus thermophilus* str. HB8) and high AT (*Staphylococcus aureus* str. Mu50). Well-controlled fragmentation was demonstrated by shearing *E. coli* gDNA using varying amounts of MuA transposase-pre-nicked transposon end complex that resulted in distinct, transposome amount dependent average length of DNA fragments. Suitability of DNA fragments resulting after the shearing of DNA of interest with nick containing transposon ends for next generation sequencing was demonstrated using sheared *E. coli* gDNA to prepare Ion Torrent PGM (Life Technologies) compatible DNA library, which was subsequently sequenced to demonstrate run summary segments which indicated good DNA library quality.

Transposon ends (final concentration 60 µM) were prepared by annealing equimolar quantities of primers Cut-key4 (1Nick44-6), Cut-key4 (2Nick44-6) and Non-cut-key4 in 10 mM Tris-HCl (pH 8.0), 1 mM EDTA, 50 mM NaCl and following conditions described in Materials and Methods above.

MuA transposomes were formed in complex assembly buffer with DMSO. The final concentration of transposon end was 8 µM and for MuA transposase 1.65 g/l in complex assembly reaction (this is equimolar concentration for MuA transposome formation). After one hour incubation at 30° C., complex assembly mix was diluted with Dilution Buffer. Final diluted MuA transposome complex concentration was about 0.48 g/l. MuA transposome complex was stored at −70° C. for at least 16 hours before use.

HeLa double stranded copy DNA was synthesized from 500 ng of HeLa mRNA using Maxima H minus Double-Stranded cDNA Synthesis Kit (Thermo Scientific) according to the manufacturer's protocol. After ds cDNA synthesis, the sample was purified using GeneJET PCR Purification Kit (Thermo Scientific) following manufacturer recommendations. Double-stranded cDNA was eluted with 20 µL of elution buffer.

Human gDNA, HeLA double-stranded cDNA, *Escherichia coli* str. K-12 substr. DH10B gDNA, *Thermus thermophilus* str. HB8 and *Staphylococcus aureus* str. Mu50 gDNA were fragmented using the 44-6 pre-nicked transposon end containing MuA transpososome. Fragmentation reactions were carried out in separate tubes using 100 ng of any DNA in fragmentation reaction buffer. Immediately after adding the transposome mix (1 µl to the final reaction volume of 30 µl, or in case of controlled *E. coli* gDNA fragmentation 0.25 µl, 0.5 µl, 1.5 µl and 2 µl to the final reaction volume of 30 µl), vortexing and a short spin-down, the tubes were incubated at 30° C. for five minutes. Subsequently, fragmentation reactions were stopped by adding 3 µl 4.4% SDS. After brief vortexing, tubes were kept at room temperature.

Fragmented DNAs were purified using Agencourt AMPure XP PCR Purification (Beckman Coulter) system. Fragmented DNAs were transferred into 1.5 ml tubes. Then 49.5 µl of thoroughly mixed AMPure XP (Beckman Coulter) beads were added to reaction mixtures and mixed carefully by pipetting up and down for ten times. Samples were incubated for five minutes at room temperature. After a short spin, the tubes were placed in a magnetic rack until the solutions were cleared. The supernatant was aspirated carefully without disturbing the beads and discarded. The tubes were kept in the rack and 400 µl of freshly prepared 70% ethanol was added. After 30 seconds of incubation supernatant was carefully removed, and the same washing procedure repeated. The beads were then air-dried for two minutes, tubes removed from the magnetic rack, and beads resuspended in 25 µl of nuclease-free water by pipetting up and down ten times. The tubes were placed back in the magnetic rack until the solution became clear, and supernatants containing the eluted purified fragmented DNA were transferred to new tubes.

The purified fragmented DNAs were analyzed using the Agilent 2100 Bioanalyzer (Agilent Biotechnologies) and the Agilent High Sensitivity DNA Kit (Agilent Biotechnologies) following manufacturer's recommendations. Before analysis, fragmented DNA was diluted by adding equal volume of nuclease free water.

Intact E. coli gDNA, 1.5 ng, was analyzed on Agilent 2100 Bioanalyzer (Agilent Biotechnologies) as well and served as an uncleaved control.

A library of DNA fragments ready for sequencing on Ion Torrent PGM (Life Technologies) instrument was prepared from 100 ng of E. coli gDNA fragmented with 1.5 µl of MuA transpososome made from pre-nicked transposon end 44-6. Ends of purified DNA fragments were polished and Ion Torrent-compatible adaptors were ligated using ClaSeek Library Preparation Kit (Thermo Scientific) according to the manufacturer's protocol. After adaptor ligation, reaction products were purified and size-selected for 200 bp sequencing using MagJet NGS Cleanup and Size Selection Kit (Thermo Scientific). Size-distribution of resulting DNA fragments before and after adapter ligation was analyzed on Agilent 2100 Bioanalyzer (Agilent Biotechnologies) with results shown in FIG. 5. The DNA library was quantified using Ion Library Quantitation Kit (Life Technologies), sequencing template was prepared using Ion PGM Template OT2 200 Kit (Life Technologies) and subsequently sequenced on Ion Torrent PGM (Life Technologies) using Ion PGM 200 Sequencing Kit (Life Technologies) according to the manufacturer's protocol. The sequencing report was generated with TorrentSuite (Life Technologies) software, version 3.6.

Figure 5:
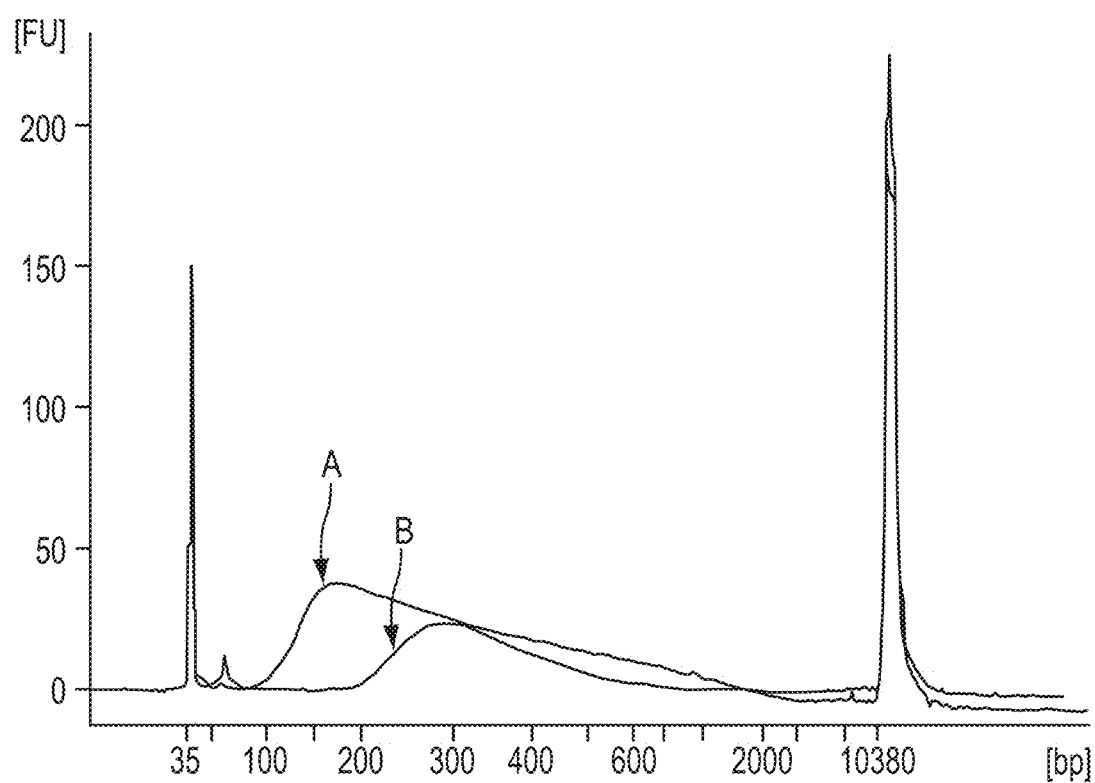
FIG. 5 shows Agilent 2100 Bioanalyzer curves of *E. coli* gDNA fragmented using 44-6 pre-nicked transposon end containing MuA transpososome (curve A) and final size-selected DNA library with ligated adaptors (curve B), used for DNA template preparation and subsequent sequencing on Ion Torrent PGM.
Figure 6A:
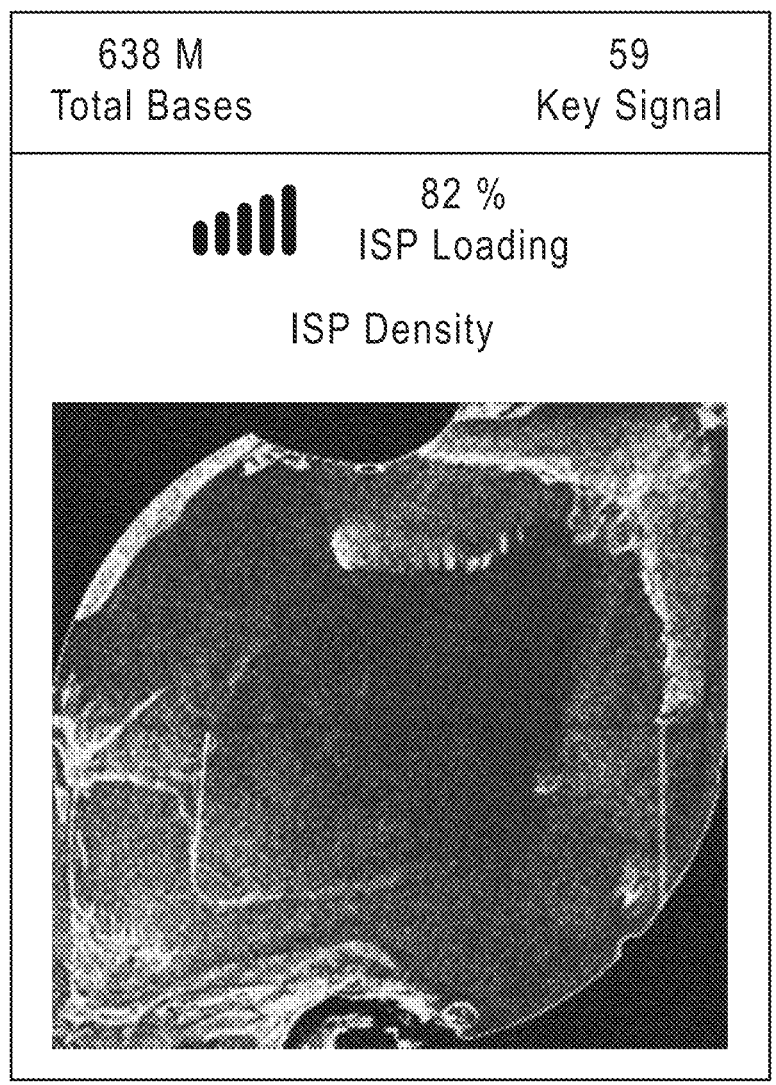
FIG. 6A shows an Ion Torrent PGM DNA library, prepared from *E. coli* gDNA fragmented with 44-6 pre-nicked transposon end containing MuA transpososome, run summary fragments: ISP density MAP.
Figure 6B:
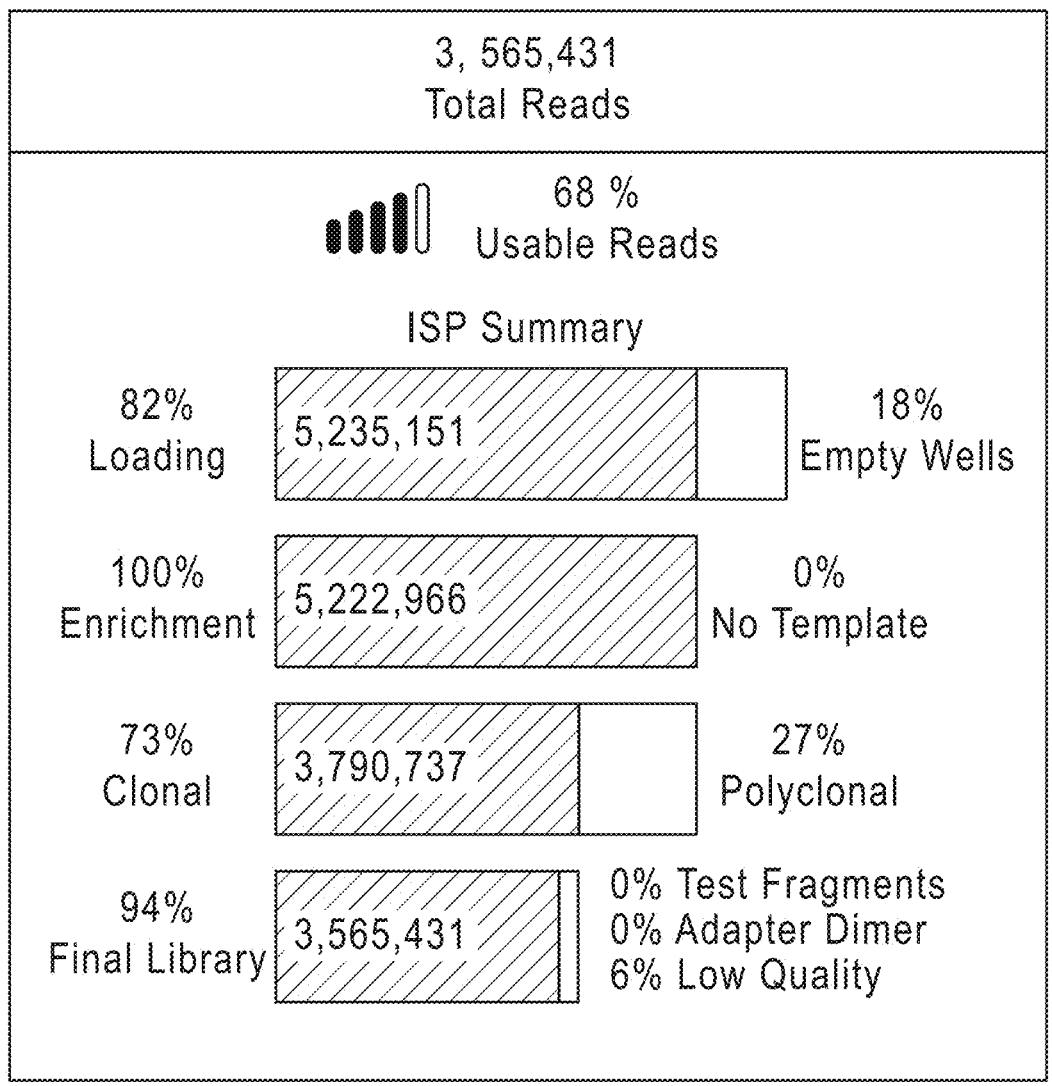
FIG. 6B shows an Ion Torrent PGM DNA library, prepared from *E. coli* gDNA fragmented with 44-6 pre-nicked transposon end containing MuA transpososome, run summary fragments: chip well details.
Figure 6C:
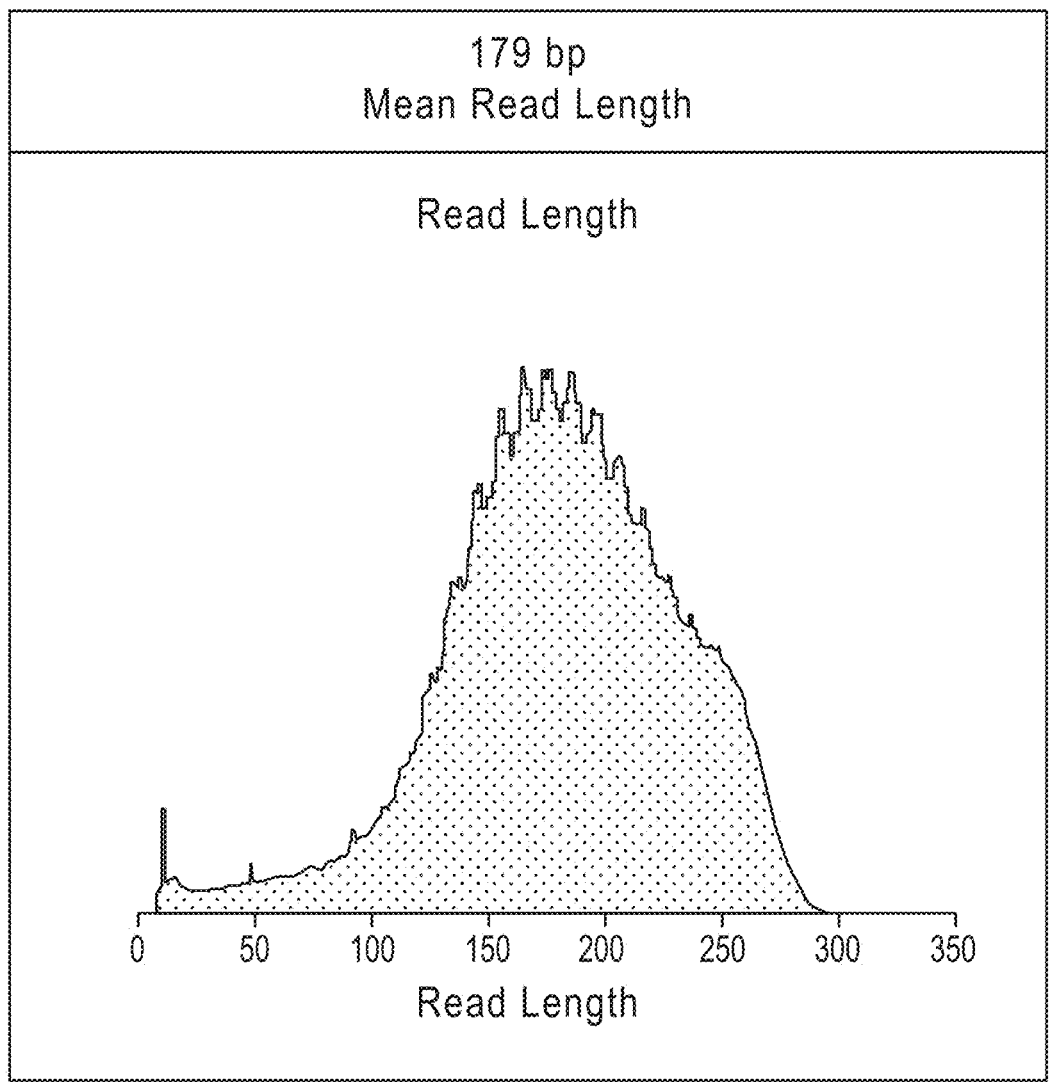
FIG. 6C shows an Ion Torrent PGM DNA library, prepared from *E. coli* gDNA fragmented with 44-6 pre-nicked transposon end containing MuA transpososome, run summary fragments: read length details.
Figure 6D:
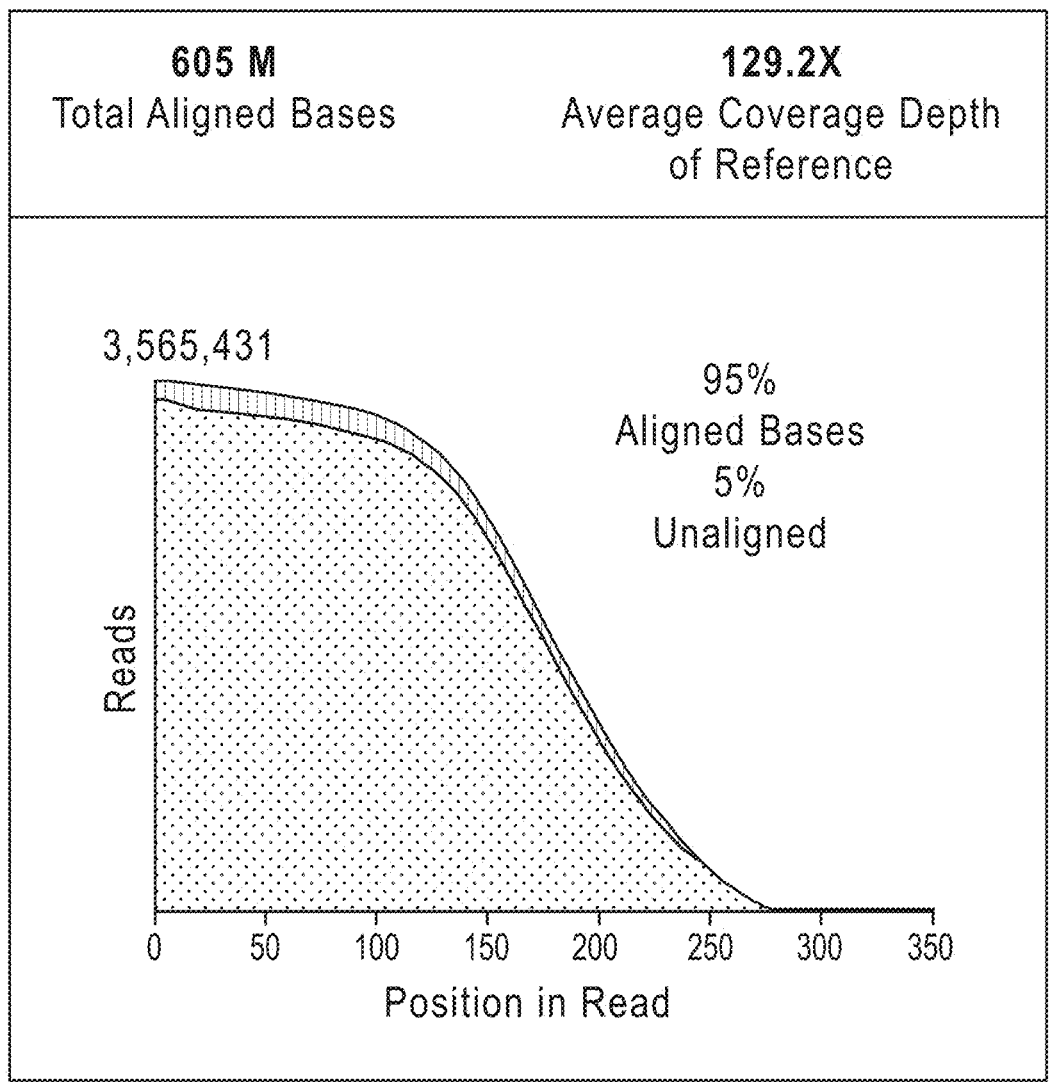
FIG. 6D shows an Ion Torrent PGM DNA library, prepared from *E. coli* gDNA fragmented with 44-6 pre-nicked transposon end containing MuA transpososome, run summary fragments: alignment summary.
Figure 6E:
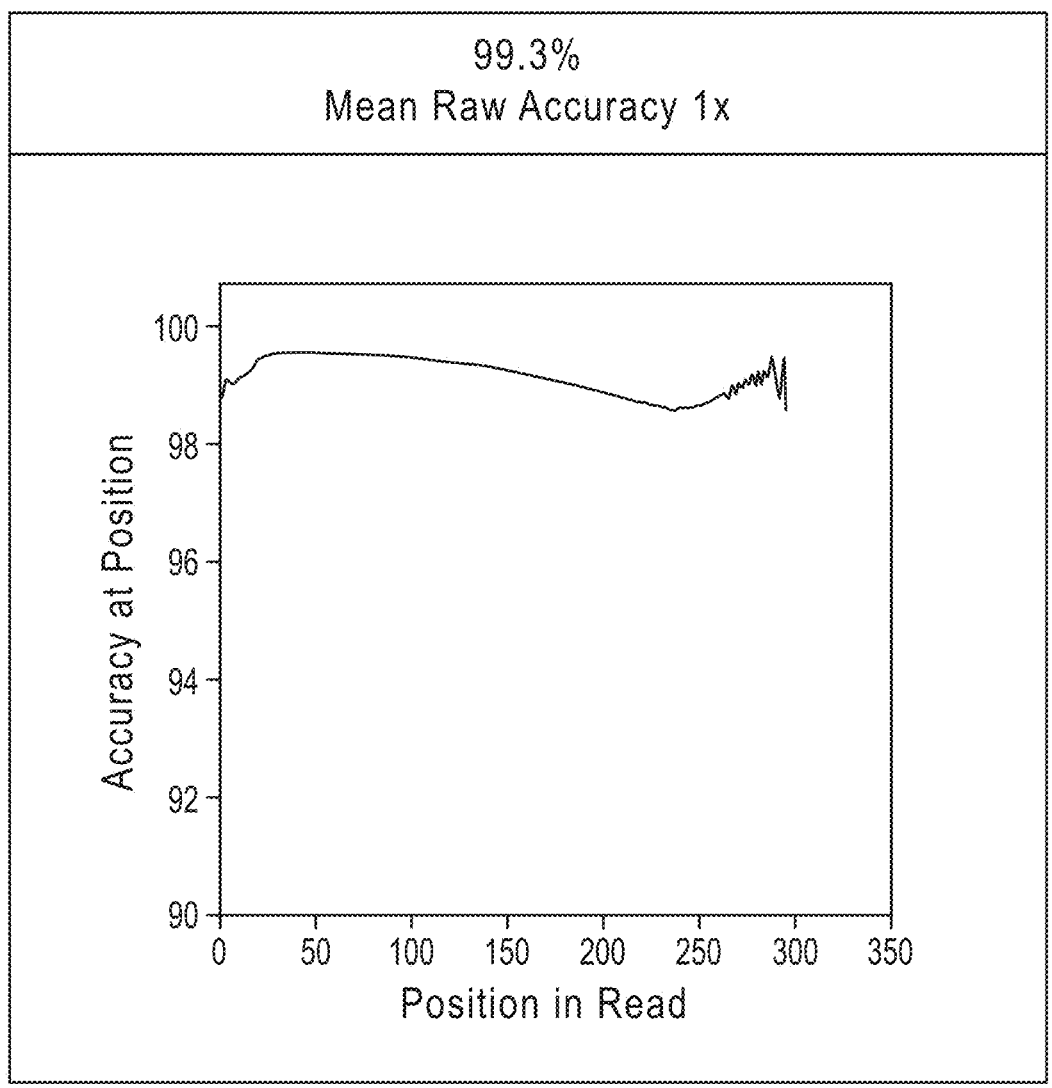
FIG. 6E shows an Ion Torrent PGM DNA library, prepared from *E. coli* gDNA fragmented with 44-6 pre-nicked transposon end containing MuA transpososome, run summary fragments: raw accuracy.
Figures 1, 10A:
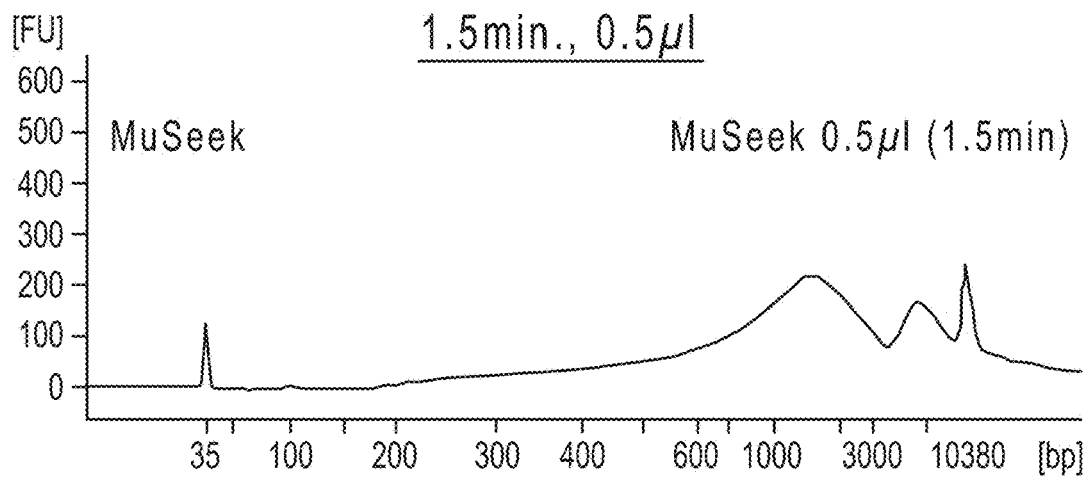
Figures 2, 10A:
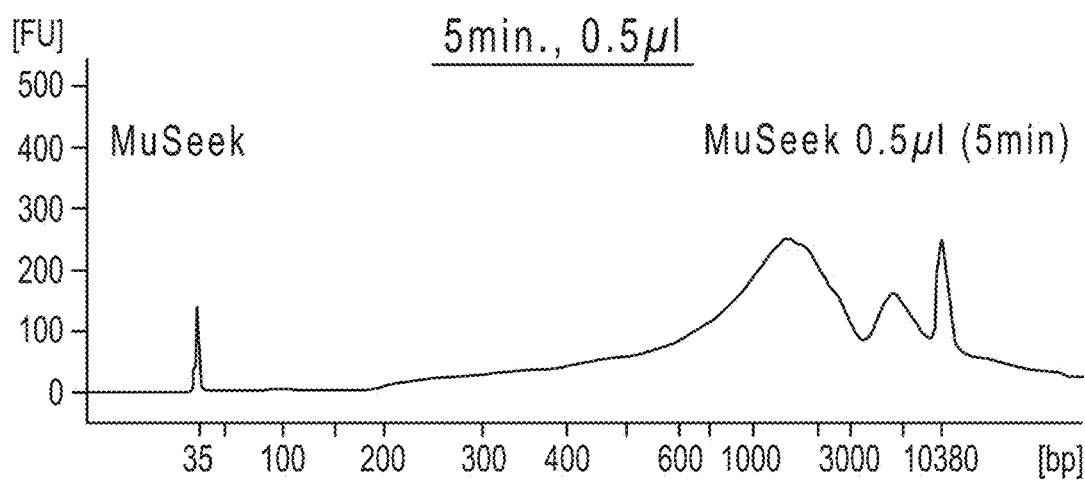
Figures 3, 10A:
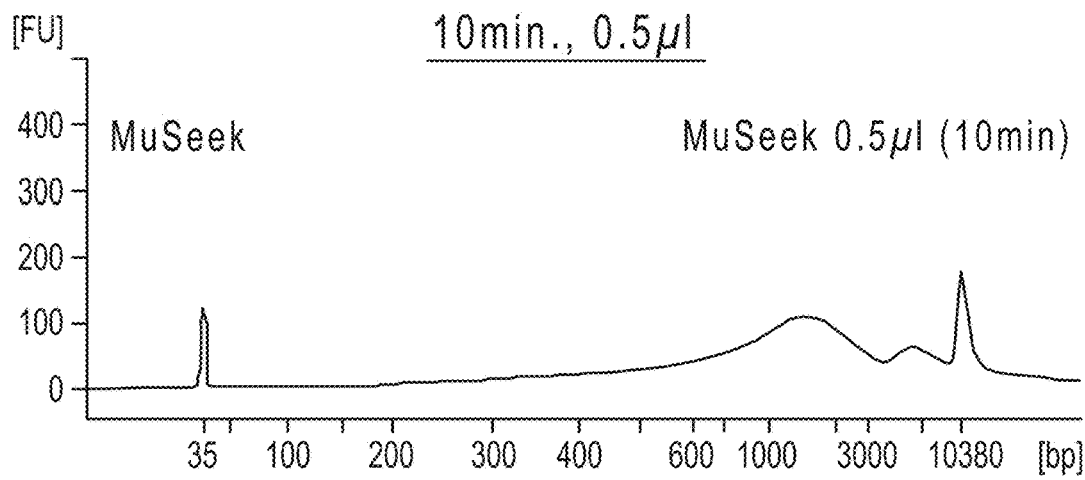
Figures 4, 10A:
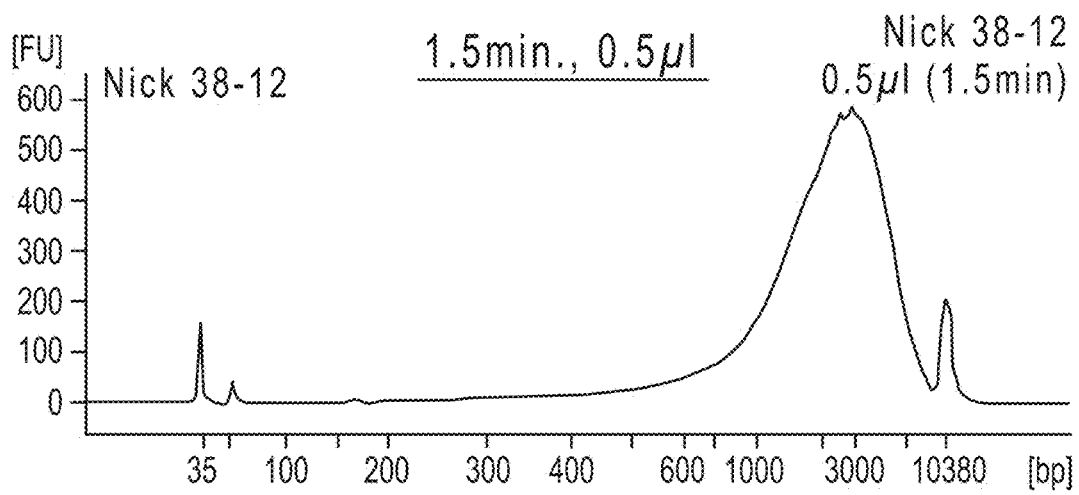
Figures 5, 10A:
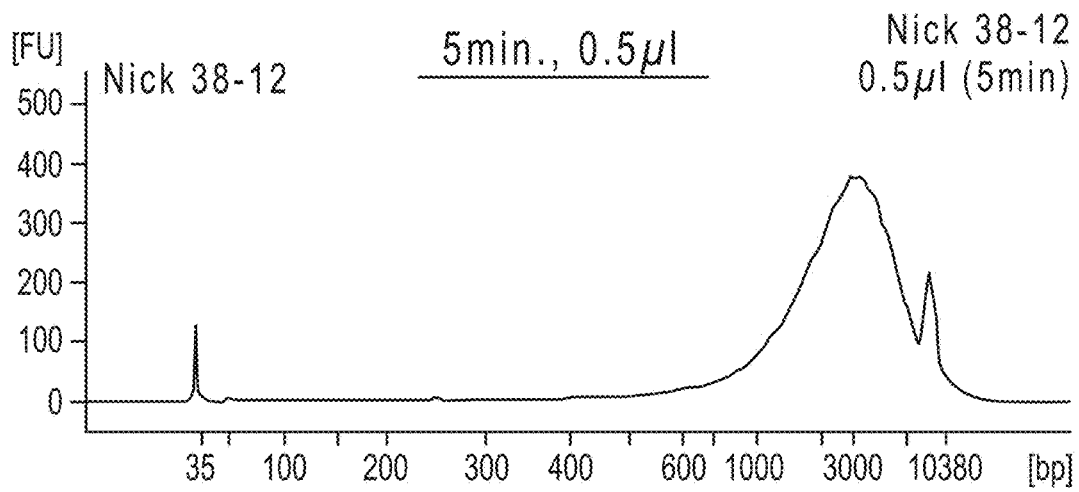
Figures 6, 10A:
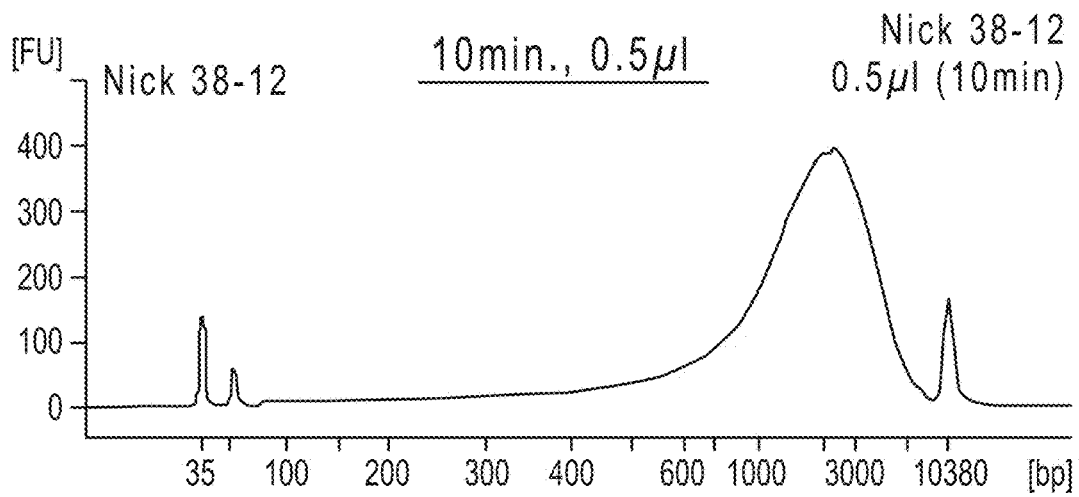

Feasibility of MuA transposase usage in conjunction with pre-nicked 44-6 transposon end as a universal and controlled DNA fragmentation tool was demonstrated with various DNA substrates. Five DNA samples were tested: high complexity human gDNA, double stranded copy DNA made from HeLa mRNA, *Staphylococcus aureus* str. Mu50 gDNA featuring low GC content (33%), *Escherichia coli* str. K-12 substr. DH10B gDNA which GC content is 51%, and *Thermus thermophilus* str. HB8 gDNA (GC content 69%). In all cases fragmentation reactions yielded DNA fragments ranging in length from 100 bp to 2000 bp, as shown in FIG. 3. The ability to adjust the length of shared DNA fragments was demonstrated in *E. coli* gDNA fragmentation experiments. The results indicated that DNA fragmentation level was inversely dependent on the amount of MuA-transposome complex used: adding 0.25 µl cleaved genomic DNA to fragments of 1850 bp on average, 0.5 µl-~800 bp, 1.5 µl-~450 bp, 2 µl-~400 bp shown in FIG. 4. Those skilled in the art will understand that the level of DNA shearing may be manipulated by changing the amount of added transpososome and also by either reducing or increasing the amount of input DNA, and that the level of sharing depends on the integrity of input DNA: in order to achieve the same DNA fragmentation level of very large gDNA fragments one needs to add more transpososome compared to the partially degraded low-quality DNA sample. Sequencing results of *E. coli* gDNA library prepared by using 1.5 µl of transpososome made from the pre-nicked transposon end 44-6 (FIG. 6) revealed good DNA library quality (i.e. small amount of low quality reads, high percentage of aligned reads, high mean raw accuracy), clearly indicating that the DNA shearing approach which exploits pre-nicked transposon ends may be used to prepare high quality DNA libraries for NGS. It is important to note that the pre-nicked transposon end 44-6 used for feasibility studies contains a nick after the 6$^{th}$ position from the 3' end of Cut-key4 oligonucleotide and thus leaves 6 nucleotides at each end of shared DNA which originate from the transposon end. For that reason transposon ends remaining after the polishing of shared DNA fragment ends were trimmed out together with adaptor sequences during sequencing data analysis. This explains why mean sequencing read length (FIG. 6) was ~100 bp shorter than the DNA library used for sequencing (FIG. 5, curve B). Those skilled in the art will understand that the blunt-ended ligation of adapters to polished DNA fragment ends can be easily replaced by sticky-end adapter ligation using specially designed adapters featuring sticky ends which are complementary to those generated by DNA fragmentation with a transpososome made with pre-nicked transposon end.

Example 3

The Use of MuA Transposase in Combination with Pre-Nicked Transposon Ends for DNA Fragmentation Generated DNA Fragments that were Amplified More Efficiently DNA fragments generated using MuA transpososome containing 34-16 pre-nicked transposon end had improved PCR efficiency. This was demonstrated by comparing the outcome of PCR of human gDNA fragmented with the MuA transpososome containing the stated nicked transposon end and the MuA transpososome containing the standard full-length transposon end.

Transposon ends (final concentration 60 µM) were prepared by annealing equimolar quantities of primers Cut-key4 (1Nick34-16), Cut-key4 (2Nick34-16) and Non-cut-key4 or Cut-key4 (No_nick) and Non-cut-key4 in 10 mM Tris-HCl (pH 8.0), 1 mM EDTA, 50 mM NaCl, following the conditions described in Materials and Methods.

MuA transposomes were formed in complex assembly buffer with extra DMSO. The final concentration of transposon end was 8 µM and for MuA transposase 1.65 g/l in the complex assembly reaction. After one hour incubation at 30° C., the complex assembly mix was diluted with dilution buffer. Final diluted MuA transposome complex concentration was about 0.48 g/l. MuA transposome complex was stored at −70° C. for at least 16 hours before use.

Human gDNA was fragmented in parallel with MuA transpososome containing either 34-16 pre-nicked transposon end or a standard full length transposon end. Reactions were performed using 100 ng human DNA in fragmentation reaction buffer. Immediately after adding the transposome mix (1 µl to final reaction volume 30 µl), vortexing and a short spin-down, the tube was incubated at 30° C. for five minutes. The reaction was stopped by adding 3 µl 4.4% SDS. After brief vortexing, the tube was kept at room temperature.

Fragmented DNA was purified using the Agencourt AMPure XP PCR Purification (Beckman Coulter) system following the protocol described in Example 1.

Purified fragmented human gDNAs served as templates for PCR amplification with Phusion Hot Start II High-Fidelity DNA polymerase (Thermo Scientific) and 4 primers: A and P1-Ion platform specific adaptors with transposon end sequences, A' and P1'-PCR amplification primers.

```
                                              (SEQ ID NO: 23)
A    5'-CCATCTCATCCCTGCGTGTCTTCGTGCGTCAGTTCA-3', (SEQ ID NO: 24)
P1   5'-CCACTACGCCTCCGCTTTCCTCTCTATGGGCAGTCGGTGATTT
     CGTGCGTCAGTTCA-3', (SEQ ID NO: 25)
A'   5'-CCATCTCATCCCTGCGTGTC-3', (SEQ ID NO: 26)
P1'  5'-CCACTACGCCTCCGCTTTCCTCTCTATG-3'.
```

Reactions were carried out using 20 μl of fragmented DNA (in final volume of 200 μl) in 10 mM Tris-HCl, pH 8.8, 110 mM KCl, 1.5 mM MgCl$_2$, 0.1% (w/v), Triton X-100, 200 μM dATP, 200 μM dTTP, 200 μM dCTP, 200 μM dGTP using the following cycling conditions: 66° C. 3', 1×98° C. 30"; 9×98° C. 10", 60° C. 50", 72° C. 10"; 1×72° C. 1'.

Amplified DNA was purified using the Agencourt AMPure XP PCR Purification (Beckman Coulter) system. Fragmented DNA was transferred into a 1.5 ml tube. Then 360 μl of thoroughly mixed Agencourt AMPure XP (Beckman Coulter) beads were added to the reaction and mixed carefully by pipetting up and down ten times. Samples were incubated for five minutes at room temperature. After a short spin, the tubes were placed in a magnetic rack until the solutions were cleared. The supernatant was aspirated carefully without bead disruption and discarded. The tubes were kept in the rack and 1000 μl of freshly prepared 70% ethanol was added. After 30 seconds of incubation supernatant was removed. The ethanol wash step was repeated. The beads were air-dried, the tubes removed from the magnetic rack, and the beads were suspended in 20 μl of nuclease-free water by pipetting up and down ten times. The tubes were then placed in the magnetic rack until the solution became clear and supernatants containing the eluted DNA were transferred into new tubes.

DNA samples before and after PCR amplification were analyzed using the Agilent 2100 Bioanalyzer (Agilent Biotechnologies) and the Agilent High Sensitivity DNA Kit (Agilent Biotechnologies). Before analysis, fragmented DNA was diluted with nuclease free water by a factor of 2, while amplified samples by a factor of 4.

Figures 7, 10A:
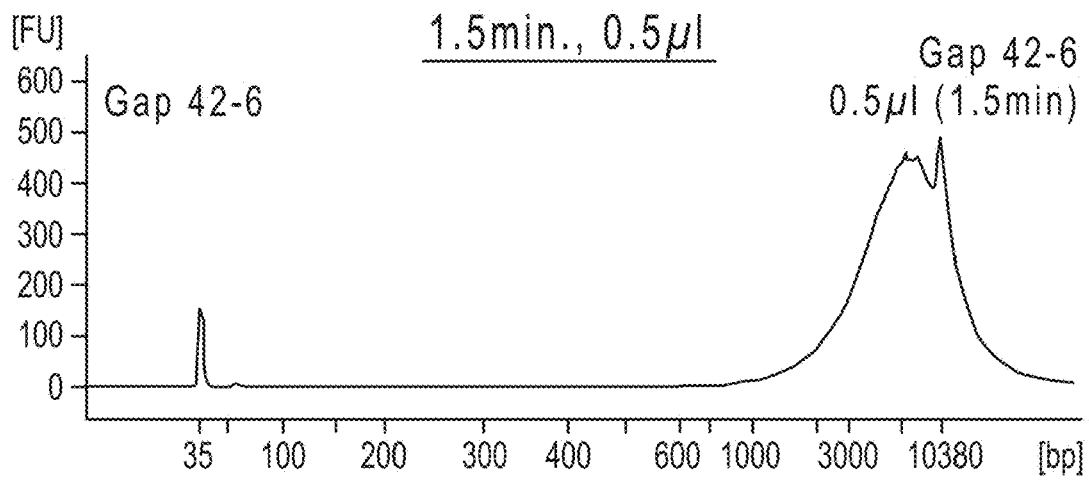
Figures 8, 10A:
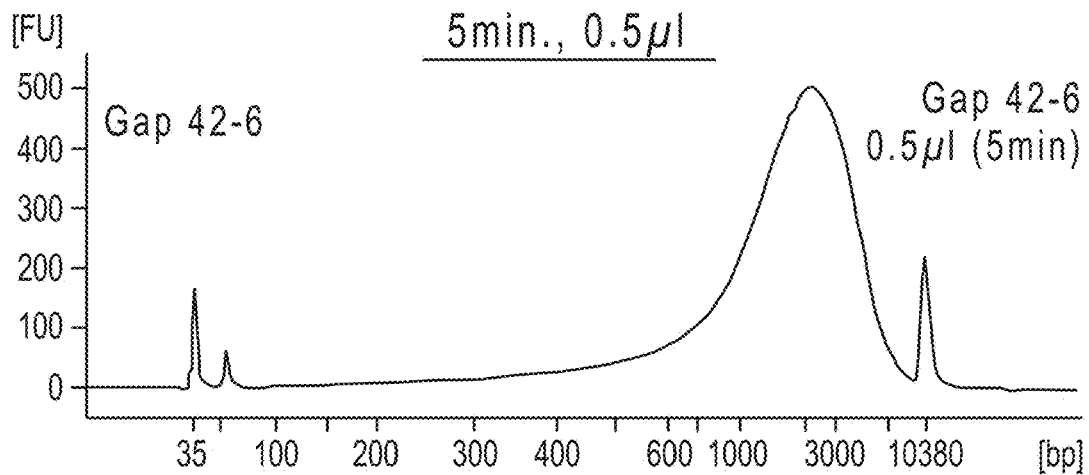

The results are shown in FIG. 7. They revealed differences in PCR amplification outcome among DNA samples analyzed. DNA samples fragmented with MuA transpososome containing the transposon ends having a nick after 16$^{th}$ position (from the 3' end) of Cut-key4 oligonucleotide resulted in reduced amount of short DNA fragments that are unwanted in NGS, thus significantly improving the quality of PCR-amplified DNA library.

Example 4

MuA Transposase Forms Catalytically Active Complexes with Transposon Ends Containing Gap The ability of MuA transposase to form catalytically active complexes with transposon ends containing nucleotide gaps was demonstrated by fragmenting *E. coli* genomic DNA using MuA transpososomes formed with several different transposon ends harboring gap.

Transposon ends at a final concentration of 40 μM were prepared as described in Materials and Methods.

MuA-transposon end complexes (transposon mixes) were formed in complex assembly buffer with extra DMSO. The final concentration of transposon end was 8 μM and for MuA transposase 1.65 g/l in complex assembly reaction (this is equimolar concentration for MuA transposome formation). After one hour incubation at 30° C., complex assembly mix was diluted with dilution buffer. Final diluted MuA-transposon end complex concentration was about 0.48 g/l. MuA-transposon end complex was stored at −70° C. for at least 16 hours before use.

*Escherichia coli* str. K-12 substrate DH10B gDNA was fragmented using MuA transpososomes made from 38-12 pre-nicked transposon end, 42-6 transposon end with gap and 40-8 transposon end with gap or full length native transposon end for use as a control of in vitro transposition reaction, abbreviated in the figures as "MuSeek". Each of four fragmentation reactions was carried out in a separate tube using 100 ng *E. coli* gDNA in fragmentation reaction buffer. Immediately after adding MuA-transposon end complexes (1.5 μl to final reaction volume 30 μl), vortexing and a short spin-down, the tube was incubated at 30° C. for five minutes. The fragmentation reaction was stopped by adding 3 μl of 4.4% SDS. After brief vortexing, the tube was kept at room temperature. Fragmented DNA was purified using GeneJET NGS Purification Kit (Thermo Scientific) and analyzed using Agilent 2100 Bioanalyzer (Agilent Biotechnologies) and Agilent High Sensitivity DNA Kit (Agilent Biotechnologies).

Figures 9, 10A:
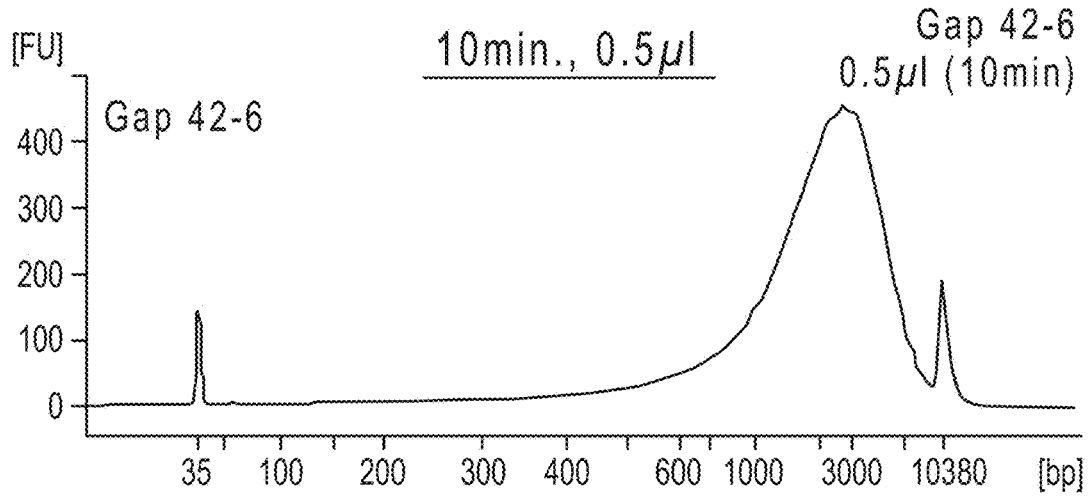
Figures 1, 10B:
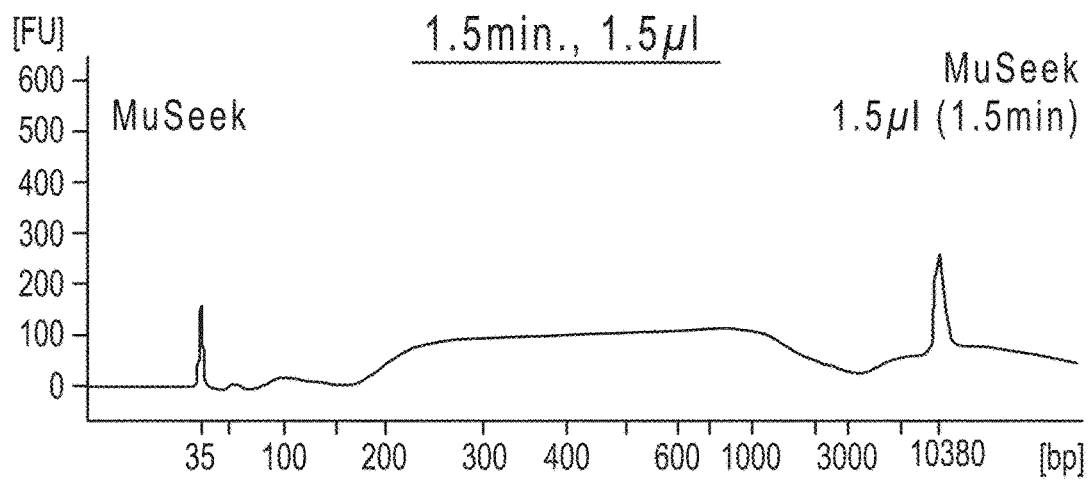
Figures 2, 10B:
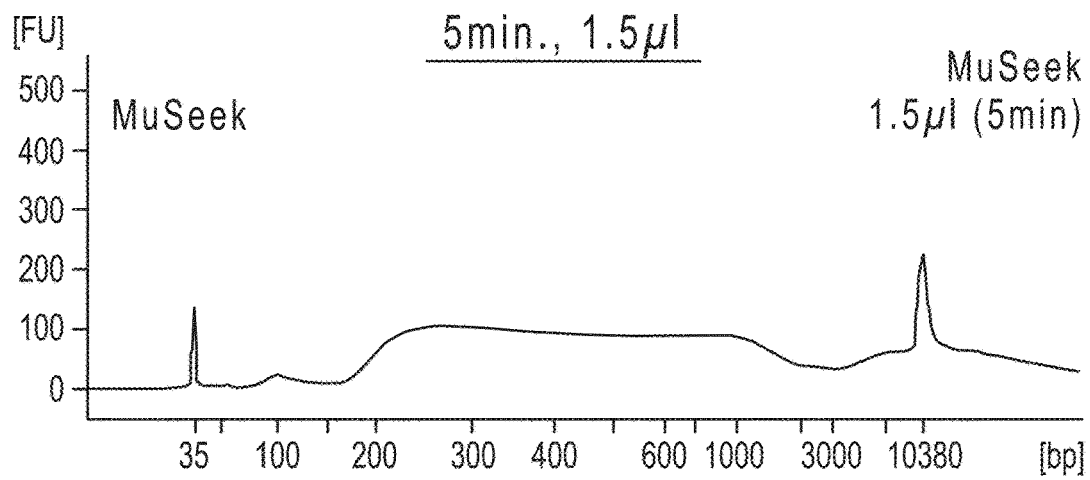
Figures 3, 10B:
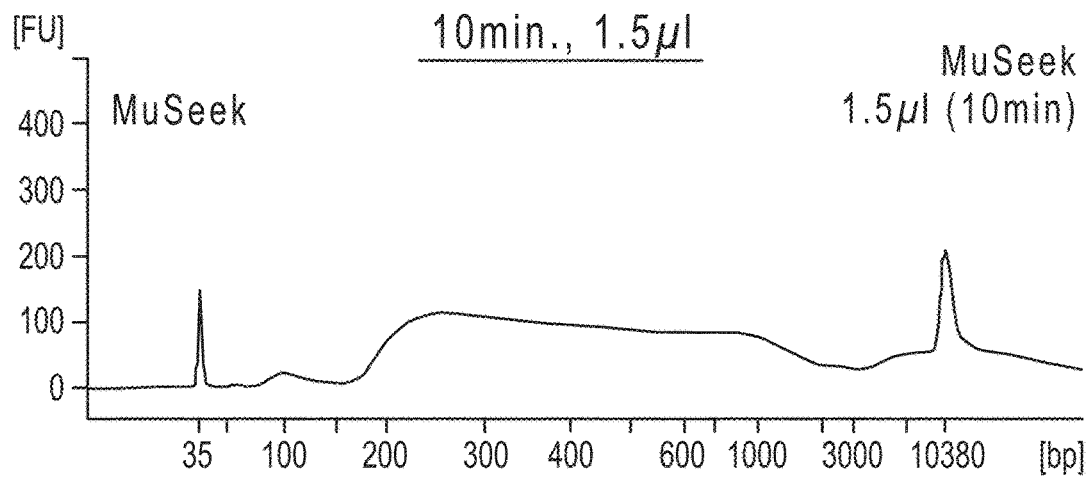
Figures 4, 10B:
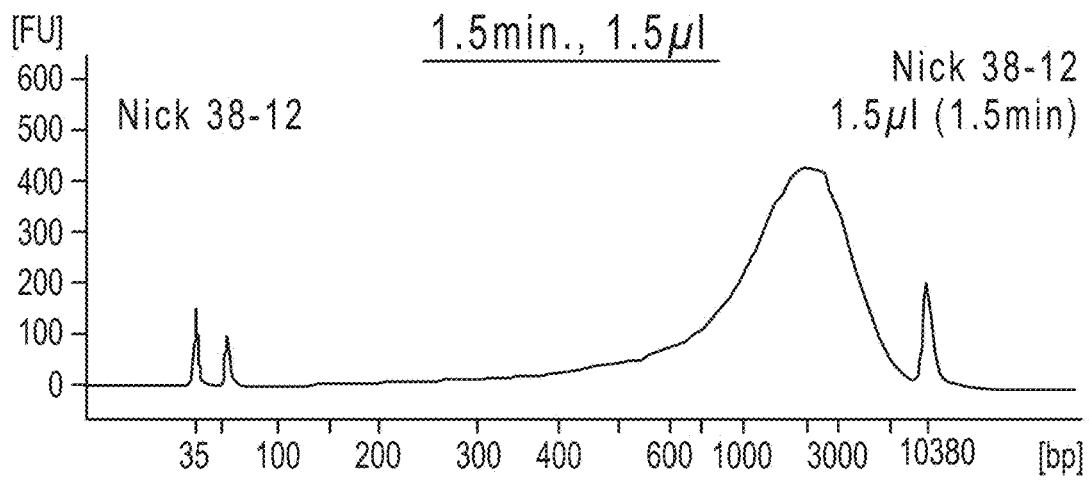
Figures 5, 10B:
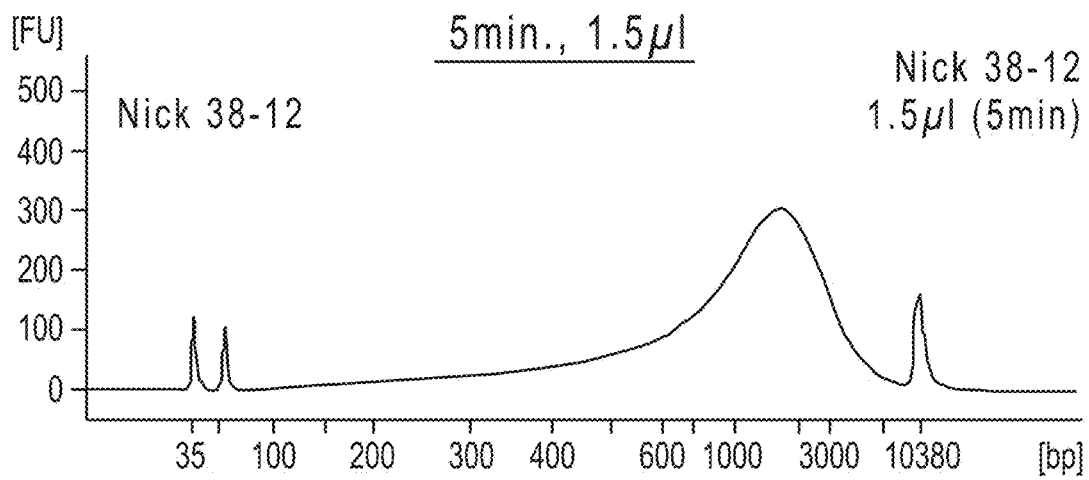
Figures 6, 10B:
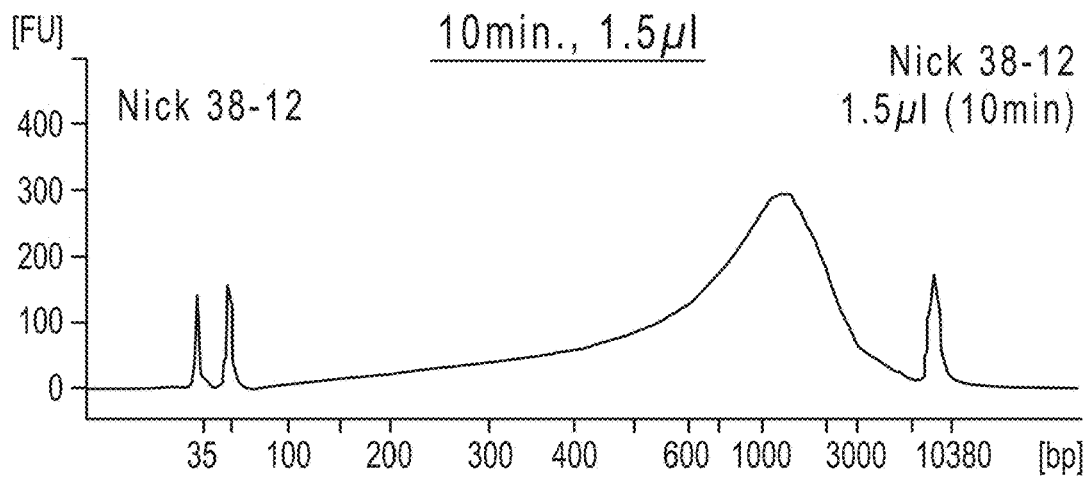
Figures 7, 10B:
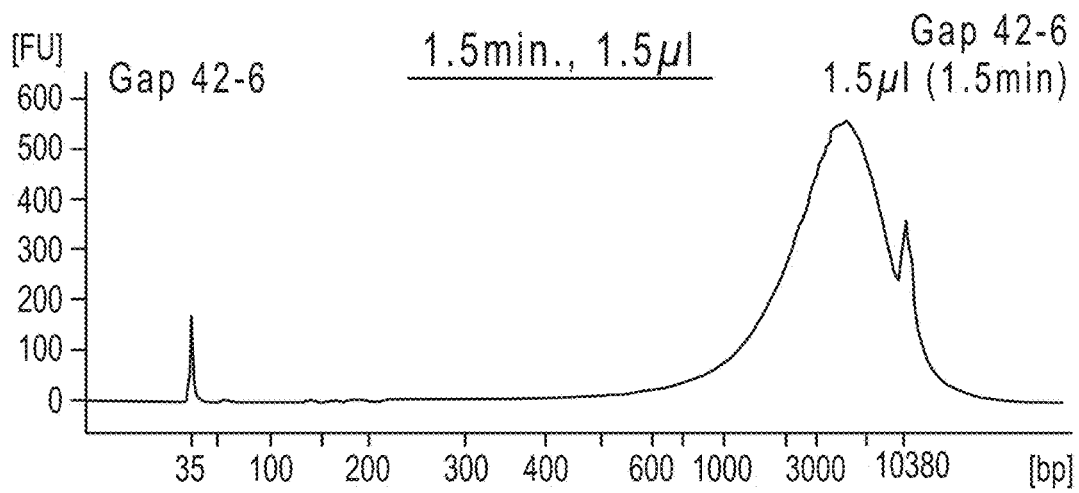
Figures 8, 10B:
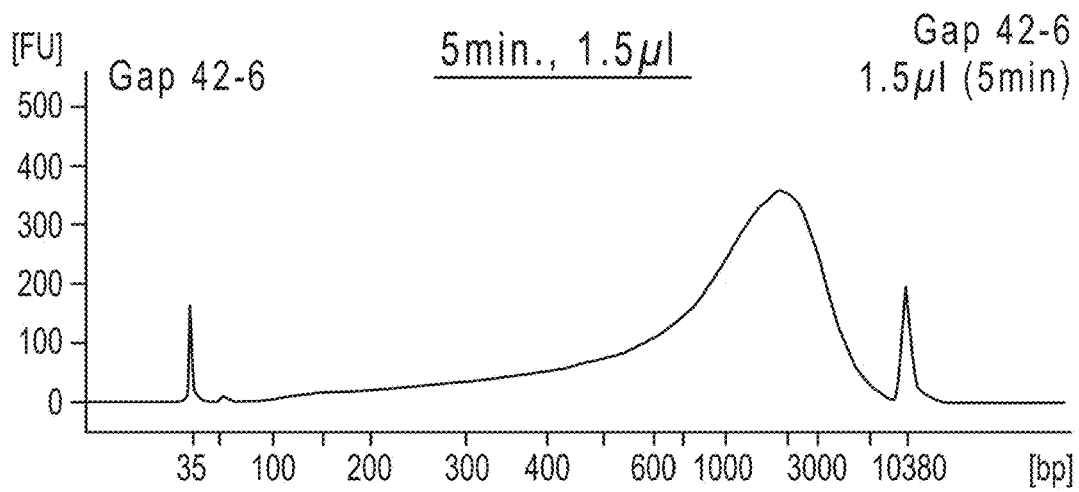
Figures 9, 10B:
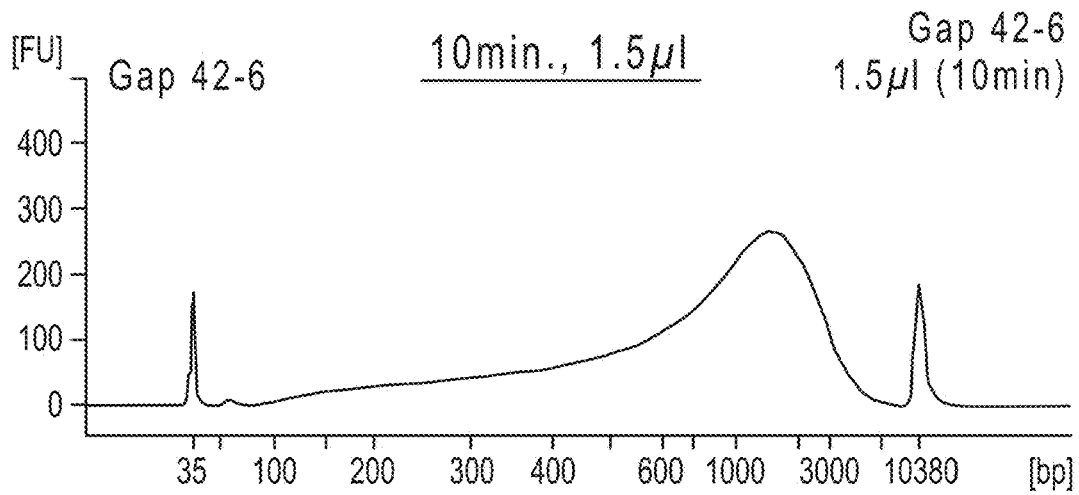
Figure 11A:
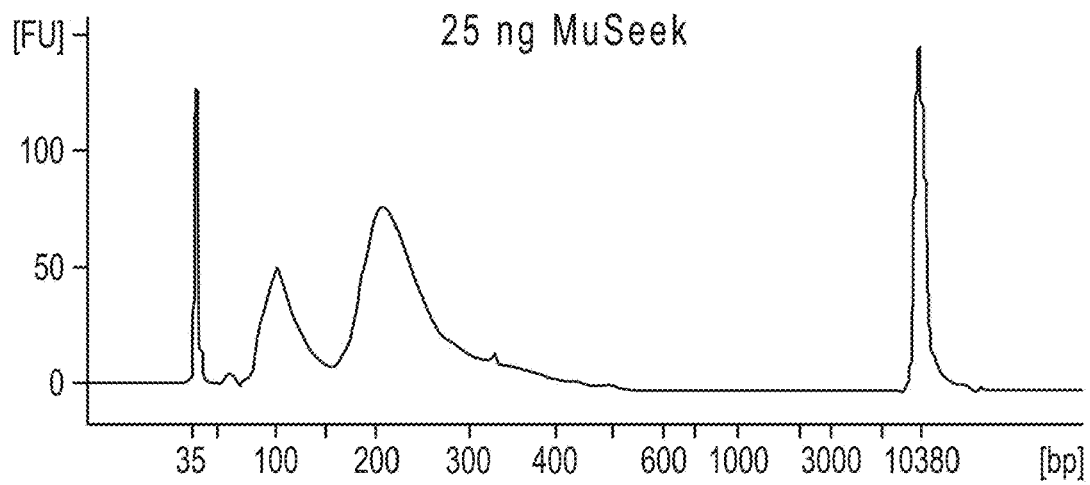
FIG. 11A shows an Agilent 2100 Bioanalyzer curve of fragmented E. coli gDNA illustrating the efficiency of in vitro transposition reaction using fixed amount (1.5 µl) of MuA transpososome containing native transposon end, prolonged in vitro transposition reaction time (30 min), and lower target DNA input (25 ng).
Figure 11B:
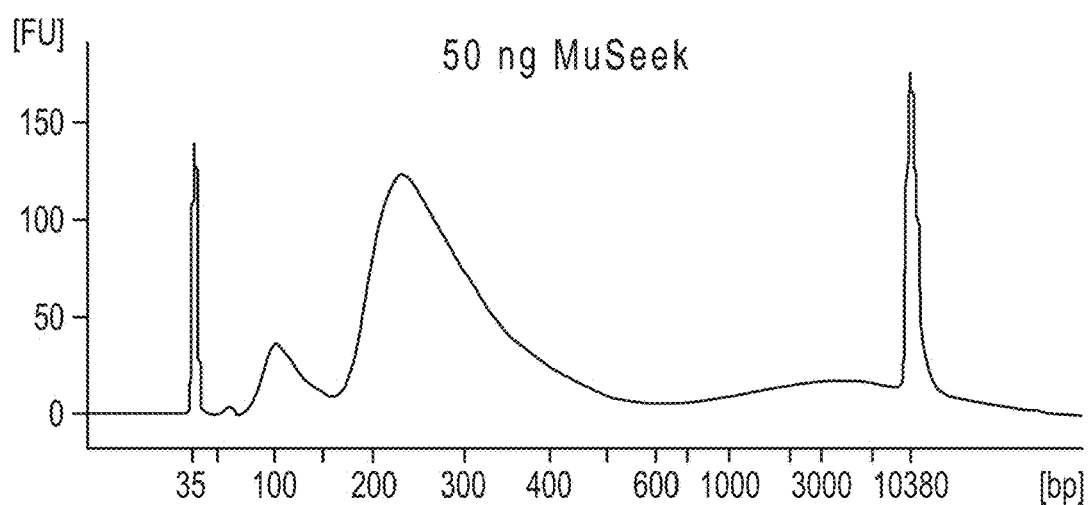
FIG. 11B shows an Agilent 2100 Bioanalyzer curve of fragmented E. coli gDNA illustrating the efficiency of in vitro transposition reaction using fixed amount (1.5 µl) of MuA transpososome containing native transposon end, prolonged in vitro transposition reaction time (30 min), and lower target DNA input (50 ng).
Figure 11C:
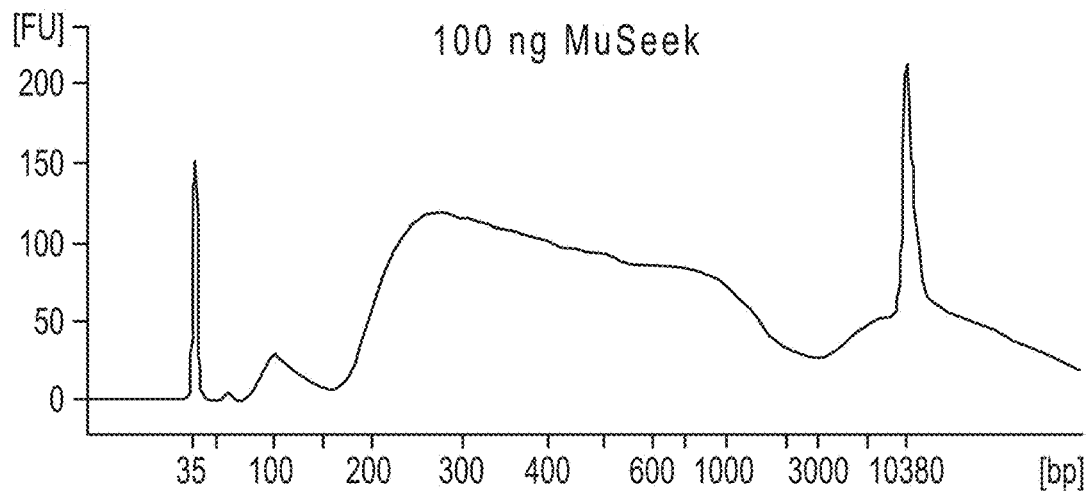
FIG. 11C shows an Agilent 2100 Bioanalyzer curve of fragmented E. coli gDNA illustrating the efficiency of in vitro transposition reaction using fixed amount (1.5 µl) of MuA transpososome containing native transposon end, prolonged in vitro transposition reaction time (30 min), and lower target DNA input (100 ng).
Figure 11D:
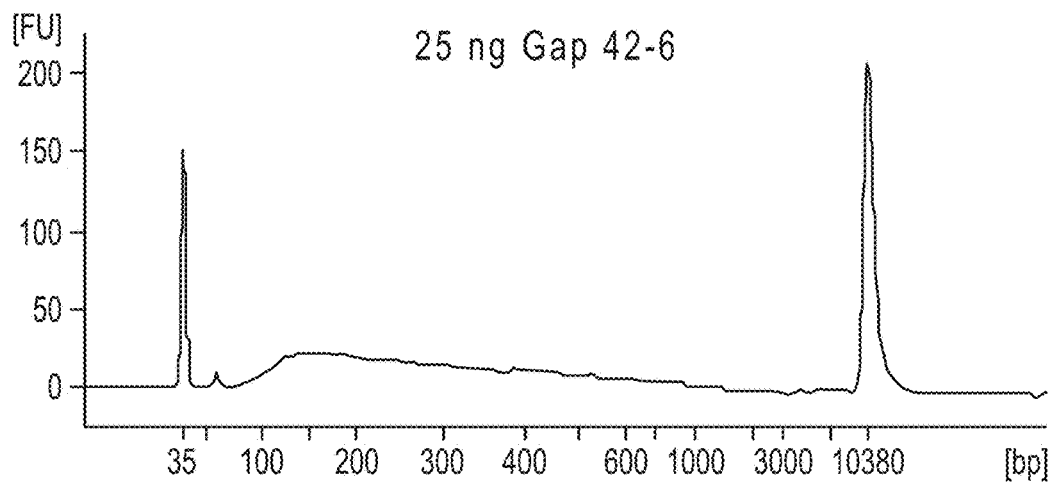
FIG. 11D shows an Agilent 2100 Bioanalyzer curve of fragmented E. coli gDNA illustrating the efficiency of in vitro transposition reaction using fixed amount (1.5 µl) of MuA transpososome containing 42-6 gapped transposon end, prolonged in vitro transposition reaction time (30 min), and lower target DNA input (25 ng).
Figure 11E:
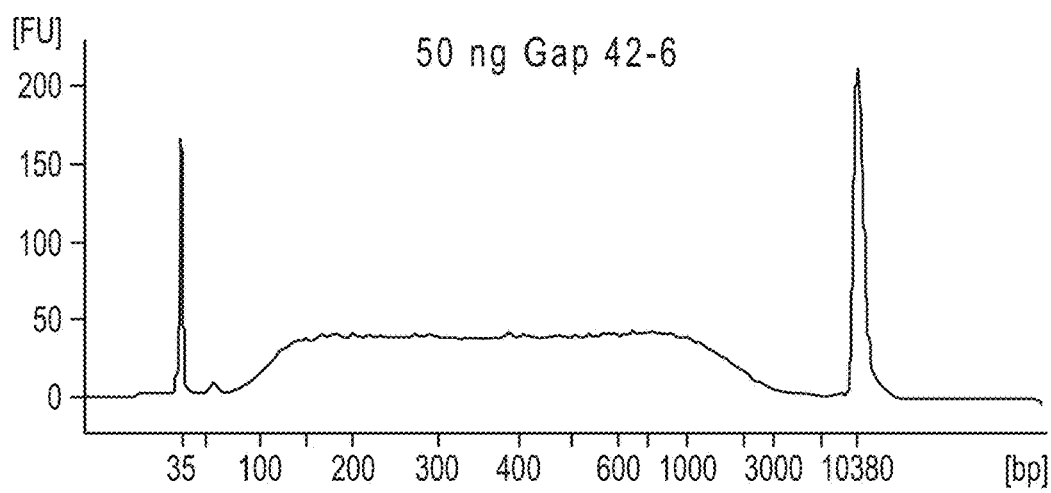
FIG. 11E shows an Agilent 2100 Bioanalyzer curve of fragmented E. coli gDNA illustrating the efficiency of in vitro transposition reaction using fixed amount (1.5 µl) of MuA transpososome containing 42-6 gapped transposon end, prolonged in vitro transposition reaction time (30 min), and lower target DNA input (50 ng).
Figure 11F:
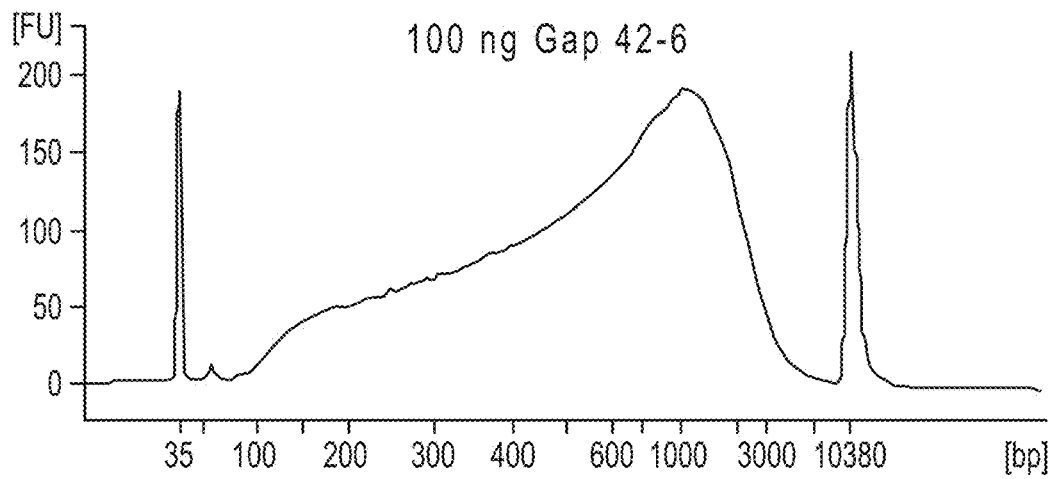
FIG. 11F shows an Agilent 2100 Bioanalyzer curve of fragmented E. coli gDNA illustrating the efficiency of in vitro transposition reaction using fixed amount (1.5 µl) of MuA transpososome containing 42-6 gapped transposon end, prolonged in vitro transposition reaction time (30 min), and lower target DNA input (100 ng).

Results, shown in FIG. 9, demonstrated that MuA transposase formed highly catalytically active complexes with full length native transposon ends, abbreviated in the figure as "MuSeek", resulting in random DNA fragments distributed over a broad range of length. Transposon ends with nucleotide gaps (Gap42-6, Gap 40-8) also formed catalytically active complex with MuA transposase and were able to fragment DNA. DNA fragmentation profile of MuA transposase-gapped transposon end complexes was similar to previous DNA fragmentation experiments using MuA transposase-nicked (38-12) transposon end complexes.

Example 5

MuA Transpososomes Containing Transposon Ends with Gaps can be Used as a Controlled DNA Fragmentation Tool Enabling Generation of DNA Fragments Having Predefined Average Length DNA fragment length dependence on the transposon end structure assembled into MuA transpososome, amount of MuA transpososome, and in vitro transposition reaction time was shown by fragmenting *E. coli* genomic DNA using MuA transpososomes formed with native transposon ends, nicked transposon ends, or transposon ends having nucleotide gaps.

Transposon ends at a final concentration of 40 μM were prepared as described in Materials and Methods.

MuA-transposon end complexes (transposome mixes) were formed in complex assembly buffer with extra DMSO. The final concentration of transposon end was 8 μM and for MuA transposase 1.65 g/l in complex assembly reaction (this is equimolar concentration for MuA transposome formation). After one hour incubation at 30° C., complex assembly mix was diluted with dilution buffer. Final diluted MuA-transposon end complex concentration was about 0.48 g/l. MuA-transposome complex was stored at −70° C. for at least 16 hours before use.

*Escherichia coli* str. K-12 substr. DH10B gDNA was fragmented using MuA transpososomes made from 38-12 pre-nicked transposon ends, 42-6 transposon ends with gap or full length native transposon ends used as control of in vitro transposition reaction, abbreviated in the figures as "MuSeek". Each fragmentation reaction was carried out in separate tube incubating at 30° C. 100 ng of *E. coli* gDNA in fragmentation reaction buffer with different amount (0.5 μl and 1.5 μl in final reaction volume 30 μl) of MuA-transposome complex for different periods of time of 1.5 minutes, 5 minutes, and 10 minutes, respectively. The fragmentation reaction was stopped by adding 3 μl of 4.4% SDS. After brief vortexing, the tube was kept at room temperature. Fragmented DNA was purified using GeneJET NGS Purification Kit (Thermo Scientific) and analyzed using Agilent 2100 Bioanalyzer (Agilent Biotechnologies) and Agilent High Sensitivity DNA Kit (Agilent Biotechnologies).

Figure 12A:
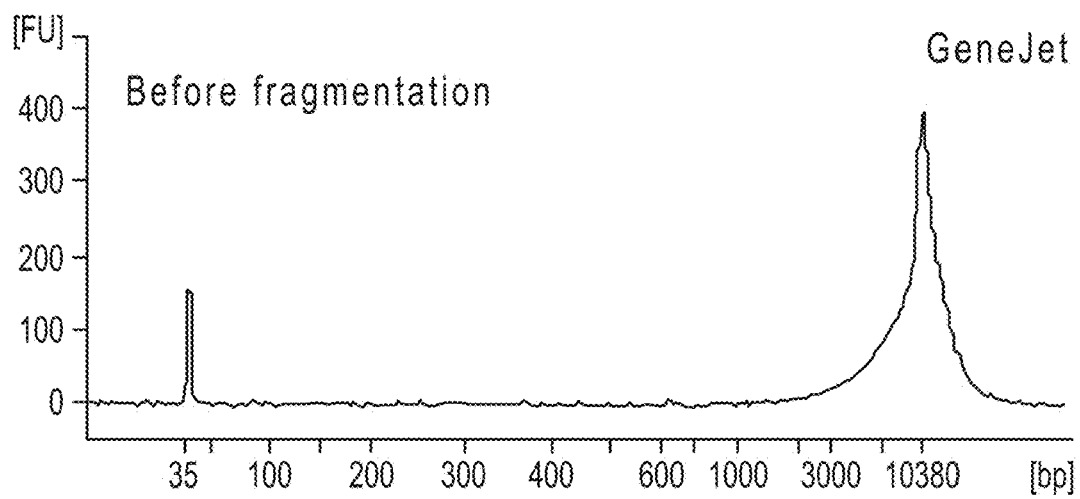
FIG. 12A shows an Agilent 2100 Bioanalyzer curve of E. coli gDNA before fragmentation.
Figure 12B:
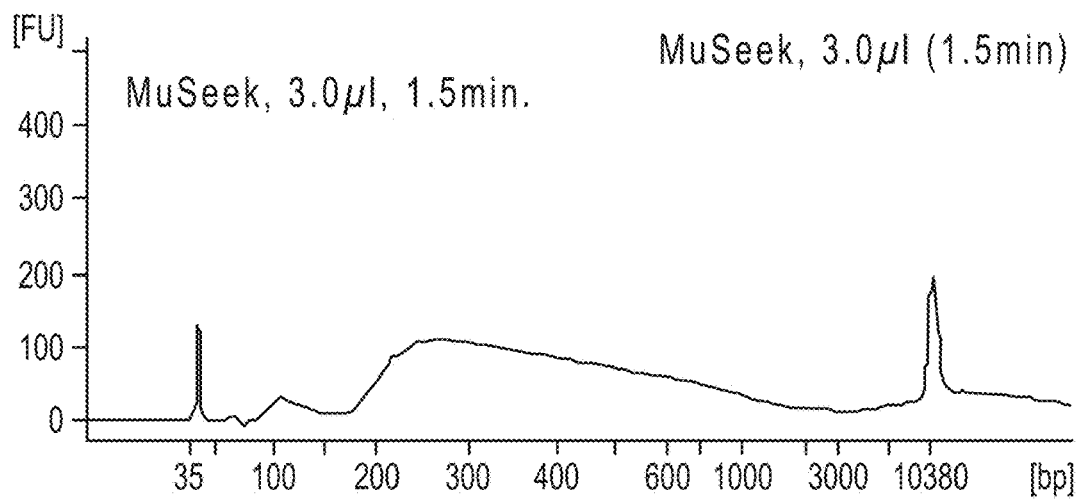
FIG. 12B shows an Agilent 2100 Bioanalyzer curve of fragmented E. coli gDNA illustrating the variable of in vitro transposition reaction time for MuA-native transposon end complex while the amount of input DNA (100 ng) and MuA transpososome (3 µl) containing native transposon end is the same.
Figure 12C:
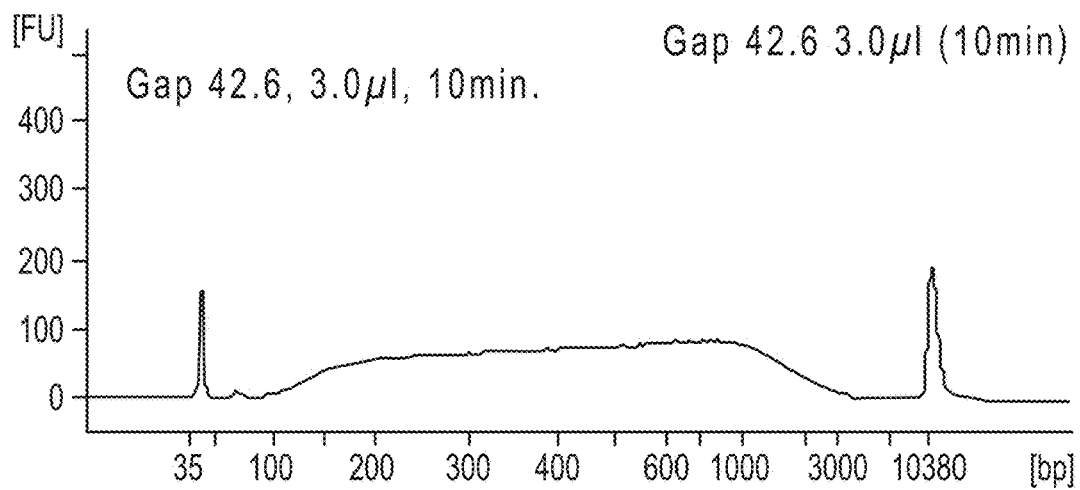
FIG. 12C shows an Agilent 2100 Bioanalyzer curve of fragmented E. coli gDNA illustrating the variable of in vitro transposition reaction time for MuA42-6 transposon end complex while the amount of input DNA (100 ng) and MuA transpososome (3 µl) containing 42-6 gapped transposon end is the same.

Results, shown in FIG. 10, indicated that DNA fragmentation using 1.5 µl of MuA-native transposon end complex at in vitro transposition reaction time of 1.5 min-10 min resulted in random DNA fragments distributed over a broad range of length from about 200 bp to 2000 bp. DNA fragmentation using the same or lower amount of MuA-nicked transposon end (Nick 38-12) complex or MuA-transposon end with gap (Gap 42-6) complex at in vitro transposition reaction of 1.5 min-10 min resulted in specific DNA fragmentation profile, where only DNA fragments of predefined length were generated distributed from about 1 kb to 6 kb. These results support the assumption that DNA fragmentation reaction catalyzed by MuA transpososomes where transposon ends are modified to contain gaps or nicks proceeds slower compared to DNA fragmentation reaction catalyzed by MuA-native transposon end complex. Subsequently, the efficiency of in vitro transposition reaction was investigated using lower DNA input and prolonged incubation time. Amounts of 25 ng, 50 ng and 100 ng of E. coli gDNA were incubated with 1.5 µl of MuA-native transposon end complex and MuA-transposon end with gap (Gap 42-6) complex for 30 min. Fragmented DNA was purified and analyzed as indicated above. Results, shown in FIG. 11, demonstrated that lower amount of DNA input in the fragmentation reaction mixture and prolonged incubation time resulted in the shift of DNA fragmentation reaction products towards shorter length for both MuA-native transposon end complex and MuA-transposon end with gap (Gap 42-6) complex. These results revealed that the length of DNA fragmentation reaction products could be predefined by manipulating the amount of catalytically active MuA-transposon end complex, in vitro transposition reaction time, or DNA input amount. For example, similar DNA fragmentation profiles were achieved for the DNA fragmentation reaction where the amount of input DNA (100 ng) and MuA transpososome (3 µl) containing either native transposon end or 42-6 transposon end with gap was the same by prolonging DNA fragmentation reaction time up to 10 min catalyzed by MuA transpososome containing 42-6 transposon end with gap (FIG. 12).

The examples support the novel teaching of this disclosure, which is based on the observation that transpososomes where transposon ends are modified to contain gaps, nicks, or apurinic/apyrimidinic sites retained their ability to enzymatically shear various DNA substrates, and that gaps, nicks, or apurinic/apyrimidinic sites within the transposon end slowed in vitro transposition reaction rate catalyzed by transposase enzyme. As a result, DNA fragmentation reaction kinetics (i.e. transposase-transposon end complex amount, DNA input amount, and/or DNA fragmentation reaction time) can be adjusted such that only DNA fragments of predefined average length are generated providing for universal and controlled DNA fragmentation.

Example 6

MuA Transposase Forms Catalytically Active Complexes with Modified Transposon Ends Containing Degenerate Sequences and can be Used as a Controlled DNA Fragmentation Tool Enabling Generation of DNA Fragments Having Predefined Average Length A number of transposon end sequences that differ substantially from the wild-type MuA transposon sequence (native sequence) were analyzed for their ability to participate in a transposition reaction. A transposon library comprising transposon ends with degenerated nucleotides introduced in locations that, based on scientific literature are referred to as conserved sites, was prepared and used for the transposition reaction catalyzed by MuA. Resulting transposition products were sequenced and analyzed in terms of sequence variation.

Figure 13:
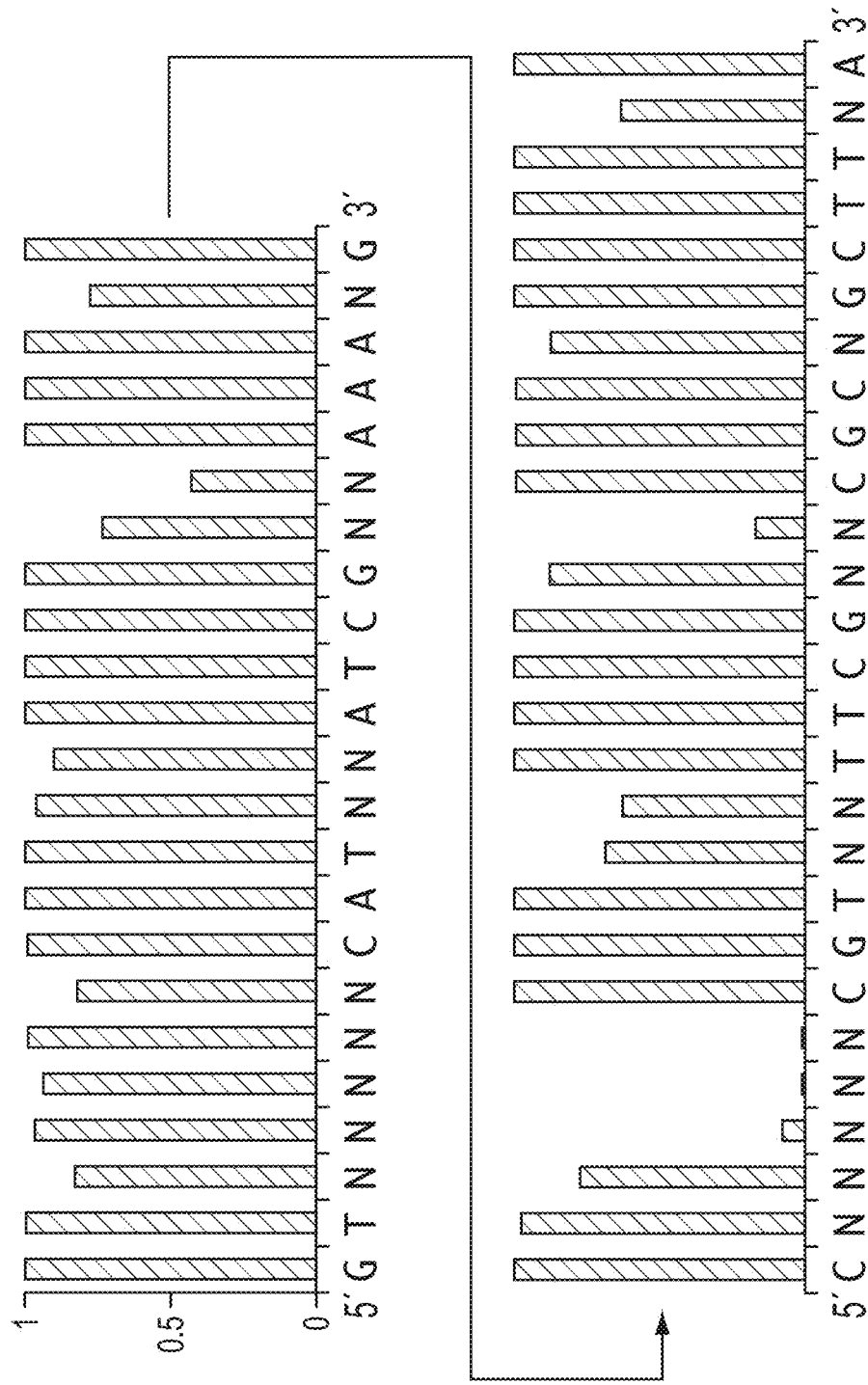
FIG. 13 represents deviations from the theoretical expected distribution of nucleotide replacements (degeneration) in MuA transposon end sequence.
Figure 14A:
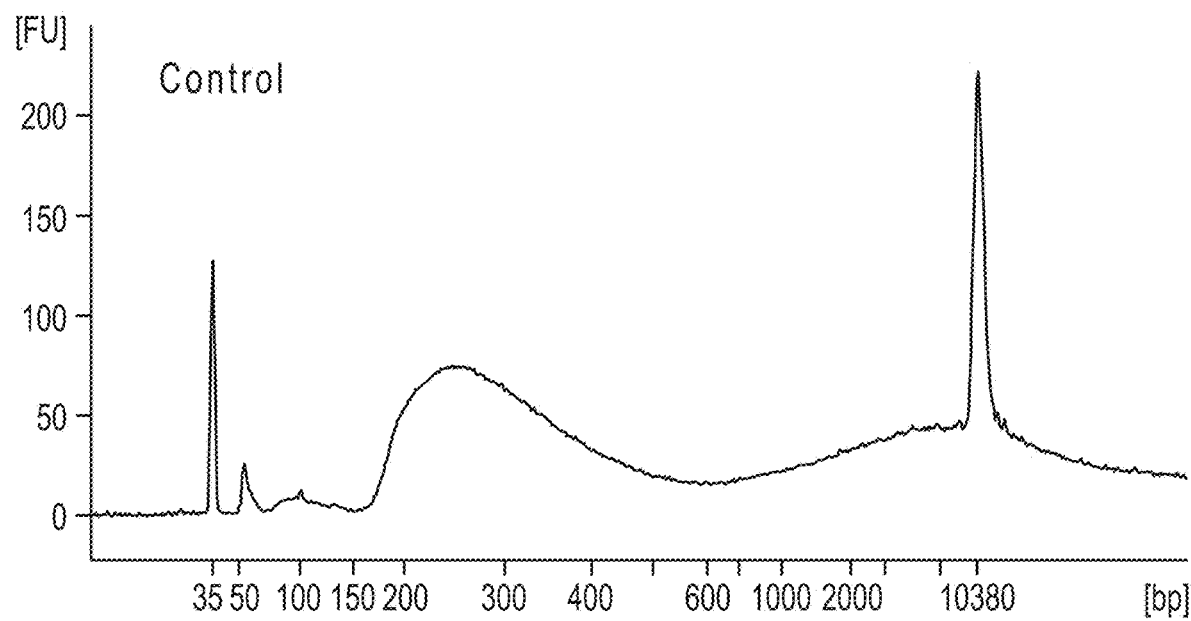
FIG. 14A shows an Agilent 2100 Bioanalyzer profile of control non-fragmented E. coli gDNA.
Figure 14B:
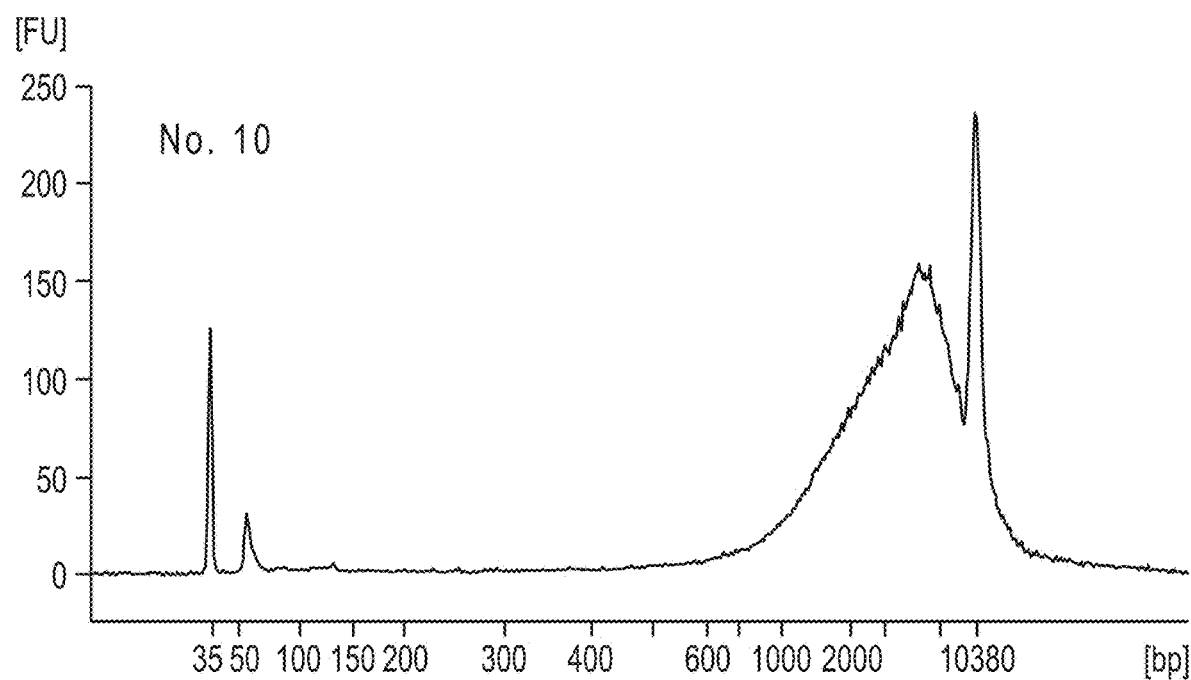
FIG. 14B shows an Agilent 2100 Bioanalyzer profile of fragmented E. coli gDNA obtained with transposome complexes comprising modified (degenerate) transposon ends (No. 10).
Figure 14C:
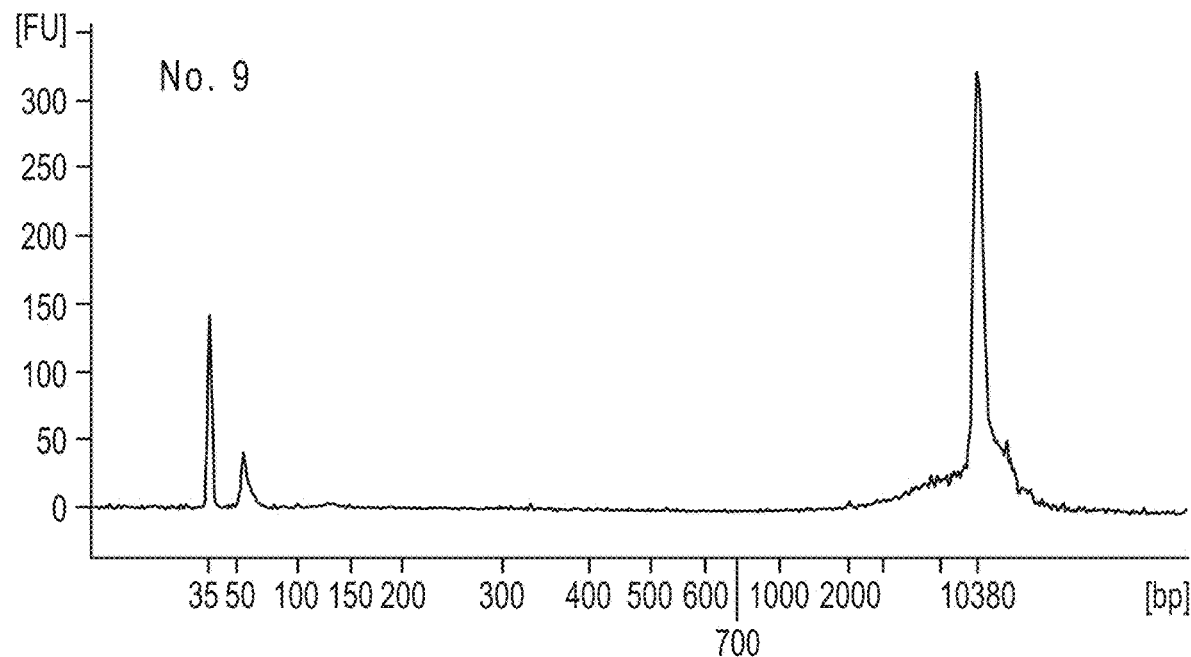
FIG. 14C shows an Agilent 2100 Bioanalyzer profile of fragmented E. coli gDNA obtained with transposome complexes comprising modified (degenerate) transposon ends (No. 9).
Figure 14D:
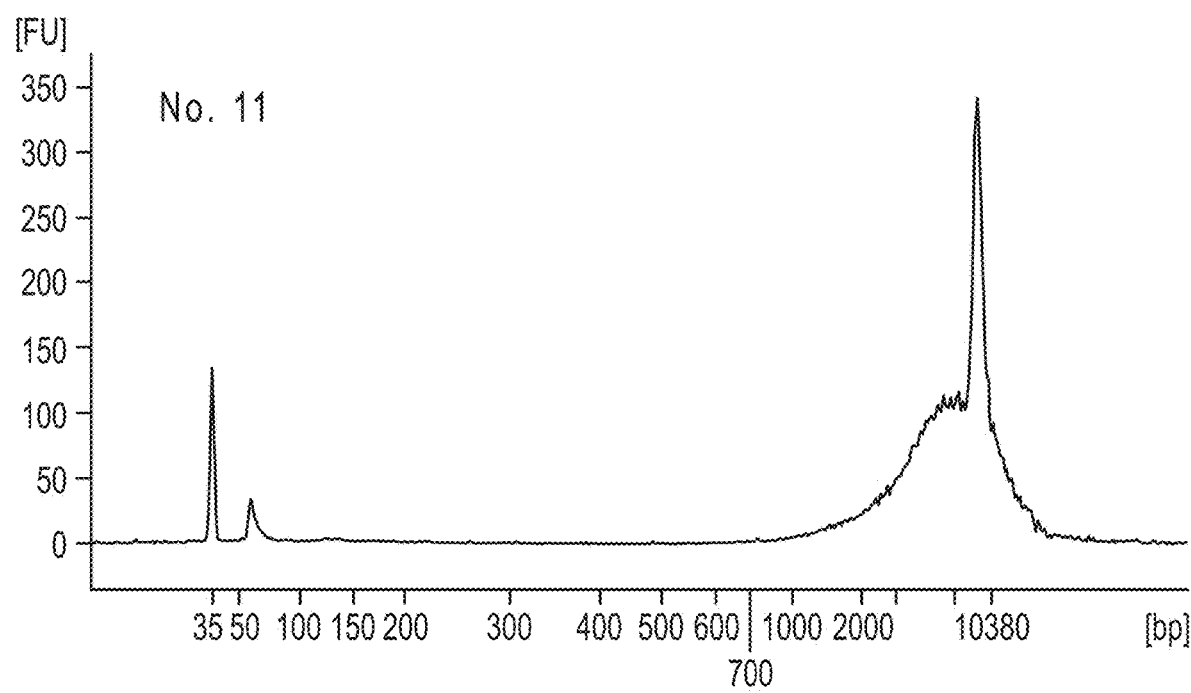
FIG. 14D shows an Agilent 2100 Bioanalyzer profile of fragmented E. coli gDNA obtained with transposome complexes comprising modified (degenerate) transposon ends (No. 11).
Figure 14E:
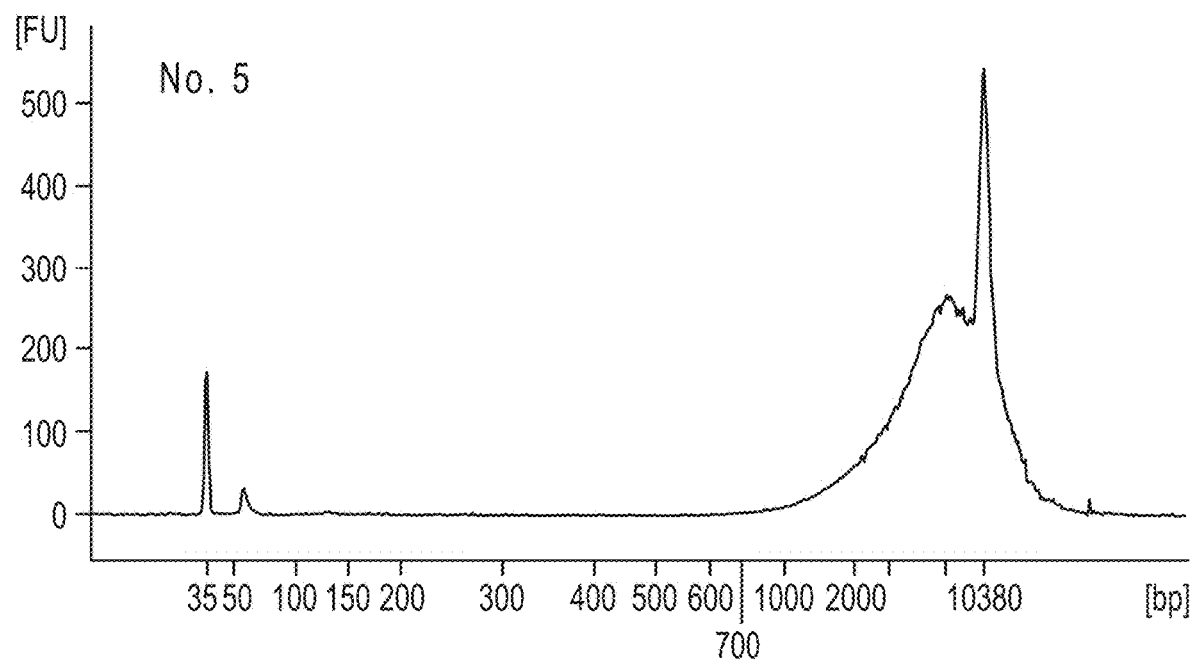
FIG. 14E shows an Agilent 2100 Bioanalyzer profile of fragmented E. coli gDNA obtained with transposome complexes comprising modified (degenerate) transposon ends (No. 5).

Results are shown in FIG. 13. In this experiment degenerated nucleotide mixtures were prepared so each N represents a special wobble mixture, where nucleotide found in the wild-type transposon sequence was retained with 70% frequency, while other three nucleotides were inserted with equal frequencies of 10%:10%:10%. Number 1 on vertical axis represents 100% congruence between expected nucleotide distribution frequency (70%:10%:10%:10%) and factual frequency calculated from sequencing data. The smaller the number on vertical axis, the higher deviation from expected nucleotide distribution frequency was observed at a certain position. For simplicity only the transferred DNA strand is shown.

Not all the conserved positions were found to be of high importance for the transposition efficiency in the experimental framework. However, MuA transposase has some preferences towards a number of positions in a transposon. Thus, the skilled person in the art may design different transposons for which MuA transposase has lower affinity. Afterwards, several modified transposons that were still able to support transposition reaction, albeit with lower efficiency, were selected and analyzed.

Several different transposons selected in the first experiment as capable of supporting transposition (Table 3) were used for transposome complex formation with MuA transposase in equimolar concentrations as described above. The final concentration of transposon DNA was 8 µM and for MuA transposase 1.65 g/l in complex assembly reaction. After one hour incubation at 30° C., complex assembly mix was diluted with Dilution Buffer. The final diluted MuA transposome complex concentration was about 0.48 g/l. MuA transposome complex was stored at −70° C. for at least 16 hours before use. Subsequently, E. coli genomic DNA was subjected to the fragmentation reaction employing the pre-formed complexes. Fragmentation reaction products were purified by Agencourt AMPure XP system (Beckman Coulter) and analyzed on Agilent 2100 Bioanalyzer using Agilent High Sensitivity DNA Kit (Agilent Biotechnologies) following manufacturer's recommendations. FIG. 14 shows that gDNA fragmentation was very efficient when Control transposon (native transposon end sequence) was used, while for modified transposon ends fragmentation was apparent only with transposon Nos. 5, 10, and 11. Fragmentation was completely abolished when transposon No. 9 was used.

Figure 15:
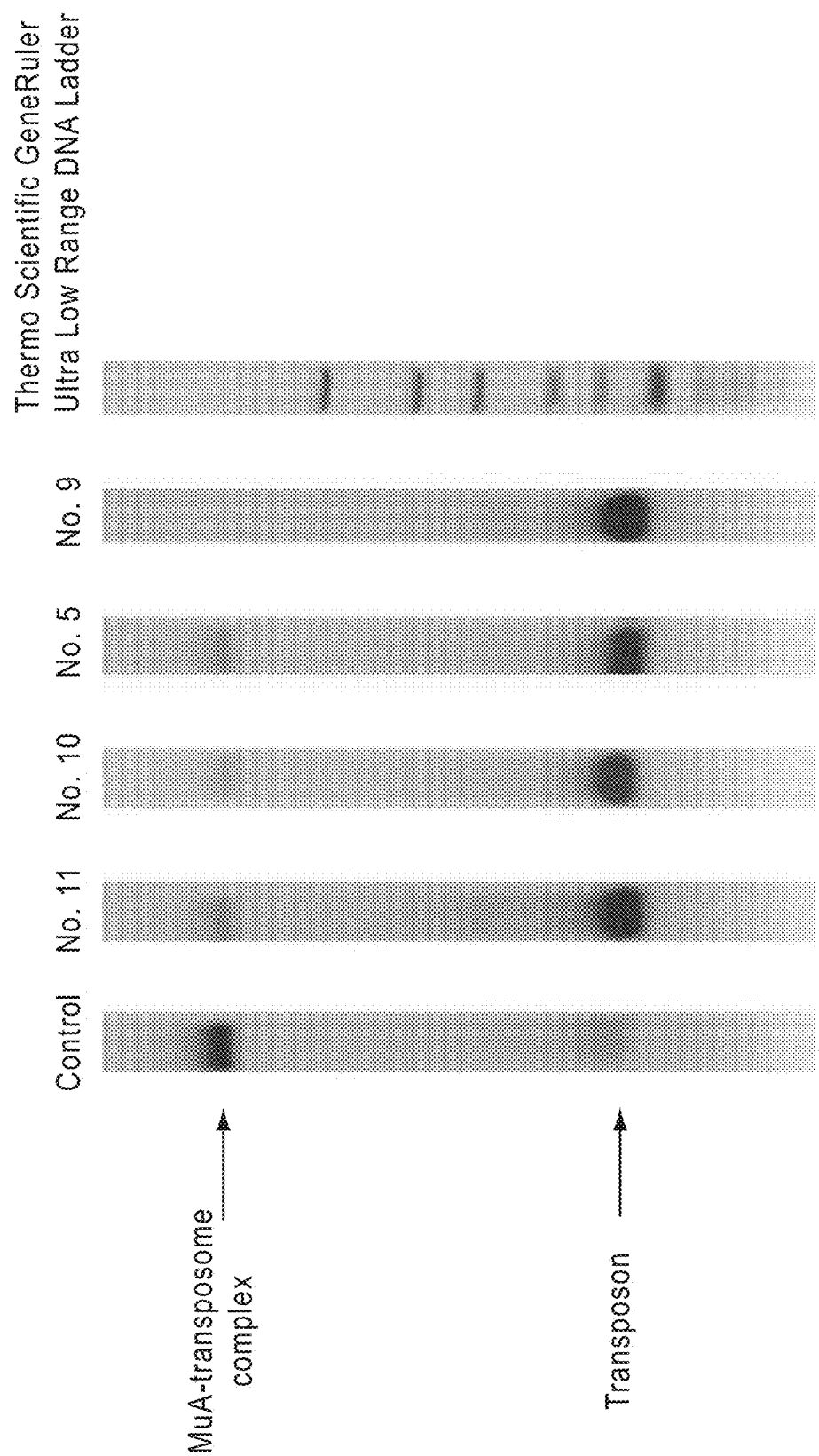
FIG. 15 shows EMSA analysis of the MuA-modified transposon complexes.

In parallel, EMSA analysis was performed for all pre-formed MuA-transposon complexes used in the first experiment (Table 3). EMSA analysis results are shown in FIG. 15. DNA shifts resulting from transposome complex formation were analyzed using agarose gel electrophoresis in 2% agarose gel containing 87 µg/ml BSA and 87 µg/ml heparin in 1×TBE buffer. DNA was stained with ethidium bromide. The results show that strong complexes formed only when MuA transposase was complexed with control (native) transposon. Weaker complexes were formed with transposons No. 5, 10, 11. These data correlate well with results in FIG. 13. With transposon No. 9 there was no apparent complex formation, indicating that MuA does not bind to this particular DNA sequence. This explains absence of fragmentation using this transposome complex shown in FIG. 13.

Experimental results presented in FIGS. 13 and 14 clearly indicate that decreased fragmentation level (efficiency) obtained with modified transposons is a consequence of the reduced affinity of MuA transposase towards the modified transposon ends. Thus, the level of fragmentation, and the average length of the fragmentation products, can be changed either by varying the sequence of the native transposon end or by varying the amounts of genomic DNA and preassembled transposome complex comprising modified transposon ends.

tube produced AA-PCR. This was demonstrated by comparing the outcome of PCR of E. coli gDNA fragmented with the MuA transpososome containing the stated nicked transposon end and the MuA transpososome containing the standard full-length transposon end.

Transposon ends (final concentration 60 µM) were prepared by annealing equimolar quantities of primers Cut-key4 (1Nick34-16), Cut-key4 (2Nick34-16) and Non-cut-key4 (1Nick42-11), Non-cut-key4 (2Nick42-11) or Cut-key4 (No_nick) and Non-cut-key4 in 10 mM Tris-HCl (pH 8.0), 1 mM EDTA, 50 mM NaCl, following the conditions described in Materials and Methods.

TABLE 3

Double-stranded transposon sequences.

| SEQ ID NO | Transposon variant | Double-stranded transposon sequence |
|---|---|---|
| 35 | Control | 5'-GTTTTCGCATTTATCGTGAAACGCTTTCGCGTTTTTCGTGCGTCAGTTCA |
| 36 | | 3'-CAAAAGCGTAAATAGCACTTTGCGAAAGCGCAAAAAGCACGCAGTCAAGTCGT |
| 37 | No. 5 | 5'-GTCATTACATTGATCGTGAAAGGCTTTCGCGTTGTTCGAGCGCCGCTTTA |
| 38 | | 3'-CAGTAATGTAACTAGCACTTTCCGAAAGCGCAACAAGCTCGCGGCGAAATCGT |
| 39 | No. 9 | 5'-GTTCTCGCATCTATCGTGAAAAGCTTCTCCGTTCTTCGGCCGCCGCTTCA |
| 40 | | 3'-CAAGAGCGTAGATAGCACTTTTCGAAGAGGCAAGAAGCCGGCGGCGAAGTCGT |
| 41 | No. 10 | 5'-GTGCTTTCATTTATCGGGAAACGCTGTCGCGTTGTTCGTGCGCAGCTTTA |
| 42 | | 3'-CACGAAAGTAAATAGCCCTTTGCGACAGCGCAACAAGCACGCGTCGAAATCGT |
| 43 | No. 11 | 5'-GTTTGTGCATATATCGTAAAAAGCACTCGCGTATTTCGTGCGCCGCTTAA |
| 44 | | 3'-CAAACACGTATATAGCATTTTTCGTGAGCGCATAAAGCACGCGGCGAATTCGT |

Example 7

The Use of Tn5 Transpososomes Containing Nicked or Gapped Transposon Ends as a Controlled DNA Fragmentation Tool Enabling Generation of DNA Fragments with Predefined Average Length The hypervariable Tn5 transposase gene is synthesized, cloned, and overexpressed in E. coli. Tn5 transposase protein is purified and synaptic complexes are made with relevant transposon ends, intact or harboring an abasic site, nick, or gap in several locations where it was shown that such a modified sequence does not interfere with transposase binding to its recognition sequence. Such transposome complexes are evaluated for their ability to shear DNA in a controlled manner.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

Example 8

The Use of MuA Transposase in Combination with Pre-Nicked Transposon Ends for DNA Fragmentation, Adapter Addition and Amplification Reaction in Single Tube DNA fragments generated using MuA transpososome containing Cut key4 (34-16) and Non-cut key4 (42-11) pre-nicked transposon ends and after fragmentation in same MuA transposomes were formed in complex assembly buffer with extra DMSO. The final concentration of transposon end was 8 µM and for MuA transposase 1.65 g/l in the complex assembly reaction. After one hour incubation at 30° C., the complex assembly mix was diluted with dilution buffer. Final diluted MuA transposome complex concentration was about 0.48 g/l. MuA transposome complex was stored at −70° C. for at least 16 hours before use.

E. coli gDNA was fragmented in parallel with MuA transpososome containing either 34-16/42-11 pre-nicked transposon end or a standard full length transposon end. Reactions were performed using 100 ng E. coli DNA in AA-PCR reaction buffer. Immediately after adding the transposome mix (1.5 µl to final reaction volume 30 µl), vortexing and a short spin-down, the tube was incubated at 30° C. for five minutes.

Fragmented E. coli gDNAs served as templates for PCR amplification with Phusion Hot Start II High-Fidelity DNA polymerase (Thermo Scientific) and 4 primers: A and P1-Ion platform specific adaptors with transposon end sequences, A' and P1'-PCR amplification primers.

```
                                        (SEQ ID NO: 23)
A    5'-CCATCTCATCCCTGCGTGTCTTCGTGCGTCAGTTCA-3', (SEQ ID NO: 24)
P1   5'-CCACTACGCCTCCGCTTTCCTCTCTATGGGCAGTCGGTGATTT
     CGTGCGTCAGTTCA-3', (SEQ ID NO: 25)
A'   5'-CCATCTCATCCCTGCGTGTC-3', (SEQ ID NO: 26)
P1'  5'-CCACTACGCCTCCGCTTTCCTCTCTATG-3'.
```

Reactions were carried out using 30 µl of fragmented DNA (in final volume of 50 µl) in 10 mM Tris-HCl, pH 8.8, 110 mM KCl, 1.5 mM MgCl$_2$, 0.1% (w/v), Triton X-100, 200 μM dATP, 200 μM dTTP, 200 μM dCTP, 200 μM dGTP using the following cycling conditions: 66° C. 3', 1×98° C. 30"; 9×98° C. 10", 60° C. 50", 72° C. 10"; 1×72° C. 1'.

Amplified DNA was purified using the GeneJET NGS Cleanup kit (Thermo Fisher Scientific) system. Amplified DNA was transferred into a 1.5 ml tube. Then 250 μl of thoroughly mixed GeneJET NGS Cleanup kit (Thermo Fisher Scientific) biding buffer and 50 μl of 96% ethanol was added into tube with sample and vortexed. After a short spin, solution was transferred to the purification column preassembled with a collection tube and centrifuged for 30 s at 10 000×g. Flow-through was discarded. 200 μl pre-wash buffer added to the purification column preassembled with a collection tube and centrifuged for 30 s at 10 000×g. Flow-through was discarded. 700 μl wash (supplemented with ethanol) buffer added to the purification column preassembled with a collection tube and centrifuged for 30 s at 10 000×g. Flow-through was discarded. Wash step repeated one more time again. Empty column spined at 14 000 g for 2 min. to completely remove residual wash buffer. Purification column was transferred into clean 1.5 mL microcentrifuge tube. 20 μl H$_2$O was added to the center of the purification column and centrifuged at 14 000×g for 1 min. Supernatants containing the eluted DNA was collected.

DNA samples after PCR amplification were analyzed using the Agilent 2100 Bioanalyzer (Agilent Biotechnologies) and the Agilent High Sensitivity DNA Kit (Agilent Biotechnologies). Before analysis, fragmented DNA was diluted with nuclease free water by a factor of 2, while amplified samples by a factor of 4.

Figure 16:
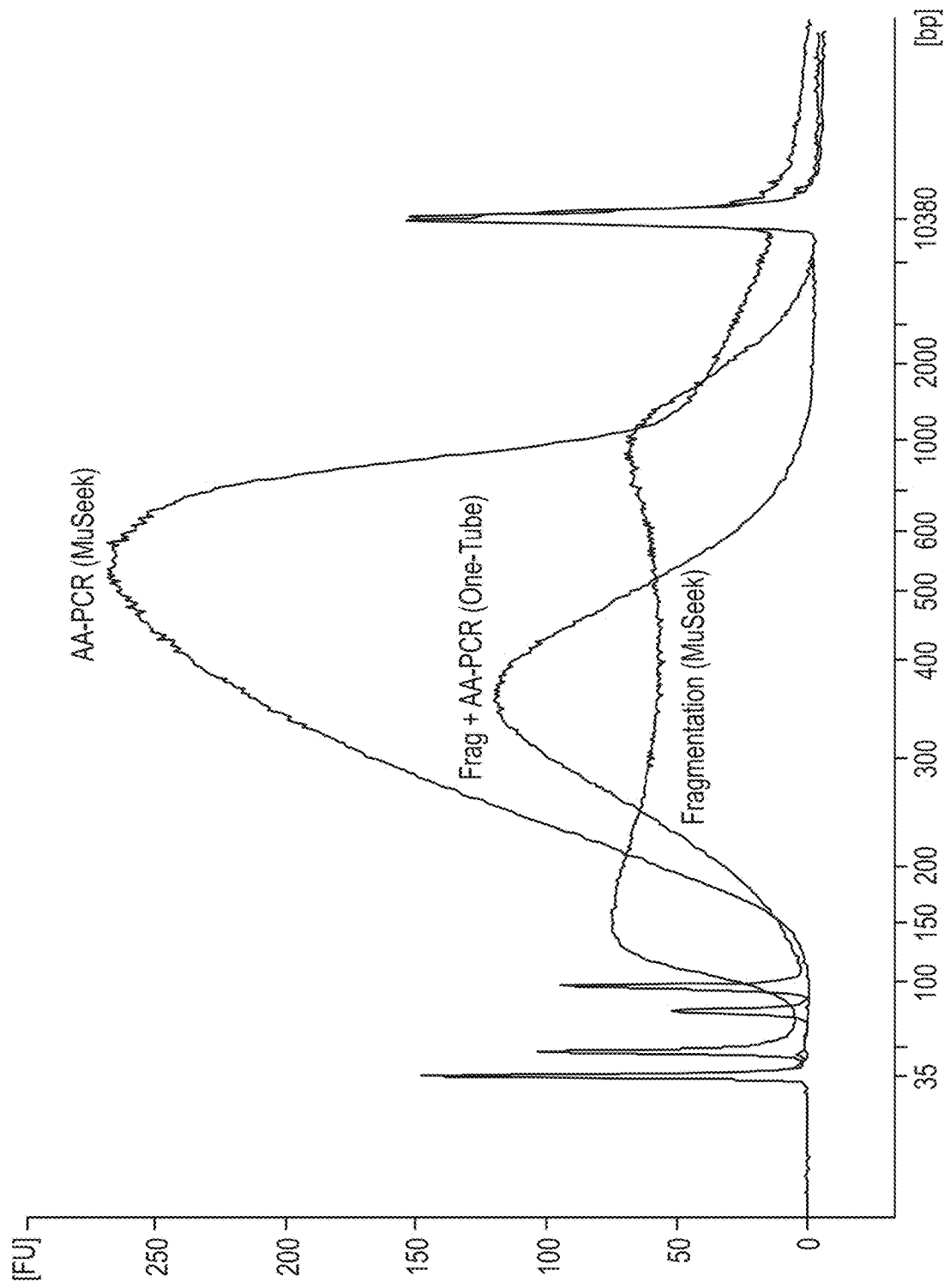
FIG. 16 shows Agilent 2100 Bioanalyzer curves of fragmented (using native transposon ends and 34-16 pre-nicked transposon ends) and then amplified human gDNA.

The results are shown in FIG. 16. They revealed that fragmentation reaction and AA-PCR could be combined in the same tube without purification after fragmentation. DNA samples fragmented with MuA transpososome containing the transposon ends having a nick after 16$^{th}$ position (from the 3' end) of Cut-key4 oligonucleotide and a nick after 11$^{th}$ position (from the 5' end) of Non-cut-key4 oligonucleotide resulted in reduced amount of DNA fragments with protein-DNA complexes after fragmentation that are unwanted then producing more than one reaction in the same tube, thus significantly improving the quality of PCR-amplified DNA library.

What is claimed:

1. A method for fragmenting nucleic acids from an initial nucleic acid sample in an in vitro reaction, comprising:
   a) providing a plurality of transpososome complexes, which include (i) a plurality of transposases, (ii) a first transposon end sequence, wherein the first transposon end sequence is capable of binding to a transposase from the plurality of transposases and wherein the first transposon end sequence contains at least one nick or gap, (iii) a second transposon end sequence, wherein the second transposon end sequence is capable of binding to a transposase from the plurality of transposases and wherein the second transposon end sequence contains at least one nick or gap;
   b) contacting, in a single reaction mixture, the plurality of transpososome complexes with the nucleic acids, under conditions that are suitable for transposing the first and second transposon end sequences into the nucleic acids and fragmenting the nucleic acids, where the nucleic acids includes a first nucleic acid molecule; and
   c) producing at least one fragmented tagged DNA molecule having a first end joined to the first transposon end sequence and a second end joined to the second transposon end sequence, by transposing the first transposon end sequences into the first nucleic acid molecule at a first position and fragmenting and tagging the first nucleic acid molecule, and by transposing the second transposon end sequences into first nucleic acid molecule at a second position and fragmenting and tagging the first nucleic acid molecule, wherein the at least one fragmented tagged DNA molecules includes the first transposon end sequence having at least one nick or gap, and a second end having at least one nick or gap.

2. The method of claim 1, wherein the initial nucleic acid sample includes RNA or DNA.

3. The method of claim 1, wherein the initial nucleic acid sample includes genomic DNA or cell-free DNA.

4. The method of claim 1, wherein the plurality of transpososome complexes comprises a plurality of homo-transpososome complexes or a mixture of hetero-transpososome complexes, wherein the homo-transpososome complexes include transposases bound to transposon end sequences having the same sequence of the first transposon end sequence, and wherein the mixture of hetero-transpososome complexes includes transpososome complexes comprising transposases bound to transposon end sequences having the sequence of the first or the second transposon end sequence.

5. The method of claim 4, wherein the mixture of hetero-transpososome complexes includes transposases bound to transposon end sequences having one of 2-100 different transposon end sequences.

6. The method of claim 1, further comprising: appending at least one universal adaptor sequence to the first end of the fragmented tagged DNA molecule which is joined to the first transposon end sequence.

7. The method of claim 1, further comprising: appending at least one universal adaptor sequence to the second end of the fragmented tagged DNA molecule which is joined to the second transposon end sequence.

8. The method of claim 6, wherein the universal adaptor sequence comprises an amplification primer sequence, a sequencing primer sequence and/or a barcode sequence.

9. The method of claim 6, further comprising: amplifying the at least one fragmented tagged DNA molecule to generate tagged DNA amplicons.

10. The method of claim 9, further comprising: sequencing the tagged DNA amplicons to generate a plurality of sequencing reads.

11. The method of claim 10, further comprising: aligning the sequencing reads to at least one reference sequence.

12. The method of claim 10, wherein at least one sequencing read contains one or more mutations, selected from a group consisting of point mutations, deletions, insertions, and substitutions of one or more nucleotides, inversions, rearrangements, fusions, truncations, transversions, transitions, non-sense mutations, translocations, duplications, sequence repeats, fusion sequences, single nucleotide polymorphism (SNP), copy number variation (CNV) and/or variant or abnormal splice junction sequences.

13. The method of claim 10, further comprising: quantifying the number of sequencing reads that correspond to a first target sequence of interest from the initial nucleic sample to obtain a first number.

14. The method of claim 10, wherein the sequencing comprises a massively parallel sequencing reaction.

15. The method of claim 14, wherein the massively parallel sequencing reaction comprises incorporating a nucleotide.

16. The method of claim 14, wherein the massively parallel sequencing reaction comprises providing a surface having an array of a plurality of reaction sites, and the reaction site is operatively linked to a sensor.

17. The method of claim 16, wherein the sensor detects a change in ions, hydrogen ions, protons, phosphate groups, or pyrophosphate groups.

18. The method of claim 16, wherein the sensor detects at least one byproduct or cleavage product of a nucleotide incorporation reaction.

19. The method of claim 18, wherein the byproduct or cleavage product of a nucleotide incorporation reaction includes hydrogen ions, protons, phosphate groups, or pyrophosphate groups.

20. The method of claim 18, wherein the sensor comprises an ion-sensitive field effect transistor (ISFET).

* * * * *

SEQUENCE LISTING

```
<160> NUMBER OF SEQ ID NOS: 44

<210> SEQ ID NO 1
<211> LENGTH: 30
<212> TYPE: DNA
<213> ORGANISM: Artificial Sequence
<220> FEATURE:
<223> OTHER INFORMATION: Synthetic: Non-cut-key4

<400> SEQUENCE: 1
gcgaaagcgt ttcacgataa atgcgaaaac                                    30

<210> SEQ ID NO 2
<211> LENGTH: 50
<212> TYPE: DNA
<213> ORGANISM: Artificial Sequence
<220> FEATURE:
<223> OTHER INFORMATION: Synthetic: Cut-key4 (No_nick)

<400> SEQUENCE: 2
gttttcgcat ttatcgtgaa acgctttcgc gtttttcgtg cgtcagttca             50

<210> SEQ ID NO 3
<211> LENGTH: 45
<212> TYPE: DNA
<213> ORGANISM: Artificial Sequence
<220> FEATURE:
<223> OTHER INFORMATION: Synthetic: Cut-key4 (1 Nick45-5)

<400> SEQUENCE: 3
gttttcgcat ttatcgtgaa acgctttcgc gtttttcgtg cgtca                  45

<210> SEQ ID NO 4
<211> LENGTH: 5
<212> TYPE: DNA
<213> ORGANISM: Artificial Sequence
<220> FEATURE:
<223> OTHER INFORMATION: Synthetic: Cut-key4 (2 Nick45-5)

<400> SEQUENCE: 4 gttca                                                               5
```

```
<210> SEQ ID NO 5
<211> LENGTH: 44
<212> TYPE: DNA
<213> ORGANISM: Artificial Sequence
<220> FEATURE:
<223> OTHER INFORMATION: Synthetic: Cut-key4 (1 Nick44-6)

<400> SEQUENCE: 5
gttttcgcat ttatcgtgaa acgctttcgc gttttttcgtg cgtc                    44

<210> SEQ ID NO 6
<211> LENGTH: 6
<212> TYPE: DNA
<213> ORGANISM: Artificial Sequence
<220> FEATURE:
<223> OTHER INFORMATION: Synthetic: Cut-key4 (2 Nick44-6)

<400> SEQUENCE: 6 agttca                                                                6

<210> SEQ ID NO 7
<211> LENGTH: 42
<212> TYPE: DNA
<213> ORGANISM: Artificial Sequence
<220> FEATURE:
<223> OTHER INFORMATION: Synthetic: Cut-key4 (1 Nick42-8)

<400> SEQUENCE: 7
gttttcgcat ttatcgtgaa acgctttcgc gttttttcgtg cg                      42

<210> SEQ ID NO 8
<211> LENGTH: 8
<212> TYPE: DNA
<213> ORGANISM: Artificial Sequence
<220> FEATURE:
<223> OTHER INFORMATION: Synthetic: Cut-key4 (2 Nick42-8)

<400> SEQUENCE: 8 tcagttca                                                              8

<210> SEQ ID NO 9
<211> LENGTH: 40
<212> TYPE: DNA
<213> ORGANISM: Artificial Sequence
<220> FEATURE:
<223> OTHER INFORMATION: Synthetic: Cut-key4 (1 Nick40-10)

<400> SEQUENCE: 9
gttttcgcat ttatcgtgaa acgctttcgc gttttttcgtg                         40

<210> SEQ ID NO 10
<211> LENGTH: 10
<212> TYPE: DNA
<213> ORGANISM: Artificial Sequence
<220> FEATURE:
<223> OTHER INFORMATION: Synthetic: Cut-key4 (2 Nick40-10)

<400> SEQUENCE: 10
cgtcagttca                                                           10

<210> SEQ ID NO 11
<211> LENGTH: 38
<212> TYPE: DNA
<213> ORGANISM: Artificial Sequence
<220> FEATURE:
<223> OTHER INFORMATION: Synthetic: Cut-key4 (1 Nick38-12)
```

-continued

<400> SEQUENCE: 11
gttttcgcat ttatcgtgaa acgctttcgc gtttttcg                              38

<210> SEQ ID NO 12
<211> LENGTH: 12
<212> TYPE: DNA
<213> ORGANISM: Artificial Sequence
<220> FEATURE:
<223> OTHER INFORMATION: Synthetic: Cut-key4 (2 Nick38-12)

<400> SEQUENCE: 12
tgcgtcagtt ca                                                          12

<210> SEQ ID NO 13
<211> LENGTH: 36
<212> TYPE: DNA
<213> ORGANISM: Artificial Sequence
<220> FEATURE:
<223> OTHER INFORMATION: Synthetic: Cut-key4 (1 Nick36-14)

<400> SEQUENCE: 13
gttttcgcat ttatcgtgaa acgctttcgc gttttt                                36

<210> SEQ ID NO 14
<211> LENGTH: 14
<212> TYPE: DNA
<213> ORGANISM: Artificial Sequence
<220> FEATURE:
<223> OTHER INFORMATION: Synthetic: Cut-key4 (2 Nick36-14)

<400> SEQUENCE: 14
cgtgcgtcag ttca                                                        14

<210> SEQ ID NO 15
<211> LENGTH: 34
<212> TYPE: DNA
<213> ORGANISM: Artificial Sequence
<220> FEATURE:
<223> OTHER INFORMATION: Synthetic: Cut-key4 (1 Nick34-16)

<400> SEQUENCE: 15
gttttcgcat ttatcgtgaa acgctttcgc gttt                                  34

<210> SEQ ID NO 16
<211> LENGTH: 16
<212> TYPE: DNA
<213> ORGANISM: Artificial Sequence
<220> FEATURE:
<223> OTHER INFORMATION: Synthetic: Cut-key4 (2 Nick34-16)

<400> SEQUENCE: 16
ttcgtgcgtc agttca                                                      16

<210> SEQ ID NO 17
<211> LENGTH: 32
<212> TYPE: DNA
<213> ORGANISM: Artificial Sequence
<220> FEATURE:
<223> OTHER INFORMATION: Synthetic: Cut-key4 (1 Nick32-18)

<400> SEQUENCE: 17
gttttcgcat ttatcgtgaa acgctttcgc gt                                    32

<210> SEQ ID NO 18
<211> LENGTH: 18

<212> TYPE: DNA
<213> ORGANISM: Artificial Sequence
<220> FEATURE:
<223> OTHER INFORMATION: Synthetic: Cut-key4 (2 Nick32-18)

<400> SEQUENCE: 18
ttttcgtgcg tcagttca                                                          18

<210> SEQ ID NO 19
<211> LENGTH: 31
<212> TYPE: DNA
<213> ORGANISM: Artificial Sequence
<220> FEATURE:
<223> OTHER INFORMATION: Synthetic: Cut-key4 (1 Nick31-19)

<400> SEQUENCE: 19
gttttcgcat ttatcgtgaa acgctttcgc g                                           31

<210> SEQ ID NO 20
<211> LENGTH: 19
<212> TYPE: DNA
<213> ORGANISM: Artificial Sequence
<220> FEATURE:
<223> OTHER INFORMATION: Synthetic: Cut-key4 (2 Nick31-19)

<400> SEQUENCE: 20
tttttcgtgc gtcagttca                                                         19

<210> SEQ ID NO 21
<211> LENGTH: 23
<212> TYPE: DNA
<213> ORGANISM: Artificial Sequence
<220> FEATURE:
<223> OTHER INFORMATION: Synthetic: Cut-key4 (1 Nick23-27)

<400> SEQUENCE: 21
gttttcgcat ttatcgtgaa acg                                                    23

<210> SEQ ID NO 22
<211> LENGTH: 27
<212> TYPE: DNA
<213> ORGANISM: Artificial Sequence
<220> FEATURE:
<223> OTHER INFORMATION: Synthetic: Cut-key4 (2 Nick23-27)

<400> SEQUENCE: 22
ctttcgcgtt tttcgtgcgt cagttca                                                27

<210> SEQ ID NO 23
<211> LENGTH: 36
<212> TYPE: DNA
<213> ORGANISM: Artificial Sequence
<220> FEATURE:
<223> OTHER INFORMATION: Synthetic: Primer A

<400> SEQUENCE: 23
ccatctcatc cctgcgtgtc ttcgtgcgtc agttca                                      36

<210> SEQ ID NO 24
<211> LENGTH: 57
<212> TYPE: DNA
<213> ORGANISM: Artificial Sequence
<220> FEATURE:
<223> OTHER INFORMATION: Synthetic: Primer P1

<400> SEQUENCE: 24
ccactacgcc tccgctttcc tctctatggg cagtcggtga tttcgtgcgt cagttca     57

<210> SEQ ID NO 25
<211> LENGTH: 20
<212> TYPE: DNA
<213> ORGANISM: Artificial Sequence
<220> FEATURE:
<223> OTHER INFORMATION: Synthetic: Primer A'

<400> SEQUENCE: 25
ccatctcatc cctgcgtgtc                                              20

<210> SEQ ID NO 26
<211> LENGTH: 28
<212> TYPE: DNA
<213> ORGANISM: Artificial Sequence
<220> FEATURE:
<223> OTHER INFORMATION: Synthetic: Primer P1'

<400> SEQUENCE: 26
ccactacgcc tccgctttcc tctctatg                                     28

<210> SEQ ID NO 27
<211> LENGTH: 53
<212> TYPE: DNA
<213> ORGANISM: Artificial Sequence
<220> FEATURE:
<223> OTHER INFORMATION: Synthetic: Non-cut-key4

<400> SEQUENCE: 27
acgacttgac tgcgtgcttt ttgcgctttc gcaaagtgct atttacgctt ttg          53

<210> SEQ ID NO 28
<211> LENGTH: 50
<212> TYPE: DNA
<213> ORGANISM: Artificial Sequence
<220> FEATURE:
<223> OTHER INFORMATION: Synthetic: Cut-key4 (No_nick)

<400> SEQUENCE: 28
gttttcgcat ttatcgtgaa acgctttcgc gttttcgtg cgtcagttca              50

<210> SEQ ID NO 29
<211> LENGTH: 38
<212> TYPE: DNA
<213> ORGANISM: Artificial Sequence
<220> FEATURE:
<223> OTHER INFORMATION: Synthetic: Cut-key4 (1Nick 38-12)

<400> SEQUENCE: 29
gttttcgcat ttatcgtgaa acgctttcgc gttttcg                           38

<210> SEQ ID NO 30
<211> LENGTH: 12
<212> TYPE: DNA
<213> ORGANISM: Artificial Sequence
<220> FEATURE:
<223> OTHER INFORMATION: Synthetic: Cut-key4 (2Nick 38-12)

<400> SEQUENCE: 30
tgcgtcagtt ca                                                      12

<210> SEQ ID NO 31
<211> LENGTH: 42
<212> TYPE: DNA
<213> ORGANISM: Artificial Sequence

```
<220> FEATURE:
<223> OTHER INFORMATION: Synthetic: Cut-key4 (1Gap 42-6)

<400> SEQUENCE: 31
gttttcgcat ttatcgtgaa acgctttcgc gttttcgtg cg                              42

<210> SEQ ID NO 32
<211> LENGTH: 6
<212> TYPE: DNA
<213> ORGANISM: Artificial Sequence
<220> FEATURE:
<223> OTHER INFORMATION: Synthetic: Cut-key4 (2Gap 42-6)

<400> SEQUENCE: 32 agttca                                                                     6

<210> SEQ ID NO 33
<211> LENGTH: 40
<212> TYPE: DNA
<213> ORGANISM: Artificial Sequence
<220> FEATURE:
<223> OTHER INFORMATION: Synthetic: Cut-key4 (1Gap 40-8)

<400> SEQUENCE: 33
gttttcgcat ttatcgtgaa acgctttcgc gttttcgtg                                 40

<210> SEQ ID NO 34
<211> LENGTH: 8
<212> TYPE: DNA
<213> ORGANISM: Artificial Sequence
<220> FEATURE:
<223> OTHER INFORMATION: Synthetic: Cut-key4 (2Gap 40-8)

<400> SEQUENCE: 34 tcagttca                                                                   8

<210> SEQ ID NO 35
<211> LENGTH: 50
<212> TYPE: DNA
<213> ORGANISM: Artificial Sequence
<220> FEATURE:
<223> OTHER INFORMATION: Synthetic: Control transposon sequence

<400> SEQUENCE: 35
gttttcgcat ttatcgtgaa acgctttcgc gttttcgtg cgtcagttca                      50

<210> SEQ ID NO 36
<211> LENGTH: 53
<212> TYPE: DNA
<213> ORGANISM: Artificial Sequence
<220> FEATURE:
<223> OTHER INFORMATION: Synthetic: Control transposon sequence

<400> SEQUENCE: 36
tgctgaactg acgcacgaaa acgcgaaag cgtttcacga taaatgcgaa aac                  53

<210> SEQ ID NO 37
<211> LENGTH: 50
<212> TYPE: DNA
<213> ORGANISM: Artificial Sequence
<220> FEATURE:
<223> OTHER INFORMATION: Synthetic: No. 5 transposon sequence

<400> SEQUENCE: 37
gtcattacat tgatcgtgaa aggctttcgc gttgttcgag cgccgcttta                     50
```

<210> SEQ ID NO 38
<211> LENGTH: 53
<212> TYPE: DNA
<213> ORGANISM: Artificial Sequence
<220> FEATURE:
<223> OTHER INFORMATION: Synthetic: No. 5 transposon sequence

<400> SEQUENCE: 38
tgctaaagcg gcgctcgaac aacgcgaaag cctttcacga tcaatgtaat gac    53

<210> SEQ ID NO 39
<211> LENGTH: 50
<212> TYPE: DNA
<213> ORGANISM: Artificial Sequence
<220> FEATURE:
<223> OTHER INFORMATION: Synthetic: No. 9 transposon sequence

<400> SEQUENCE: 39
gttctcgcat ctatcgtgaa aagcttctcc gttcttcggc cgccgcttca    50

<210> SEQ ID NO 40
<211> LENGTH: 53
<212> TYPE: DNA
<213> ORGANISM: Artificial Sequence
<220> FEATURE:
<223> OTHER INFORMATION: Synthetic: No. 9 transposon sequence

<400> SEQUENCE: 40
tgctgaagcg gcggccgaag aacggagaag cttttcacga tagatgcgag aac    53

<210> SEQ ID NO 41
<211> LENGTH: 50
<212> TYPE: DNA
<213> ORGANISM: Artificial Sequence
<220> FEATURE:
<223> OTHER INFORMATION: Synthetic: No. 10 transposon sequence

<400> SEQUENCE: 41
gtgctttcat ttatcgggaa acgctgtcgc gttgttcgtg cgcagcttta    50

<210> SEQ ID NO 42
<211> LENGTH: 53
<212> TYPE: DNA
<213> ORGANISM: Artificial Sequence
<220> FEATURE:
<223> OTHER INFORMATION: Synthetic: No. 10 transposon sequence

<400> SEQUENCE: 42
tgctaaagct gcgcacgaac aacgcgacag cgtttcccga taaatgaaag cac    53

<210> SEQ ID NO 43
<211> LENGTH: 50
<212> TYPE: DNA
<213> ORGANISM: Artificial Sequence
<220> FEATURE:
<223> OTHER INFORMATION: Synthetic: No. 11 transposon sequence

<400> SEQUENCE: 43
gtttgtgcat atatcgtaaa aagcactcgc gtatttcgtg cgccgcttaa    50

<210> SEQ ID NO 44
<211> LENGTH: 53
<212> TYPE: DNA
<213> ORGANISM: Artificial Sequence
<220> FEATURE:
<223> OTHER INFORMATION: Synthetic: No. 11 transposon sequence

```
<400> SEQUENCE: 44
tgcttaagcg gcgcacgaaa tacgcgagtg ctttttacga tatatgcaca aac          53
```